(12) United States Patent
Yamada et al.

(10) Patent No.: US 6,344,134 B1
(45) Date of Patent: *Feb. 5, 2002

(54) METHOD FOR MEASURING NOX CONCENTRATION AND NOX CONCENTRATION SENSOR

(75) Inventors: Tessho Yamada, Aichi; Noboru Ishida, Gifu; Toshitaka Matsuura, Aichi; Yoshiro Noda, Gifu; Nobuhiro Hayakawa, Aichi; Norihiko Nadanami, Aichi; Satoshi Sugaya, Aichi; Takaki Otsuka, Tokyo; Masashi Ando; Takafumi Oshima, both of Aichi, all of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,001

(22) Filed: Jan. 15, 1999

(30) Foreign Application Priority Data

| Jan. 16, 1998 | (JP) | ............................................ | 10-007059 |
| Feb. 20, 1998 | (JP) | ............................................ | 10-038899 |
| Feb. 20, 1998 | (JP) | ............................................ | 10-056127 |
| Apr. 20, 1998 | (JP) | ............................................ | 10-109296 |
| Jul. 15, 1998 | (JP) | ............................................ | 10-200566 |
| Sep. 30, 1998 | (JP) | ............................................ | 10-293108 |

(51) Int. Cl.[7] ...................... G01N 27/407; G01N 27/419
(52) U.S. Cl. ...................... 205/781; 73/23.31; 204/425
(58) Field of Search ................. 204/425, 426, 204/427, 428; 205/781; 73/23.31

(56) References Cited

U.S. PATENT DOCUMENTS

| 4,272,329 A | 6/1981 | Hetrick et al. |
| 4,909,072 A | 3/1990 | Logothetis et al. |
| 5,034,112 A | 7/1991 | Murase et al. |
| 5,145,566 A | 9/1992 | Logothetis et al. |
| 5,288,375 A | 2/1994 | Logothetis et al. |
| 5,672,811 A | 9/1997 | Kato et al. |
| 5,700,367 A | * 12/1997 | Yamada et al. ............. 205/785 |
| 5,866,799 A | * 2/1999 | Kato et al. ................ 73/31.05 |
| 5,942,190 A | * 8/1999 | Kato et al. .................... 422/98 |
| 6,071,393 A | * 6/2000 | Oshima et al. ............. 204/425 |

FOREIGN PATENT DOCUMENTS

| JP | 2-1543 | 1/1990 | ......... G01N/27/416 |
| JP | 2-122255 | 5/1990 | ......... G01N/27/419 |
| JP | 8-271476 | 10/1996 | ......... G01N/27/416 |
| WO | 95/30146 | * 11/1995 | |

* cited by examiner

Primary Examiner—Robert J. Warden, Sr.
Assistant Examiner—Kaj K. Olsen
(74) Attorney, Agent, or Firm—Sughrue Mion, PLLC

(57) ABSTRACT

An apparatus and method using a two-serial space sensor (having first and second internal spaces 2,3) for accurately measuring NOx concentration in gas, e.g., exhausted from an internal combustion engine. Both NOx (nitrogen oxide) and oxygen are forced to be partially dissociated in the first space 2 to an oxygen concentration level of $2\times10^{-7}$ to $2\times10^{-10}$ atm by pumping out oxygen from the first space 2. The NOx concentration is determined based on the second current measured in the second space 4 and based on the NO dissociation percentage in the first chamber which is 0.5–50%, or preferably 2–20%. The NOx measurement accuracy is further improved when the above oxygen concentration level is maintained from $2\times10^{-8}$ to $2\times10^{-9}$ and the temperature drift of the sensor is maintained within ±5° C. under a sensor temperature range of 700–900° C.

35 Claims, 27 Drawing Sheets

THEORETICAL EXPRESSION OBTAINED ASSUMING THAT NO DOES NOT DISSOCIATE IN FIRST PASSAGE a : OXYGEN PERCENTAGE IN MEASUREMENT GAS b: NO PERCENTAGE IN MEASUREMENT GAS

---

FIRST PUMPING CELL PUMPS OUT OXYGEN FROM FIRST PASSAGE. MEASUREMENT GAS IS INTRODUCED INTO FIRST PASSAGE IN AN AMOUNT IDENTICAL TO THAT OF PUMPED-OUT OXYGEN.
STEP 101

---

OXYGEN CONTAINED IN INTRODUCED MEASUREMENT GAS IS PUMPED OUT FROM FIRST PASSAGE. MEASUREMENT GAS IS AGAIN INTRODUCED INTO FIRST PASSAGE IN AN AMOUNT IDENTICAL TO THAT OF THE PUMPED-OUT OXYGEN.
STEP 102

---

STEPS 101 AND 102 ARE REPEATED UNTIL THE CONCENTRATION OF OXYGEN CONTAINED IN GAS INTRODUCED INTO SECOND PASSAGE ACHIEVES AN OXYGEN CONCENTRATION ($\cong$ 0%) CORRESPONDING TO SET Vs (TARGET VALUE FOR CONTROL).
STEP 103

---

ACCORDINGLY, NO PERCENTAGE IN GAS DIFFUSING INTO SECOND PASSAGE IS REPRESENTED BY THE FOLLOWING EXPRESSION:
NO PERCENTAGE
$= b + ab + a^2 b + \ldots + a^n b$
$= b(a^n - 1)/(a - 1)$
$= b/(1 - a)$ $(n \rightarrow \infty, 0 \leq a < 1)$
STEP 104

---

THUS, THE RELATIONSHIP BETWEEN THE CONCENTRATION OF OXYGEN CONTAINED IN MEASUREMENT GAS AND NO GAIN IS REPRESENTED BY THE FOLLOWING THEORETICAL EXPRESSION:
NO GAIN (ppm/$\mu$A) (THEORETICAL EXPRESSION)
$= \text{GAIN}_0 \times (1 - O_2 (\%)/100)$
WHERE
$\text{GAIN}_0$ : NO GAIN WHEN THE CONCENTRATION OF OXYGEN CONTAINED IN MEASUREMENT GAS IS 0%
STEP 105

FIG. 16

EXPERIMENTAL EXPRESSION AS OBTAINED UNDER CONDITION THAT NO
DISSOCIATES IN FIRST PASSAGE
a : OXYGEN PERCENTAGE IN MEASUREMENT GAS
b: NO PERCENTAGE IN MEASUREMENT GAS
PERCENTAGE OF DISSOCIATION: NO PERCENTAGE CAUSED TO
         DISSOCIATE IN FIRST PASSAGE

FIRST PUMPING CELL PUMPS OUT OXYGEN FROM FIRST PASSAGE.
MEASUREMENT GAS IS INTRODUCED INTO FIRST PASSAGE IN AN AMOUNT
IDENTICAL TO THAT OF PUMPED-OUT OXYGEN. AT THIS TIME, NO
DISSOCIATES IN FIRST PASSAGE
STEP 201

OXYGEN CONTAINED IN INTRODUCED MEASUREMENT GAS IS PUMPED
OUT FROM FIRST PASSAGE. MEASUREMENT GAS IS AGAIN INTRODUCED
INTO FIRST PASSAGE IN AN AMOUNT IDENTICAL TO THAT OF PUMPED-OUT OXYGEN.
STEP 202

STEPS 201 AND 202 ARE REPEATED UNTIL THE CONCENTRATION
OF OXYGEN CONTAINED IN GAS INTRODUCED INTO SECOND PASSAGE
ACHIEVES AN OXYGEN CONCENTRATION ($\cong$ 0%) CORRESPONDING TO SET Vs
(TARGET VALUE FOR CONTROL).
STEP 203

ACCORDINGLY, NO PERCENTAGE IN GAS DIFFUSING INTO SECOND
PASSAGE IS REPRESENTED BY THE FOLLOWING EXPRESSION:
NO PERCENTAGE
$= b' + ab' + a^2 b' + \ldots + a^n b'$
$= b' (a^n - 1) / (a - 1)$
$= b' / (1 - a)$
$\{n \rightarrow \infty, 0 \leq a < 1, b' = b (1 - (\text{PERCENTAGE OF DISSOCIATION}) / 100\}$
STEP 204

THUS, THE RELATIONSHIP BETWEEN THE CONCENTRATION OF
OXYGEN CONTAINED IN MEASUREMENT GAS AND NO GAIN IS REPRESENTED
BY THE FOLLOWING EXPERIMENTAL EXPRESSION:
NO GAIN (ppm/$\mu$A) (EXPERIMENTAL EXPRESSION)
$= \text{GAIN}_0 \div \{1 - (\text{PERCENTAGE OF DISSOCIATION} / 100) \times (1 - O_2 (\%) / 100)\}$
WHERE
$\text{GAIN}_0$ : NO GAIN WHEN THE CONCENTRATION OF OXYGEN CONTAINED
IN MEASUREMENT GAS IS 0%
ALSO
NO GAIN (ppm/$\mu$A) (EXPERIMENTAL EXPRESSION)
$= (\text{THEORETICAL NO GAIN (ppm/}\mu\text{A)}) \div \{1 - (\text{PERCENTAGE OF DISSOCIATION}) / 100\}$
STEP 205

METHOD FOR MEASURING NOX CONCENTRATION AND NOX CONCENTRATION SENSOR

FIELD OF THE INVENTION

The present invention relates to a method for measuring the concentration of NOx in a gas to be measured (hereinafter referred to as a measurement gas), such as exhaust gas emitted from combustion equipment or an internal combustion engine, as well as to an NOx concentration sensor.

Also, the present invention relates to an NOx concentration sensor for measuring the concentration of NOx in exhaust gas emitted from an internal combustion engine used in transportation equipment such as an automobile, ship, or an airplane, or industrial equipment such as a boiler, as well as to an apparatus and a method for measuring NOx concentration.

BACKGROUND OF THE INVENTION

Conventionally, a method has been proposed for measuring NOx concentration using an NOx concentration sensor including two measurement spaces and two oxygen ion pumping cells (hereinafter referred to as pumping cells). The conventional method includes the steps of: pumping out oxygen from one measurement space by means of a first pumping cell to an extent so as not to cause dissociation of NO; causing NO to completely dissociate in the other measurement space by means of a second pumping cell; and determining NOx concentration based on a pumping current induced by oxygen ions generated by dissociation of NO.

For example, Japanese Patent Application Laid-Open (Kokai) No. 2-1543 proposes a method for measuring the concentration of NOx, typically nitrogen monoxide (NO), contained in exhaust gas, using an NOx concentration sensor composed of two measurement spaces, each of which is equipped with a pumping cell. The method includes the steps of: pumping out only oxygen from one measurement space to an extent so as not to cause dissociation of NO; measuring a current, Ip1, flowing through a pumping cell (hereinafter referred to as a pumping current) associated with the measurement space; causing $O_2$ and NO to dissociate in the second measurement space; pumping out, from the second measurement space, oxygen generated by dissociation of $O_2$ and NO; measuring a pumping current, Ip2, flowing through the second pumping cell; and determining NOx concentration based on the difference between the pumping currents (Ip2–Ip1).

Japanese Patent Application Laid-Open (Kokai) No. 2 122255 proposes a method for measuring the concentration of a certain gas component contained in a mixed gas which contains an oxygen compound other than the gas component to be measured. The method includes the steps of: causing dissociation of the oxygen compound having a dissociation voltage lower than that of the gas component to be measured, by applying a certain fixed voltage (which does not cause dissociation of the gas component to be measured) to a first pumping cell; pumping out oxygen generated by dissociation of the oxygen compound; causing dissociation of the gas component to be measured by applying a certain voltage to a second pumping cell; detecting the amount of oxygen generated by dissociation of the gas component to be measured in terms of a second pumping current, Ip2; and determining the concentration of the gas component to be measured based on the second pumping current Ip2.

Japanese Patent Application Laid-Open (Kokai) No. 8 271476 proposes an improvement in the above-described method for measuring NOx concentration. The method includes the steps of: eliminating excess oxygen from a first space by controlling the amount of oxygen contained in the first space so as not to substantially affect the measurement of NOx concentration and so as not to cause substantial dissociation of NO; causing dissociation of NO in a second space; and determining NOx concentration based on a pumping current, Ip2, induced by oxygen generated by dissociation of NO.

The above-described methods have been developed in order to measure the concentration of NOx, for example, in an automobile exhaust gas. However, recently, there has arisen a need for measuring the concentration of NOx in a catalytically purified exhaust gas, in order to verify the purification performance of an exhaust gas purification catalyst. In this case, the accuracy required for measuring NOx concentration is not greater than ± several tens of ppm with respect to several hundreds of ppm in NOx concentration. The above-described methods fail to sufficiently satisfy this accuracy requirement and thus there is a need for further improvement.

The method for measuring NOx concentration using the aforementioned NOx concentration sensor significantly depends on oxygen concentration and temperature, and therefore it is difficult to accurately measure the NOx concentration.

In the NOx sensor proposed in the above-mentioned Japanese Patent Application Laid-Open (Kokai) No. 2-1543, the first pumping current Ip1 is relatively strong. Thus, the differential pumping current (Ip2–Ip1) is considerably influenced by variation of the first pumping current Ip1. Therefore, due to variation among sensors and temperature, measurement accuracy is impaired.

In the above method described in Japanese Patent Application Laid-Open (Kokai) No. 8-271476, oxygen in the first space is held at a partial pressure of $10^{-4}$ to $10^{-6}$ atm so as not to cause dissociation of NO within the first space. Thus, a considerable amount of oxygen is introduced into the second space. The relatively large amount of oxygen present within the second space hinders sufficient dissociation of NO within the second space. Also, the absolute quantity of variation in the oxygen concentration of gas introduced into the second space increases. As a result, an electric signal issued by the second pumping cell includes a measurement error, thus causing a failure to attain the required measurement accuracy.

SUMMARY OF THE INVENTION

The present invention has been achieved in view of the above problems of the prior art. It is therefore an object of the present invention to provide a method capable of accurately measuring NOx concentration, as well as an NOx concentration sensor capable of accurately measuring NOx concentration.

Nitrogen monoxide (NO) is dominant among NOx contained, for example, in an automobile exhaust gas. In other words, the content of NOx species other than NO, that is, the content of $N_2O$ and $NO_2$, is very low. Therefore, the following description relates to the measurement of NO concentration. The term "NOx concentration" substantially means "NO concentration".

The above object of the present invention has been achieved by providing a two-serial-space NOx concentration sensor comprising a measurement gas space (ambient atmosphere to be measured) in series communication with a first internal space a second internal space. A measurement gas is introduced from the measurement gas space into the first space and then into the second space.

In the NOx concentration sensor, by activating a first pumping cell, a portion of oxygen ($O_2$) and nitrogen monoxide (NO) contained in the first space dissociates to generate oxygen ions ($O^{2-}$). The thus-generated oxygen ions are transferred (pumped out) into the measurement gas space. By contrast, oxygen can also be pumped into the first space from the measurement gas space. By activating a second pumping cell, residual $O_2$ and NO contained in gas diffusing within the second space dissociate to generate oxygen ions, which are also removed by pumping. The first pumping cell and the second pumping cell may each comprise a solid electrolyte substrate and a pair of porous electrodes disposed on opposite sides or a single side of the substrate. By applying a predetermined voltage between the porous electrodes, oxygen can be transferred from one of the porous electrodes to the other.

To achieve the above object, a first mode of a first aspect of the present invention provides a method for measuring NOx concentration using a two-serial-space NOx concentration sensor. The sensor includes a first pumping cell and a second pumping cell each comprising a solid electrolyte. In the sensor, a measurement gas space, a first space, and a second space communicate in series with each other. The method comprises the steps of: pumping out oxygen from the first space into, for example, the measurement gas space, or pumping oxygen into the first space from, for example, the measurement gas space by action of the first pumping cell so that the oxygen concentration in the vicinity of a gas inlet of the second space becomes such that a portion of NO in the first space dissociates; dissociating residual NO and $O_2$ in gas introduced into the second space from the first space by action of the second pumping cell; pumping out oxygen ions generated by dissociation of NO and $O_2$ from the second space by action of the second pumping cell; and determining the concentration of NOx in the measurement gas based on signals (for example, pumping currents) issued from the first and second pumping cells.

Problems Solved by the Invention

FIG. 1 shows an NOx concentration sensor in accordance with the present invention. The measurement gas is introduced into the first space from the measurement gas space. The first pumping cell is operated so that the oxygen concentration in the vicinity of the gas inlet of the second space becomes such that a portion of NO in the first space dissociates. In the present invention, the degree of dissociation of NO in the first space is represented by the dissociation percentage α (%).

As a result of the above-mentioned control of oxygen concentration in the vicinity of the gas inlet of the second space, the oxygen concentration of the second space decreases, thereby eliminating a hindrance to dissociation of NO which would otherwise result from the presence of oxygen. As a result, NO dissociates sufficiently by action of the second pumping cell, so that a signal associated with the dissociation of NO and issuing from the second pumping cell can be obtained with good sensitivity.

In the present invention, the oxygen concentration of the measurement gas introduced into the second space from the first space is decreased such that a portion of No in the first space dissociates. Accordingly, the magnitude of the Ip2offset signal associated with oxygen concentration and issuing from the second pumping cell becomes low. Furthermore, the extent of variation in Ip2offset becomes small. Thus, Ip2offset less strongly affects the signal Ip2–Ip2offset, associated with the quantity of NO dissociated and issuing from the second pumping cell, to thereby provide improved accuracy in measuring NO concentration.

In the present invention, NO in the measurement gas dissociates within the first space to a predetermined degree (a predetermined dissociation percentage α). Furthermore, residual NO dissociates within the second space. Accordingly, as described below in relation to an eighth mode of the first aspect of the invention, the concentration of NO in the measurement gas can be determined based on the NO dissociation percentage in the first space and the quantity of NO dissociated in the second space.

Accordingly, the concentration of NO in the measurement gas can be determined based on a signal (for example, the first pumping current) associated with the dissociation of NO within the first space and issuing from the first pumping cell and a signal (for example, the second pumping current) associated with the dissociation of NO within the second space and issuing from the second pumping cell.

According to a second mode of the first aspect of the present invention, in the method for measuring NOx concentration as described in the first mode of the first aspect of the invention, the first space of the NOx concentration sensor communicates with the measurement gas space via a first diffusion resistance element, and the first space and the second space communicate via a second diffusion resistance element.

In the second mode of the first aspect of the invention, the measurement gas space and the first space communicate via the first diffusion resistance element. Thus, the measurement gas space is diffusion-controlled by the first diffusion resistance element. Thus, the measurement gas introduced into the first space from the measurement gas space is diffusion-controlled by the first diffusion resistance element. Through this diffusion control, the quantities of oxygen and NO introduced into the first space are limited. Accordingly, even when a voltage is applied between the electrodes of the first pumping cell, the first pumping current does not flow in excess of a certain limiting value.

Similarly, the first space and the second space communicate via the second diffusion resistance element. Accordingly, the measurement gas introduced into the second space is diffusion-controlled by the second diffusion resistance element. Through this diffusion control, the quantities of oxygen and NO introduced into the first space are limited. Accordingly, even when a voltage is applied between the electrodes of the second pumping cell, the second pumping current does not flow in excess of a certain limiting value.

The above-mentioned sensor having diffusion resistance elements is called a limit-current-type sensor and can obtain the concentration of oxygen or NO contained in a measurement gas stably and accurately. This is because a limit current can be obtained according to the concentration of oxygen or NO in the measurement gas.

According to a third mode of the first aspect of the present invention, in the method for measuring NOx concentration as described in the first or second mode of the first aspect of the invention, an oxygen-concentration-measuring cell for detecting the concentration of oxygen in gas introduced into the second space of the NOx concentration sensor is disposed in the vicinity of the gas inlet of the second space.

The third mode of the first aspect of the invention provides a method for detecting oxygen concentration in the vicinity of the gas inlet of the second space. Specifically, the oxygen-concentration-measuring cell is disposed in the vicinity of the gas inlet of the second space.

By detecting the oxygen concentration in the vicinity of the gas inlet of the second space by means of the oxygenconcentration-measuring cell, even when the distribution of oxygen concentration within the first space varies greatly, the oxygen concentration of the measurement gas introduced into the second space can be accurately controlled.

The oxygen-concentration-measuring cell can assume the form of an oxygen concentration cell, which generates an electromotive force according to an oxygen concentration differential. The oxygen-concentration-measuring cell may be composed of, for example, a solid electrolyte substrate and a pair of porous electrodes disposed on opposite sides of the substrate. In this case, one of the electrodes is disposed so as to contact the measurement gas, whereas the other electrode is disposed so as to contact a reference gas. As a result, an electromotive force is generated depending on the oxygen concentration differential between the electrodes. Based on the generated electromotive force (Vsm), the oxygen concentration on the measurement gas side of the cell can be determined.

According to a fourth mode of the first aspect of the present invention, in the method for measuring NOx concentration as described in any of the first through third modes of the first aspect of the invention, the first pumping cell is controlled based on a signal issuing from the oxygen-concentration-measuring cell for detecting oxygen concentration in the vicinity of the gas inlet of the second space of the NOx concentration sensor.

The fourth mode of the first aspect of the invention provides a method for controlling the first pumping cell. Specifically, the first pumping cell is controlled based on a signal issuing from the oxygen-concentration-measuring cell.

As mentioned above in relation to the third mode of the first aspect of the invention, a signal (for example, voltage Vsm) issuing from the oxygen-concentration-measuring cell indicates the oxygen concentration as detected in the vicinity of the gas inlet of the second space. Thus, the first pumping cell is controlled such that Vsm approaches a predetermined target value, namely, such that Vsm achieves a target voltage Vs, thereby controlling the quantity of oxygen that is pumped out from or pumped into the first space. As a result, oxygen concentration in the vicinity of the gas inlet of the second space can be controlled to a desired value, which corresponds to the target voltage Vs.

According to a fifth mode of the first aspect of the present invention, in the method for measuring NOx concentration as described in any of the first through fourth modes of the first aspect of the invention, a target value of the oxygen concentration in the vicinity of the gas inlet of the second space is set to a value not higher than $2 \times 10^{-7}$ atm in terms of oxygen partial pressure.

The fifth mode of the first aspect of the invention specifies a target value of the oxygen concentration in the vicinity of the gas inlet of the second space.

Specifically, the target oxygen concentration in the vicinity of the gas inlet of the second space is set to a partial pressure of oxygen of not higher than $2 \times 10^{-7}$ atm, but higher than $2 \times 10^{-10}$ atm, which is a sufficiently low level to cause partial dissociation of NO in the first space.

Accordingly, as described above in relation to the first mode of the first aspect of the invention, the oxygen concentration of the second space is sufficiently decreased, thereby decreasing an offset component of the second pumping current and thus enabling accurate measurement of NO concentration. The above-mentioned target oxygen concentration is more preferably set to a value of from $2 \times 10^{-8}$ to $2 \times 10^{-9}$ atm in terms of an oxygen partial pressure.

According to a sixth mode of the first aspect of the present invention, in the method for measuring NOx concentration as described in any of the first through fifth modes of the first aspect of the invention, the NO dissociation percentage in the first space is not lower than 0.5%.

The sixth mode of the first aspect of the invention specifies, in terms of the degree of dissociation of NO (dissociation percentage $\alpha$), that the oxygen concentration in the vicinity of the gas inlet of the second space is decreased such that a portion of NO in the first space dissociates.

Specifically, oxygen concentration in the vicinity of the gas inlet of the second space is decreased such that the NO dissociation percentage in the first space becomes not lower than 0.5%. As a result, as described above in relation to the first mode of the first aspect of the invention, the oxygen concentration of the second space is decreased to thereby improve accuracy in measuring NO concentration.

According to a seventh mode of the first aspect of the present invention, in the method for measuring NOx concentration as described in any of the first through sixth modes of the first aspect of the invention, the NO dissociation percentage in the first space is 1% to 50%.

The seventh mode of the first aspect of the invention specifies a more preferable dissociation percentage range. Specifically, when the NO dissociation percentage is not lower than 1%, as described above in relation to the first mode of the first aspect of the invention, the oxygen concentration of the second space is further decreased to thereby improve accuracy in measuring NO concentration.

When the NO dissociation percentage is in excess of 50%, an offset component of the second pumping current is limited to a low level; however, the NO dissociation percentage varies greatly with a variation in the oxygen concentration and temperature of the measurement gas space. Thus, measurement accuracy deteriorates greatly where environmental conditions vary significantly. More preferably, the NO dissociation percentage is 2% to 20%.

According to an eighth mode of the first aspect of the present invention, in the method for measuring NOx concentration as described in any of the first through seventh modes of the first aspect of the invention, the concentration of NOx in the measurement gas is calculated based on signals corresponding to the NO dissociation percentage in the first space and the quantity of NO dissociated in the second space.

The eighth mode of the first aspect of the invention specifies a method for determining the concentration of NOx in the measurement gas. The NOx concentration is calculated based on a signal issuing from the first pumping cell (for example, the first pumping current) and a signal issuing from the second pumping cell (for example, the second pumping current).

The operation of the first pumping cell causes NO in the first space to dissociate to a certain degree (at a certain dissociation percentage $\alpha$). Accordingly, a signal issuing from the first pumping cell corresponds to the oxygen concentration of the measurement gas and the NO dissociation percentage in the first space. Also, operation of the second pumping cell causes residual NO, namely, NO which has not dissociated in the first space and which has been introduced into the second space, to dissociate in the second space. Accordingly, a signal issuing from the second pumping cell corresponds to the quantity of NO dissociated in the second space and the quantity of oxygen introduced into the second space.

When the NOx concentration of the measurement gas is calculated based on the above-mentioned two signals, the effect of oxygen concentration must be eliminated. For example, because the second pumping current includes an offset current induced by oxygen concentration, the offset current is preferably eliminated, as described below.

According to a ninth mode of the first aspect of the present invention, in a method for measuring NOx concentration as described in the eighth mode of the first aspect of the invention, the concentration of NOx in the measurement gas is calculated according to the following calculational expression (A1):.

NOx concentration=(Ip2−Ip2offset)×A/(1−α/100)  (A1)

where

α: NO dissociation percentage in the first space (%),
A: coefficient for converting a current signal corresponding to NOx concentration to an NOx concentration,
Ip2: current flowing through the second pumping cell,
Ip2offset: offset component of current flowing through the second pumping cell, and
NOx concentration: concentration of NOx contained in the measurement gas.

The calculational expression Al is described in detail below.

According to the present invention, the measurement gas is introduced into the first space to form a new gas which then enters the second space via a gas diffusion resistance that separates the first and second space. The operation of the first pumping cell dissociates $O_2$ to a certain oxygen partial pressure level and also causes NO in the first space to partially dissociate to a certain degree (at a certain dissociation percentage α).

Operation of the second pumping cell causes the residual NO, namely, NO which has not dissociated in the first space and which has been introduced into the second space, to dissociate in the second space. Accordingly, NO concentration can be detected based on the state of dissociation of NO in the first and second spaces.

Specifically, because current flowing through the second pumping cell (the second pumping current Ip2) corresponds to the quantity of NO and the quantity of $O_2$ dissociated in the second space, the offset current Ip2offset, which corresponds to the quantity of $O_2$ dissociated in the second space, is desirably eliminated from the second pumping current Ip2. The resulting difference, Ip2−Ip2offset, corresponds to the quantity of NO dissociated in the second space.

When the NO concentration of the measurement gas is taken as 1, the NO concentration of the measurement gas introduced into the second space can be represented by "1α/100." If all of the NO introduced into the second space dissociates, then a current corresponding to the NO concentration of the measurement gas is represented by "(Ip2−Ip2offset)/(1−α/100)."

Accordingly, by multiplying the current (Ip2−Ip2offset)/(1−α/100) by a predetermined coefficient (a coefficient for converting current to NO concentration) A, the concentration of NO in the measurement gas space is obtained.

As will be later described in detail, the offset current Ip2offset appearing in the equation A1 is obtained from the first pumping current Ip1. This is because the Ip2offset can be determined by a relation (or map) pre-measured or rather predetermined with the electromotive force cell voltage Vs that represents an oxygen partial pressure level at an inlet of the second passage (or rather at an outlet of the first passage), and further because the voltage Vs can also act as a parameter functioning between the first pumping current Ip1 and the oxygen concentration level of a measurement gas of interest entering the first passage.

According to a tenth mode of the first aspect of the present invention, the method for measuring NOx concentration as described in the ninth mode of the first aspect of the invention employs an NOx concentration sensor in which the first pumping cell is controlled such that a signal issuing from the oxygen-concentration-measuring cell for detecting oxygen concentration in the vicinity of the gas inlet of the second space assumes a target value. The method comprises the steps of: calculating the concentration of oxygen in the measurement gas using a map of a previously measured relationship between current flowing through the first pumping cell and the concentration of oxygen in the measurement gas while taking the target value as a parameter; and calculating Ip2offset using a map of a previously measured relationship between Ip2offset and the concentration of oxygen in the measurement gas while taking the target value as a parameter.

The tenth mode of the first aspect of the invention provides a more specific method according to the ninth mode of the first aspect of the invention.

In order to calculate the concentration of oxygen in the measurement gas, a map showing the relationship among the target value (target voltage Vs for the oxygen-concentration-measuring cell), current flowing through the first pumping cell (the first pumping current Ip1), and the oxygen concentration of the measurement gas is experimentally prepared in advance, for example, as shown in FIG. 2. The concentration of oxygen in the measurement gas is obtained using this map, and is based on a measured value of Ip1 and a predetermined target value of Vs.

Also, for example, as shown in FIG. 3, a map showing the relationship among the target value (Vs), the offset current Ip2offset, and the oxygen concentration of the measurement gas is experimentally prepared in advance. The offset current Ip2offset is obtained using this map, and is based on a predetermined target value of Vs and the above-obtained oxygen concentration.

The offset current Ip2offset for use in the expression A1 is thus obtained. The maps shown in FIGS. 2 and 3 are in the form of a graph representing the relationship between oxygen concentration and a pumping current, but are not limited thereto. Alternatively, the maps may assume, for example, the form of an ordinary matrix table.

According to an eleventh mode of the first aspect of the present invention, the method for measuring NOx concentration as described in the ninth mode of the first aspect of the invention employs an NOx concentration sensor in which the first pumping cell is controlled such that a signal issuing from the oxygen-concentration-measuring cell for detecting oxygen concentration in the vicinity of the gas inlet of the second space assumes a target value. The method comprises the steps of: calculating the concentration of oxygen in the measurement gas using a map of a previously measured relationship between current flowing through the first pumping cell and the concentration of oxygen in the measurement gas while taking the target value as a parameter; and calculating A/(1−α/100) (hereinafter referred to as gain) using a map of a previously measured relationship between gain and the concentration of oxygen in the measurement gas while taking the target value as a parameter.

The eleventh mode of the first aspect of the invention provides a more specific method according to the ninth mode of the first aspect of the invention.

As described above in relation to the tenth mode of the first aspect of the invention, the concentration of oxygen in the measurement gas is calculated based on the first pumping current Ip1 and by using, for example, the map shown in FIG. 2. As shown in FIG. 4, a map is experimentally prepared in advance showing the relationship among the target oxygen concentration (the target voltage Vs for the oxygen-concentration-measuring cell), gain and the concentration of oxygen in the measurement gas. The gain is obtained using this map, and is based on Vs and the above-obtained oxygen concentration. Notably, the map shown in FIG. 4 may also assume the form of an ordinary matrix table as in the case of other similar maps.

The gain is thus obtained. Also, the offset current Ip2offset is obtained according to the aforementioned tenth mode of the first aspect of the invention. Furthermore, the second pumping current Ip2 is obtained by actual measurement. By substituting these values into the expression A1, the NO concentration can be obtained, or the substantial NOx concentration of the measurement gas can be obtained.

According to a first mode of a second aspect of the present invention, an NOx concentration sensor is provided which is a two-serial-space-type NOx concentration sensor comprising a first space, a second space, a first diffusion resistance element and a second diffusion resistance element. The first space is partially defined by a first pumping cell and an oxygen-concentration-measuring cell, each comprising a solid electrolyte layer and a pair of electrodes. The second space is partially defined by a second pumping cell comprising a solid electrolyte layer and a pair of electrodes. The first diffusion resistance element establishes communication between the first space and a measurement gas space. The second diffusion resistance element establishes communication between the first space and the second space. The oxygen-concentration-measuring cell is disposed in the vicinity of the second diffusion resistance element, and the sensor further comprises a measuring section (which can comprise a circuit) for measuring a first pumping current flowing through the first pumping cell, a measuring section (which can comprise a circuit) for measuring a second pumping current flowing through the second pumping cell, and a calculation section (which can comprise a circuit and/or a microprocessor and associated memory) for calculating the concentration of NOx in the measurement gas based on the first pumping current and the second pumping current.

The first mode of the second aspect of the invention specifies the structure of the NOx concentration sensor.

In the NOx concentration sensor, oxygen concentration in the vicinity of the gas inlet of the second space is measured by the oxygen-concentration-measuring cell disposed in the vicinity of the second diffusion resistance element. The first pumping cell is operated such that the thus-measured oxygen concentration assumes a predetermined value (namely, such that a portion of NO in the first space dissociates). At this time, the first pumping current and the second pumping current are measured. Based on the measured currents, the concentration of NO in the measurement gas is determined, as described in detail below.

According to a second mode of the second aspect of the present invention, in the NOx concentration sensor as described in the first mode of the second aspect of the invention, oxygen is pumped out from or pumped into the first space by means of the first pumping cell so that the oxygen concentration in the vicinity of the gas inlet of the second space becomes such that a portion of the NO contained in the first space dissociates.

The second mode of the second aspect of the invention specifies the function of the first pumping cell. By applying a voltage between the electrodes of the first pumping cell, the first pumping cell is activated so as to pump out oxygen from or pump oxygen into the first space. As a result, the oxygen concentration in the vicinity of the gas inlet of the second space is regulated such that a portion of the NO contained in the first space dissociates.

According to a third mode of the second aspect of the present invention, in the NOx concentration sensor as described in the first or second mode of the second aspect of the invention, the calculation section calculates the concentration of NOx in the measurement gas according to the following calculational expression A1:

$$\text{NOx concentration} = (Ip2 - Ip2\text{offset}) \times A / (1 - \alpha/100) \quad (A1) \text{ where}$$

α: NO dissociation percentage in the first space (%),
A: coefficient for converting a current signal corresponding to NOx concentration to an NOx concentration,
Ip2: current flowing through the second pumping cell,
Ip2offset: offset component of current flowing through the second pumping cell, and
NOx concentration: concentration of NOx in the measurement gas.

The third mode of the second aspect of the invention provides an NOx concentration sensor for implementing the method of the ninth mode of the first aspect of the invention.

Accordingly, the expression A1 has the same meaning as in the ninth mode of the first aspect of the invention.

Specifically, because the quantity "Ip2−Ip2offset" corresponds to a signal which, in turn, corresponds to the quantity of NO dissociated in the second space, a current corresponding to the concentration of NO in the measurement gas is represented by $(Ip2-Ip2\text{offset})/(1-\alpha/100)$. Accordingly, by multiplying the current $(Ip2-Ip2\text{offset})/(1-\alpha/100)$ by the conversion coefficient A, the concentration of NO in the measurement gas can be obtained.

According to a fourth mode of the second aspect of the present invention, the NOx concentration sensor as described in the third mode of the second aspect of the invention, in which the first pumping cell is controlled such that a signal issuing from the oxygen-concentration-measuring cell for detecting oxygen concentration in the vicinity of the gas inlet of the second space assumes a target value, further comprises an oxygen concentration calculation section (which may comprise a circuit and/or a microprocessor and associated memory) and an Ip2offset calculation section (which may comprise a circuit and/or a microprocessor and associated memory). The oxygen concentration calculation section calculates the concentration of oxygen in the measurement gas using a map which shows a previously measured relationship between current flowing through the first pumping cell and the concentration of oxygen in the measurement gas while taking the target value as a parameter, that is, for a certain target value. The Ip2offset calculation section calculates Ip2offset using a map which shows the previously measured relationship between Ip2offset and the concentration of oxygen in the measurement gas while taking the target value as a map parameter.

The fourth mode of the second aspect of the invention provides an NOx concentration sensor for implementing the method of the tenth mode of the first aspect of the invention.

As in the case of the tenth mode of the first aspect of the invention, the concentration of oxygen in the measurement gas is obtained using the map of FIG. 2. Based on the thus-obtained oxygen concentration, the offset current Ip2offset can be obtained using the map of FIG. 3.

According to a fifth mode of the second aspect of the present invention, the NOx concentration sensor as described in the third or fourth mode of the second aspect of the invention, in which the first pumping cell is controlled such that a signal issuing from the oxygen-concentrationmeasuring cell for detecting oxygen concentration in the vicinity of the gas inlet of the second space assumes a target value, further comprises an oxygen concentration calculation section and a gain calculation section (which may comprise a circuit and/or a microprocessor and associated memory). The oxygen concentration calculation section calculates the concentration of oxygen contained in the measurement gas using a map which shows a previously measured relationship between current flowing through the first pumping cell and the concentration of oxygen in the measurement gas while taking the target value as a parameter. The gain calculation section calculates $A/(1-\alpha/100)$ (gain) using a map which shows a previously measured relationship between the gain and the concentration of oxygen in the measurement gas while taking the target value as a parameter.

The fifth mode of the second aspect of the invention provides an NOx concentration sensor for implementing the method of the eleventh mode of the first aspect of the invention.

As in the case of the eleventh mode of the first aspect of the invention, the concentration of oxygen in the measurement gas is obtained using the map of FIG. 2. Based on the thus-obtained oxygen concentration, the gain can be obtained using the map of FIG. 4.

In measuring NOx concentration using the NOx concentration sensor described above, the sensor is preferably controlled to a predetermined temperature of 550 to 900° C. by disposing one or more heaters on a single side or on opposite sides of the sensor.

As shown in FIG. 5, the NO dissociation percentage in the first space varies with the temperature of the sensor (element temperature). Therefore, the sensor is preferably used within a temperature range such that the NO dissociation percentage does not vary greatly. In another aspect for providing accurate NOx measurement, it is important to maintain a temperature drift of the sensor within ±5° C., preferably ±2.5° C., more preferably ±1° C. This is because the sensor temperature drift varies the NO dissociation percentage and in turn affects the measurement accuracy.

In the above description of the present invention, the dissociation of NO and oxygen means the separation of NO and oxygen into simpler constituents. For example, as shown in the formulae below, nitrogen monoxide (NO) dissociates into nitrogen (molecular nitrogen $N_2$) and oxygen (molecular oxygen $O_2$), and oxygen (molecular oxygen $O_2$) dissociates into oxygen ions ($O^{2-}$).

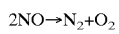

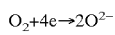

A first mode of a third aspect of the present invention has the following features. A measurement gas including $O_2$ and NOx diffuses into a first passage, which faces a first pumping cell, and then diffuses into a second passage, which faces a second pumping cell. The first pumping cell causes a portion of $O_2$ and NO contained in the gas which has diffused into the first passage to dissociate, thereby controlling the concentration of oxygen in the gas contacting the second pumping cell to as low a level as possible. The second pumping cell causes residual NO contained in the gas which has diffused into the second passage to dissociate.

The preferable range of the oxygen concentration of the gas detected at the inlet of the second passage, said gas then contacting with the second pump cell electrode, is from $2 \times 10^{-7}$ to $2 \times 10^{-10}$ atm and more preferably from $2 \times 10^{-8}$ to $2 \times 10^{-9}$ atm defined by oxygen partial pressure, according to the invention. The range is calculated from the oxygen concentration cell voltage Vs, based on the known Nernst equation. In this range of the oxygen concentration, the improved accuracy of NOx measurement is attained because of a decomposition rate or dissociation percentage a of NO in the first passage where the first pumping cell is located can become constantly stable even if a substantial decomposition of No occurs in the first passage.

In the case that the oxygen concentration measuring cell (EMF cell) has an oxygen reference electrode communicating with the atmospheric air having an oxygen partial pressure of about $2 \times 10^{-1}$ atm, the Vsm value measured at the oxygen concentration detection electrode of the cell corresponding to the above oxygen concentration range (of $2 \times 10^{-7}$ to $2 \times 10^{-10}$ atm.) is from 300 mV to 450 mV. When the oxygen concentration cell has the oxygen reference electrode communicating with a self-made oxygen reference atmosphere having about $2 \times 10^{-1}$ atm. (as the case for the embodiment later explained), the corresponding Vsm is from 350 mV to 500 mV, measuring about 50 mV higher than the above range.

A second mode of the third aspect of the present invention includes means for correcting the measurement of NOx concentration to take into account a variation in the NO dissociation percentage in the first passage with a change in the concentration of oxygen in the measurement gas. Preferably, the term $\Delta Ip2=(Ip2-Ip2offset)$ is multiplied by a predetermined coefficient, which is a function of the NO dissociation percentage in the first passage. The measurement of NOx concentration can be further corrected for other factors by multiplying the term $\Delta Ip2$ by another coefficient. The coefficient is experimentally obtained in advance and is selected according to Ip1 and/or Ip2, thereby further improving accuracy in measuring NOx concentration.

A third mode of the third aspect of the present invention includes means for correcting the measurement of NOx concentration to take into account a variation in the ratio between the concentration of NOx in the measurement gas and the concentration of NOx in the gas diffusing into the second passage caused by control of oxygen concentration by said first pumping cell.

A fourth mode of the third aspect of the present invention includes means for correcting the measurement of NOx concentration to take into account a variation in the ratio between the concentration of NOx in the measurement gas and the concentration of NOx in the gas diffusing into the second passage with a change in NO dissociation percentage in the first passage.

A first mode of a fourth aspect of the present invention provides an NOx concentration sensor comprising a first passage, a second passage, an oxygen-concentration-measuring cell, a first pumping cell and a second pumping cell. A measurement gas diffuses into the first passage via a first diffusion resistance element. In the first passage, $O_2$ and NO are partially dissociated. Gas leaving the first passage diffuses into the second passage via a second diffusion resistance element facing a downstream end portion of the first passage. In the second passage, residual NO and $O_2$ in the gas introduced from the first passage are dissociated. The oxygen-concentration-measuring cell has an electrode which is disposed downstream of the first passage and on the inlet side of or facing the second diffusion resistance element. The oxygen-concentration-measuring cell (EMF cell) measures the oxygen partial pressure by voltage developed across the oxygen concentration detection electrodes as described, for example, in U.S. Pat. No. 4,272,329 incorporated herein by reference. The first pumping cell has an electrode facing the first passage. By applying a voltage to the electrode of the first pumping cell based on the electromotive force output from the oxygen-concentration-measuring cell, the first pumping cell causes a portion of $O_2$ and NO in the first passage to dissociate. A current (first pumping current) induced by oxygen ions generated by dissociation of $O_2$ and NO flows through the first pumping cell. The second pumping cell has an electrode facing the second passage. By applying a voltage to the electrode of the second pumping cell, the second pumping cell causes residual $O_2$ and NO contained in the gas which has diffused into the second passage to dissociate. A current (second pumping current) induced by oxygen ions generated by dissociation of residual $O_2$ and NO flows through the second pumping cell.

According to a second mode of the fourth aspect of the invention, the concentration of NOx in the measurement gas is obtained based on the first pumping current flowing through the first pumping cell and the second pumping current flowing through the second pumping cell. The first pumping current includes a current component induced by oxygen ions generated by the dissociation of NO in the first passage. The second pumping current includes a current component induced by oxygen ions generated by the dissociation of NO in the second passage.

According to a third mode of the fourth aspect of the invention, the electrode of the first pumping cell extends along a gas flow within the first passage and on a solid electrolyte layer which constitutes the first pumping cell.

According to a fourth mode of the fourth aspect of the invention, the electrode of the oxygen-concentration-measuring cell is formed on a solid electrolyte layer which constitutes the oxygen-concentration-measuring cell, in such manner as to be located downstream of the first passage and in the vicinity of an inlet to or facing the second diffusion resistance element.

A first mode of a fifth aspect of the present invention has the following features. A measurement gas including $O_2$ and NOx diffuses into a first passage. A portion of the $O_2$ and NO in the gas which has diffused into the first passage is dissociated so as to control the concentration of oxygen in the gas diffusing into the second passage to as low a level as possible. Residual NO and $O_2$ contained in the gas which has diffused into the second passage are dissociated. The concentration of NOx in the measurement gas is obtained based on a first pumping current, which is induced by oxygen ions generated by the dissociation of $O_2$ and NO within the first passage, and a second pumping current, which is induced by oxygen ions generated by the dissociation of NO and $O_2$ within the second passage. According to a second mode of the fifth aspect of the invention, the concentration of NOx in the measurement gas is obtained based on the NO dissociation percentage in the first passage. According to a third mode of the fifth aspect of the invention, the concentration of NOx in the measurement gas is obtained based on the NO dissociation percentage in the first passage and the rate of variation in NO concentration due to control of the concentration of oxygen in the gas diffusing into the second passage causing a variation in the ratio between the concentration of NO in the measurement gas and the concentration of NO in the gas diffusing into the second passage. According to a fourth mode of the fifth aspect of the invention, the NO dissociation percentage in the first passage is corrected for the concentration of oxygen in the measurement gas.

A first mode of a sixth aspect of the present invention provides an apparatus for measuring NOx concentration, comprising a first passage, a second passage, an oxygen-concentration-measuring cell, a first pumping cell, a second pumping cell, first pumping cell control means and second pumping cell control means. A measurement gas diffuses into the first passage via a first diffusion resistance element. In the first passage, $O_2$ and NO partially dissociate. The gas leaving the first passage diffuses into the second passage via a second diffusion resistance element facing a downstream end portion of the first passage. In the second passage, residual NO and $O_2$ contained in the gas dissociate. The oxygen-concentration-measuring cell has an electrode which is disposed downstream of the first passage and in the vicinity of an inlet to or facing the second diffusion resistance element. The oxygen-concentration-measuring cell outputs an electromotive force by means of a concentration cell effect and according to the concentration of oxygen in the gas contacting the oxygen-concentration-measuring cell. By applying a voltage to the first pumping cell based on the electromotive force output from the oxygen-concentration-measuring cell, the first pumping cell causes a portion of $O_2$ and NO in the first passage to dissociate. A first pumping current induced by oxygen ions generated by the dissociation of $O_2$ and NO flows through the first pumping cell. By applying a voltage to the second pumping cell, the second pumping cell causes residual $O_2$ and NO in gas which has diffused into the second passage to dissociate. A second pumping current induced by oxygen ions generated by the dissociation of residual $O_2$ and NO flows through the second pumping cell. The first pumping cell control means applies a voltage to the first pumping cell such that a portion of $O_2$ and NO in the first passage dissociates. This controls the concentration of oxygen contained in the gas diffusing into the second passage to as low a level as possible. The second pumping cell control means applies a voltage to the second pumping cell such that residual NO and $O_2$ in gas which has diffused into the second passage dissociates. According to a second mode of the sixth aspect of the invention, the apparatus of the first mode of the sixth aspect of the invention further comprises means for storing the relationship between oxygen concentration and gain for NO concentration; and means for solving a relational expression between the first pumping current and oxygen concentration which includes a term whose value varies with NO concentration, as well as a relational expression between the second pumping current and NO concentration which includes a term whose value varies with oxygen concentration, based on the measured first pumping current, the measured second pumping current and the stored relationship between oxygen concentration and gain for NO concentration.

A seventh aspect of the present invention provides a method for measuring the concentration of a certain gas component contained in a measurement gas, comprising the steps of: measuring an oxygen ion pump current which flows when an oxygen ion pump means is operated so as to dissociate a portion of the certain gas component in a measurement gas which has been introduced into a passage; measuring an oxygen ion pump current which flows when the oxygen ion pump means is operated so as to dissociate the residual certain gas component in the gas which has undergone dissociation of a portion of the certain gas component; and determining the concentration of the certain gas component in the measurement gas based on the two measured oxygen ion pump currents.

An eighth aspect of the present invention provides an apparatus for measuring the concentration of a certain gas component in a measurement gas, comprising: oxygen ion pump means faces a passage into which the measurement gas is introduced and whose operation for pumping out oxygen from the passage causes a pump current to flow; means for measuring an oxygen ion pump current which flows when the oxygen ion pump means is operated so as to dissociate a portion of the certain gas component in the measurement gas that has been introduced into the passage; means for measuring an oxygen ion pump current which flows when the oxygen ion pump means is operated so as to dissociate the residual certain gas component contained in the gas in which a portion of the certain gas component has been dissociated; and means for determining the concentration of the certain gas component in the measurement gas based on the two measured oxygen ion pump currents. In the seventh and eight aspects of the invention, the certain gas component is preferably NOx.

In the above-described aspects of the present invention (particularly the third through sixth aspects), oxygen concentration in the first passage is controlled to as low a level as possible so long as a portion of the NO contained in the measurement gas dissociates in the first passage. This decreases the concentration of oxygen in gas diffusing into the second passage to as low a level as possible, thereby decreasing the oxygen concentration dependence and temperature dependence of the NOx concentration measurement. Residual NO is dissociated in the second passage. Based on current which is generated by the dissociation of residual NO, the NOx concentration is calculated taking into account the NO dissociation percentage in the first passage. Thus, the concentration of NOx in the measurement gas can be obtained very accurately.

A first mode of a ninth aspect of the present invention provides a method for measuring the concentration of NOx in a measurement gas using an NOx concentration sensor having at least two spaces into which the measurement gas is introduced. The method comprises the steps of: introducing the measurement gas into at least a first space and causing dissociation of a portion of NO and $O_2$ in the first space; introducing the gas from the first space into a second space and causing dissociation of residual NO and $O_2$ in the second space; and determining the concentration of NOx in the measurement gas based on the quantity of NO and $O_2$ dissociated in the first and second spaces.

According to a second mode of the ninth aspect of the invention, the concentration of NOx in the measurement gas is obtained according to the following equations:

$\alpha = f(Ip1)$, $\beta = g(Ip1)$, and $(1-\alpha/100) \times (NOx\ concentration) + \beta = Ip2$, where α: NO dissociation percentage in the first space (%), β: offset component of second pumping current corresponding to the quantity of oxygen dissociated in the second space, NOx concentration: concentration of NOx in the measurement gas, Ip1: first pumping current flowing through the first pumping cell, Ip2: second pumping current flowing through the second pumping cell, f: symbol expressing a functional relationship between α and Ip1, and g: symbol expressing a functional relationship between β and Ip1.

In order to establish the correlation between the unit quantity of Ip2 and that of NOx concentration, the right-hand member of the above third expression may be multiplied by coefficient A. Notably, Ip2 may be adjusted in order to establish the correlation between the unit quantity of Ip2 and that of NOx concentration. The functions f and g can be experimentally obtained. In a simple method, α and β can be obtained from Ip1 using a map.

According to a third mode of the ninth aspect of the invention, by using a previously prepared three-dimensional map showing the relationship among the first pumping current, the second pumping current and the concentration of NOx in the measurement gas, the concentration of NOx in the measurement gas is obtained based on a measured first pumping current and a measured second pumping current.

The present invention will next be described with reference to the drawings, while using, as an example, an NOx concentration sensor in which a measurement gas is diffused into a first internal passage; oxygen is pumped out by means of a first pumping cell from the first passage; gas having a controlled oxygen concentration is diffused into a second passage from the first passage; and a second pumping cell which causes NOx in the gas to dissociate. The drawings are referenced for explanation, and should not be construed as limiting the invention. In the description below, NOx concentration=(gain for NOx concentration)×(variation in output from NOx concentration sensor). Notably, in the present invention, the NOx concentration gain is the variation in NOx concentration corresponding to a constant variation in sensor output (ppm/μA), namely, the reciprocal of sensor sensitivity.

First, the partial dissociation of NO in the first passage will be described. As shown in FIG. 14, an electrode 6b of a first pumping cell 6 is formed along the direction of measurement gas flow. The first pumping cell 6 undergoes feedback control based on an output from an oxygen concentration detection electrode 7a. As gas introduced into a first passage 2 diffuses, oxygen contained in the gas is gradually pumped out. Consequently, the oxygen concentration in the first passage 2 gradually decreases toward the downstream end of the first passage 2. The oxygen concentration detection electrode 7a detects an average oxygen concentration in a local space which faces the electrode 7a. That is, the oxygen concentration detection electrode 7a detects and outputs a local oxygen concentration in the vicinity of the center of the electrode 7a. Accordingly, the first pumping cell 6 substantially controls the oxygen concentration in the gas diffusing into a second passage such that the local oxygen concentration detected in the vicinity of the center of the oxygen concentration detection electrode 7a assumes a target oxygen concentration. As a result, the oxygen concentration of the local space in the vicinity of the center of the oxygen concentration detection electrode 7a agrees with the target oxygen concentration, whereas the oxygen concentration of the space located downstream of the central portion of the electrode 7a is lower than the target oxygen concentration. In the local space of lower oxygen concentration NO is more likely to dissociate, as seen from the formula "$2NO \rightarrow N_2 + O_2$".

The concentration of oxygen in the gas diffusing into the second passage is controlled so as to become constant regardless of the concentration of oxygen in the measurement gas. Accordingly, the oxygen concentration gradient in the first passage 2 becomes steeper in the case of a high oxygen content in the measurement gas than that in the case of a measurement gas having a low oxygen content. As a result, a local space having a low oxygen concentration emerges within the first passage 2. Thus, the NO dissociation percentage in the first passage 2 varies according to the concentration of oxygen in the measurement gas.

First, based on the assumption that NO does not dissociate in the first passage, a theoretical expression for NOx concentration gain will be described. When the measurement gas is introduced into the NOx concentration sensor, the composition of gas diffusing into the second passage gradually varies and reaches a steady state. This is illustrated in FIG. 15. FIG. 16 shows a process of obtaining a gain for NOx concentration in the manner of a geometrical series in the case of FIG. 15.

As shown in FIGS. 15 and 16, a measurement gas which contains oxygen in a proportion of a and NO in a proportion of b is introduced into the NOx concentration sensor. Oxygen is pumped out from the first passage such that the concentration of oxygen in gas diffusing into the second passage approaches 0%. As a result, the measurement gas diffuses into the first passage at the same rate as that of the pumped-out oxygen. Thus, the gas diffusing into the second passage contains NO in a proportion of "a+ab" (steps 101 and 102). The step of pumping out oxygen is repeated until the concentration of oxygen in the gas diffusing into the second passage reaches a target value (step 103). As a result of repeating steps 101 and 102, finally, the proportion of NO contained in the gas diffusing into the second passage becomes b/(1−a) (step 104). Because the NO gain is proportional to the reciprocal of the proportion of NO in the gas diffusing into the second passage, the theoretical expression "NO gain [theoretical value]=$gain_0 \times \{1-O_2[\%]/100\}$" is deduced (step 105). As seen from the theoretical expression, the NO gain varies with the concentration of oxygen in the measurement gas.

Next, a theoretical expression for NO gain in the case where NO dissociates in the first passage will be described with reference to FIG. 17. Oxygen is pumped out from the first passage, and NO dissociates in the first passage (step 201). Thus, with b'=b{1−(NO dissociation percentage [%] in first passage)/100}, the proportion of NO contained in the gas diffusing into the second passage is represented by "b'+ab'". As a result of repeating steps 201 and 202, finally, the proportion of NO in the gas diffusing into the second passage becomes b'/(1−a) (steps 203 and 204). Thus, the theoretical expression "NO gain"=$gain_0/\{1-(\text{NO dissociation percentage [\%] in first passage})/100\} \times \{1-O_2[\%]/100\}$ is deduced (step 205). As seen from the theoretical expression, the NO gain also varies with the NO dissociation percentage in the first passage.

As seen from the theoretical expressions obtained in steps 105 and 205, the NO gain [no dissociation] in the case where No does not dissociate in the first passage and the NO gain [dissociation] in the case where NO dissociates in the first passage have the following relationship: NO gain [dissociation]=NO gain [no dissociation]/{1−(NO dissociation percentage [%] in the first passage)/100}. Thus, based on the NO dissociation percentage in the first passage at a certain measurement gas oxygen concentration and the NO gain [no dissociation] at that oxygen concentration, the NO gain [dissociation] at a certain measurement gas oxygen concentration is obtained.

Next, a preferred embodiment of the present invention will be described. Specifically, a method for measuring NOx concentration using an NOx concentration sensor as shown in FIGS. 18 and 19 will be described. FIG. 20 shows where the plane of FIGS. 18 and 19 is located within a sensor element. The NOx concentration sensor of FIGS. 18 and 19 has a first pumping cell 6, an oxygen-concentration-measuring cell 7 and a second pumping cell 8 arranged in layers. A first passage 2 is provided so as to face the first pumping cell 6 and the oxygen-concentration-measuring cell 7. A second passage 4 is provided so as to face the second pumping cell 8. A first porous diffusion hole (resistance element) 1 is provided at an inlet to the first passage 2. A second porous diffusion hole (resistance element) 3 is provided at an inlet to the second passage 4. The first and second pumping cells 6 and 8, respectively, are each composed of an oxygen-ion conductive solid electrolyte layer and a pair of electrodes formed on the solid electrolyte layer. The oxygen-concentration-measuring cell 7 is an oxygen concentration cell for generating an electromotive force Vsm by means of a concentration cell effect (hereinafter simply referred to as electromotive Vsm) depending on the concentration of oxygen (partial pressure of oxygen) in the gas diffusing into the second passage 4.

External circuits serving as control mean 20 and 21 are connected to the NOx concentration sensor in order to control the first and second pumping cells 6 and 8, respectively. Electrodes 6b and 7a are electrically connected, and their point of connection is grounded via a resistance. The electrode 7b is electrically connected to the inverted input terminal (−) of a differential amplifier 20a. A reference voltage Vs is input to the uninverted input terminal (+) of the differential amplifier 20a. In order to control the concentration of oxygen in the gas diffusing into the second passage 4 to a target value corresponding to the reference voltage Vs, the output the differential amplifier 20a reversibly controls a first pumping current Ip1. Thus, the first pumping current Ip1 flows between the electrodes 6a and 6b such that the electromotive force Vsm generated between the electrodes 7a and 7b assumes the reference voltage Vs. As a result, oxygen is pumped out from or pumped into the first passage 2. Meanwhile, a constant voltage Vp2 is applied between electrodes 8a and 8b, causing a second pumping current Ip2 to flow between the electrodes 8a and 8b. Reference oxygen generation means 22 supplies a small current between the electrodes 7a and 7b so as to pump out oxygen toward the electrode 7b side, thereby forming a reference oxygen space around the electrode 7b. In order to operate the NOx concentration sensor at an appropriate temperature, one or more unillustrated heaters are provided on or attached to a single side or opposite sides of a sensor element.

Control by First Pumping Cell Control Means 20

The reference voltage Vs is set, which is a target value of control for the electromotive force Vsm generated between the electrodes 7a and 7b of the oxygen-concentration-measuring cell 7. However, Vs is set such that a portion of NO and $O_2$ in the first passage 2 dissociates so as to decrease the concentration of oxygen in the gas diffusing into the second passage 4 to as low a level as possible. As a result, an offset Ip2offset of the second pumping current Ip2 can be decreased as much as possible. Ip2offset, which is described below, is a value corresponding to the concentration of oxygen contained in the gas diffusing into the second passage 4, and hereinafter may be referred to as $Ip2_0$.

The first pumping cell 6 is subjected to feedback control such that the electromotive force Vsm becomes equal to the reference voltage Vs.

Control by Second Pumping Cell Control Means 21

The voltage Vp2 is applied between the electrodes 8a and 8b of the second pumping cell 8 such that all of the NO diffusing into the second passage 4 dissociates.

According to a preferred embodiment of the method for measuring NOx of the present invention, while the concentration of oxygen in the measurement gas is varied, the first pumping current and the NO dissociation percentage are measured. The thus-measured relationship is stored in the form of a map or a relational expression in, for example, a memory provided in the NOx concentration sensor. During operation of the sensor, the first pumping current is periodically measured, and an NO dissociation percentage is calculated which corresponds to an oxygen concentration at the measured first pumping current.

Other factors which would otherwise influence the measurement of NOx concentration can be compensated for by experimentally obtaining a coefficient for $\Delta Ip2$ in advance, to thereby obtain sufficient measurement accuracy.

The preferred embodiment of the method for measuring NOx concentration of the present invention takes into account both the dissociation of NO and an increase in NOx concentration caused by pumping out oxygen from the first passage. This preferred embodiment will next be described in detail.

A measurement gas including NO and oxygen diffuses into the first passage 2.

As the measurement gas diffuses within the first passage 2, $O_2$ contained in the gas dissociates, particularly above the electrode 6b. Oxygen ions generated by the dissociation of $O_2$ are pumped out toward the electrode 6 a side; consequently, oxygen concentration in the first passage 2 decreases (see FIG. 14). Also, a portion of the NO dissociates in the first passage 2. Oxygen ions generated by the dissociation of $O_2$ and by the dissociation of NO cause a first pumping current Ip1 to flow between the electrodes 6a and 6b of the first pumping cell 6, to which the voltage Vp1 is applied. As the concentration of oxygen in the measurement gas with respect to a target oxygen concentration corresponding to Vs increases, the NO concentration in the first passage 2 increases because more oxygen is pumped out from the first passage 2. Thus, as the concentration of oxygen in the measurement gas increases, the concentration of NO contained in the gas diffusing into the second passage 4 increases.

Oxygen concentration is sufficiently decreased by action of the first pumping cell, and a gas which contains residual NO diffuses into the second passage 4.

Residual $O_2$ and NO contained in the gas which has diffused into the second passage 4 dissociate. Oxygen ions generated by the dissociation of $O_2$ and by the dissociation of NO cause a second pumping current Ip2 to flow between the electrodes 8a and 8b of the second pumping cell 8, to which a the constant voltage Vp2 is applied.

The reason for causing a portion of NO in the first passage to dissociate will next be described. In order to the decrease oxygen concentration dependence and temperature dependence of the NOx concentration measurement so as to provide a high degree of measurement accuracy, the concentration of oxygen in the gas diffusing into the second passage must be considerably decreased. To this end, in the present invention, oxygen is sufficiently pumped out from the first passage such that a portion of NO in the first passage dissociates. By performing such oxygen concentration control in the vicinity of the second porous diffusion hole, a region having an oxygen concentration lower than a target oxygen concentration emerges in the first passage. In this region, the dissociation of NO is particularly accelerated.

The calculation of NOx concentration based on the first and second pumping currents Ip1 and Ip2, respectively, will next be described. The method for calculating NOx concentration will be schematically described using a number-of-molecules model. First, it is assumed that NO does not dissociate in the first passage. Here, the measurement gas (the total number of molecules per unit volume=10,000) has the following composition: the number of NO molecules= 10; the number of $O_2$ molecules=1,000; and the number of $N_2$ molecules=8,990. When the number of $O_2$ molecules in the gas diffusing into the second passage is taken as 1, the number of NO molecules in the gas diffusing into the second passage is calculated as 10×9,999/9,000 at steady state. Next is the case where the measurement gas has the following composition: the number of NO molecules=10; the number of $O_2$ molecules=100; and the number of $N_2$ molecules=9,890. When the number of $O_2$ molecules in the gas diffusing into the second passage is taken as 1, the number of NO molecules in the gas diffusing into the second passage is calculated as 10×9,999/9,900 at steady state. Because the number of NO molecules=(gain for the number of NO molecules)×(the number of NO molecules (in the gas which has diffused into the second passage)), as the concentration of oxygen in the measurement gas increases, the gain for the number of NO molecules decreases.

Next is the case where NO dissociates in the first passage. Here, the measurement gas (the total number of molecules per unit volume=10,000) has the following composition: the number of NO molecules=10; the number of $O_2$ molecules= 1,000;and the number of $N_2$ molecules=8,990. When one NO molecule dissociates (percentage of dissociation=10%, or ratio dissociation=0.1) in the first passage, and consequently the gas diffusing into the second passage contains one $O_2$ molecule, the number of NO molecules in the gas diffusing into the second passage is obtained as 9×9,999/9,000. This indicates that NO gain also varies as a result of the dissociation of NO in the first passage. Thus, the number of NO molecules can be obtained based on the concentration of oxygen (degree of enrichment of NO) in the measurement gas and the NO dissociation percentage in the first passage. Expressions for obtaining the concentration of NOx in the measurement gas based on Ip1 and Ip2 are shown below.

$$\text{Numbers of NO molecules [2st]} = \frac{\{(\text{number of NO molecules [m]}) - (\text{number of NO molecules [d]})\}(\text{total number of molecules}) - (\text{number of oxygen molecules [2st]})}{(\text{total number of molecules}) - (\text{number of oxygen molecules [m]})} \quad (a)$$

where

[m]: within measurement gas,

[2st]: within gas which has diffused into the second passage, and number of NO molecules [d]: number of NO molecules dissociated in the first passage.

Here, $$\text{Enrichment percentage} = \frac{(\text{total number of molecules}) - (\text{number of oxygen molecules [2st]})}{(\text{total number of molecules}) - (\text{number of oxygen molecules [m]})} \times 100(\%)$$

$$\text{Dissociation percentage} = \frac{(\text{number of NO molecules [d]})}{(\text{number of NO molecules [m]})} \times 100(\%)$$

Substituting them into Expression (a) gives

Number of NO molecules $[2st]$ = {(number of NO molecules [m]) −

(number of NO molecules [d])} ×

(enrichment percentage)/100

= {1 − (dissociation percentage)/100} ×

(number of NO molecules [m]) ×

(enrichment percentage)/100

Rearrangement gives

Number of NO molecules [m] = (b)

$$\frac{\text{(number of NO molecules [2st])}}{\{1 - \text{(dissociation percentage)}/100\} \times \text{(enrichment percentage)}/100}$$

Assuming that the number of oxygen atoms and a unit current make a one-by-one correspondence, Ip2=(number of NO molecules [2st])+2×(number of oxygen molecules [2st])

then

Ip2={1−(dissociation percentage)/100}×(enrichment percentage)/100×(number of NO molecules [m])+2×(number of oxygen molecules [2st])  (c)

Number of NO molecules [m] =  (d)

$$\frac{Ip2 - 2 \times \text{(number of oxygen molecules [2st])}}{\{1 - \text{(dissociation percentage)}/100\} \times \text{(enrichment percentage)}/100}$$

Taking "number of NO molecules [m]=(gain for number of NO molecules)×ΔIp2" gives Gain for number of NO molecules =  (e)

$$\frac{1}{\{1 - \text{(dissociation percentage)}/100\} \times \text{(enrichment percentage)}/100}$$

Because the enrichment percentage is identical for the same oxygen concentration, the following expression is obtained for any oxygen concentration.

1 − (dissociation percentage)/100 =  (f)

$$\frac{\text{(NO gain under the condition that NO does not dissociate in the first passage)}}{\text{(NO gain under the condition that NO dissociates in the first passage)}}$$

$Ip1$ = 2 × {(number of oxygen molecules [m]) −  (g)
(number of oxygen molecules [2st])} +
(number of NO molecules [d])
= 2 × {(number of oxygen molecules [m]) −
(number of oxygen molecules [2st])} +
(dissociation percentage)/100 ×
(number of NO molecules) [m]

Because the number of NO molecules per unit volume is the NOx concentration, the NOx concentration can be calculated based on the NO dissociation percentage in the first passage, the concentration of oxygen in the measurement gas, and the first and second pumping currents. Expressions for obtaining NOx concentration are shown below.

$$\text{NO concentration} = K \times \Delta Ip2 \quad (1)$$
$$= K \times (Ip2 - Ip2_0)$$

where

K: gain for NO concentration (reciprocal of sensitivity), ppm/μA, and $Ip2_0$: offset of Ip2; Ip2 as measured when the concentration of NO in the measurement gas is 0 ppm.

$$K = K0 + K1 \times O_2[\%] \quad (2)$$

where

K0: gain for NO concentration when the concentration of oxygen in the measurement gas is 0%, and K1: coefficient of an approximate expression representing the relationship between measured gain and oxygen concentration.

Substituting equation (2) into equation (1) gives:

$$\text{NO concentration} = (K0 + K1 \times O_2[\%]) \times (Ip2 - Ip2_0) \quad (3)$$

The relationship between the NO dissociation percentage [%] and oxygen concentration [%] is represented by the following approximate expression:

$$\text{NO dissociation percentage } [\%] = \alpha 0 + K2 \times O_2[\%] + K3 \times O_2[\%]^2 \quad (4)$$

where

NO dissociation percentage: (NO which has dissociated in first passage)/(NO contained in measurement gas)× 100, α0: NO dissociation percentage when the oxygen concentration is 0%, and K2, K3: coefficients of an approximate equation representing the relationship between experimentally obtained NO dissociation percentage and oxygen concentration.

Oxygen concentration can be obtained by the following expression:

$$O_2 [\%] = K4 \times \{Ip1 - K5 \times (\text{NO concentration}) \times \quad (5)$$
$$(\text{NO dissociation percentage } [\%])/100 - Ip1_0\}$$
$$= K4 \times \{Ip1 - K5 \times (\text{NO concentration}) \times$$
$$(\alpha 0 + K2 \times O_2 [\%] + K3 \times O_2 [\%]^2)/100 - Ip1_0\}$$

where $Ip1_0$: Ip1 as measured when the concentration of NO in the measurement gas is 0 ppm and the oxygen concentration is 0%, K4: coefficient of an approximate equation representing the relationship between oxygen concentration and "$Ip1 - Ip1_0$" obtained when the NO concentration is 0 ppm, and K5: {current Ip1 (=IB) measured when NO of a predetermined concentration has all dissociated in the first passage}/(the predetermined NO concentration), i.e., current per an NO concentration of 1 ppm as measured when all the NO has dissociated in the first passage.

Proportional coefficients K0 through K5, $Ip1_0$ and $Ip2_0$ are experimentally obtained, and Ip1 and Ip2 are measured. Accordingly, NOx concentration and oxygen concentration can be obtained by solving the simultaneous system of equation (3) and equation (5).

A method for experimentally obtaining the proportional coefficients K0 through K5 will next be described.

K0

K0 is "$\Delta Ip2/\Delta NO$ concentration" obtained when the concentration of oxygen in the measurement gas is 0 ppm.

K1

While the concentration of oxygen in the measurement gas is varied, "$\Delta Ip2/\Delta NO$ concentration" is obtained. K1 is determined by solving an approximate expression representing the relationship between oxygen concentration and "$\Delta Ip2/\Delta NO$ concentration".

K2 and K3

K2 and K3 are experimentally obtained from the relationship between the concentration of oxygen in the measurement gas and the NO dissociation percentage in the first passage. The NO dissociation percentage is obtained based on a limit current (=IB) of Ip1 as measured when all NO of a predetermined concentration dissociates in the first passage and $\Delta Ip1$ as measured under the condition that a portion of NO of the predetermined concentration dissociates in the first passage ($\Delta Ip1=Ib =Ip1[NO=predetermined$ $concentration]-Ip1[NO=0]$). The NO dissociation percentage=Ib/IB

K4

K4 is a gain for oxygen concentration. Ip1 is measured for a measurement gas having an NO concentration of 0 ppm and an oxygen concentration of 0% and for a measurement gas having an NO concentration of 0 ppm and a predetermined oxygen concentration. K4 is experimentally obtained from the relationship between the change in oxygen concentration with the change in Ip1.

K5

K5 can be obtained based on IB described above, and the NOx concentration when Ip1 has reached IB. When the concentration of NOx in the measurement gas is very small as compared to the concentration of oxygen in the measurement gas, "K5×(NO concentration)×($\alpha$0+K2×(oxygen concentration)+K3 ×(oxygen concentration)$^2$)" in equation (5) may be substantially taken as 0. In this case, the concentration of oxygen in the measurement gas can be directly obtained from a measured Ip1.

Position of Oxygen Concentration Detection Electrode

As seen from FIGS. 14 and 21, when the concentration of oxygen in the measurement gas changes, the gradient of oxygen concentration within the first passage 2 changes, and the NO dissociation percentage in the first passage 2 changes. As shown in FIG. 14, by disposing the oxygen concentration detection electrode (Vs electrode) 7a in the vicinity of the inlet to the second diffusion hole 3, an error or difference between a target oxygen concentration (detected oxygen concentration) and the concentration of oxygen in the gas diffusing into the second passage 4 decreases, and thus the oxygen concentration dependence of offset ($Ip2_0$) decreases. By contrast, as shown in FIG. 21, when the Vs electrode 7a is disposed in the vicinity of the first diffusion hole 3, the above-mentioned error increases due to the influence of the oxygen concentration gradient in the first passage 2 and the influence of a variation in the concentration of oxygen in the measurement gas. Furthermore, when the concentration of oxygen in the measurement gas is high, the oxygen concentration gradient in the first passage 2 becomes steep. As a result, a region having an excessively low oxygen concentration expands within the first passage 2 as compared to the case of FIG. 14, causing an increase in the oxygen concentration dependence of the NO dissociation percentage. Accordingly, in order to decrease the oxygen concentration dependence of offset ($Ip2_0$) and the oxygen concentration dependence of the NO dissociation percentage, the Vs electrode 7a is preferably disposed in the vicinity of the inlet to the second porous diffusion element 3 so as to be disposed away from the first diffusion hole 3.

BRIEF DESCRIPTION OF THE DRAWINGS

FIG. 16 is an explanatory chart illustrating the principle of measurement of NOx concentration in the case where NO does not dissociate in the first internal space.

FIG. 17 is an explanatory chart illustrating the principle of measurement of NOx concentration in the case where NO partially dissociates in the first internal space.

DESCRIPTION OF SYMBOLS

1: first diffusion passage (first diffusion hole)
2: first internal space (first passage)
3: second diffusion passage (second diffusion hole)
4: second internal space (second passage)
5-1, 5-3, 5-5: oxygen-ion conductive solid electrolyte layer
5-2, 5-4: insulating layer
6: first pumping cell
6-$a$, 6$a$: outer porous electrode of the first pumping cell 6
6-$b$, 6$b$: inner porous electrode of the first pumping cell 6
7: oxygen-concentration measuring cell (oxygen-partial pressure detection cell)
7-$a$, 7$a$: oxygen-concentration detection electrode of the oxygen-concentration-measuring cell 7 for detecting an oxygen partial pressure at a gas inlet to the second internal space by measuring electromotive force voltage Vsm across electrodes 7$a$, 7$b$, of the oxygen-concentration measuring cell 7, based on Nernst Equation
7-$b$, 7$b$: reference oxygen-concentration electrode of the oxygen-concentration measuring cell 7 for giving a constant oxygen-partial pressure reference in maintaining the target oxygen concentration by setting the target voltage Vs across the electrodes 7$a$, 7$b$
8: second pumping cell
8-$a$, 8$a$: porous cathode electrode of the second pumping cell 8
8-$b$, 8$b$: porous anode electrode of the second pumping cell 8
9: reference oxygen space which maintains a constant reference oxygen partial pressure, identically shown with the reference oxygen-concentration electrode 7-$b$, 7$b$
10: heater placed in vicinity of the cells for heating the cells

DESCRIPTION OF THE PREFERRED EMBODIMENTS

Figure 18:
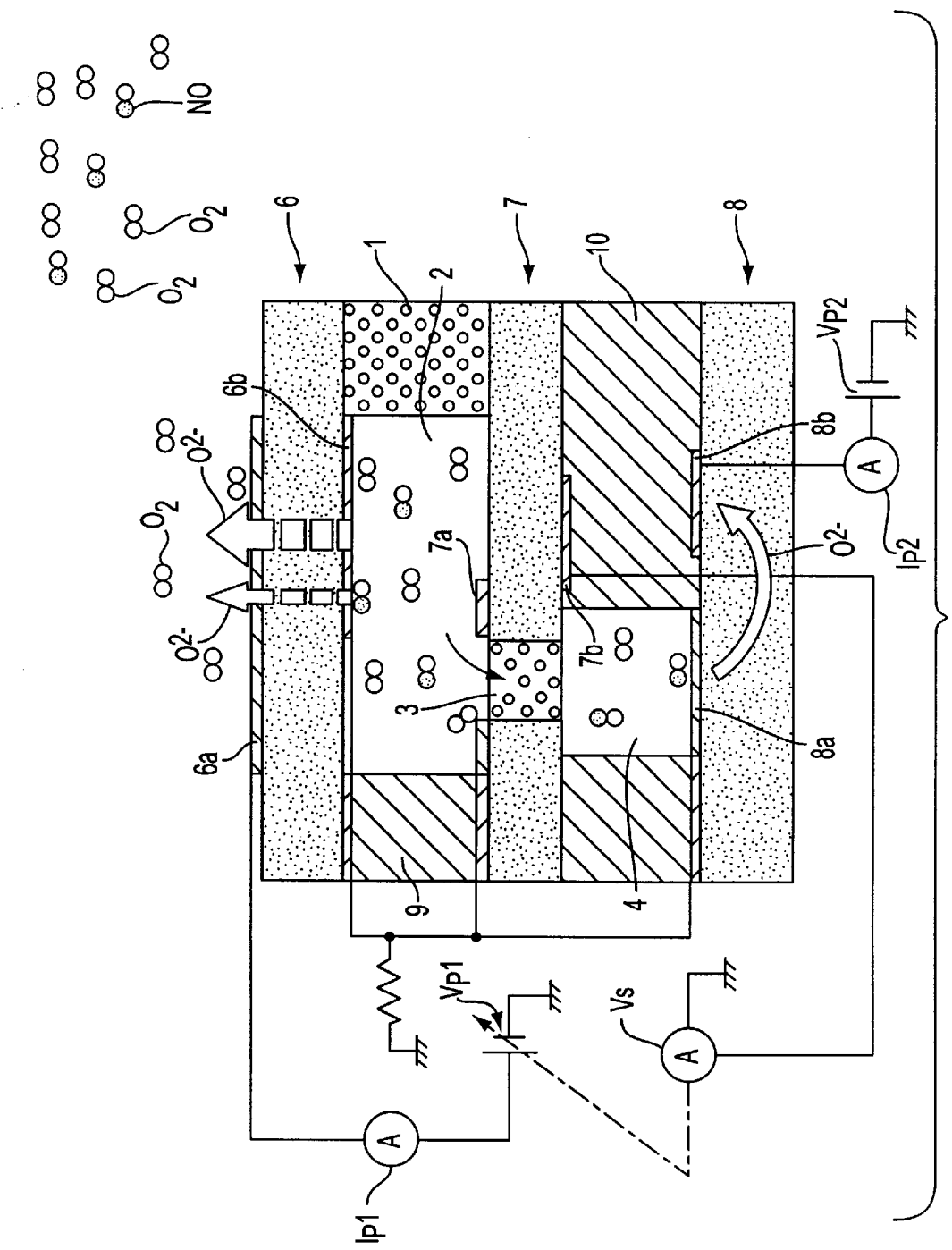
FIG. 18 is an explanatory view showing an NOx concentration sensor used in an embodiment of the present invention.
Figure 21:
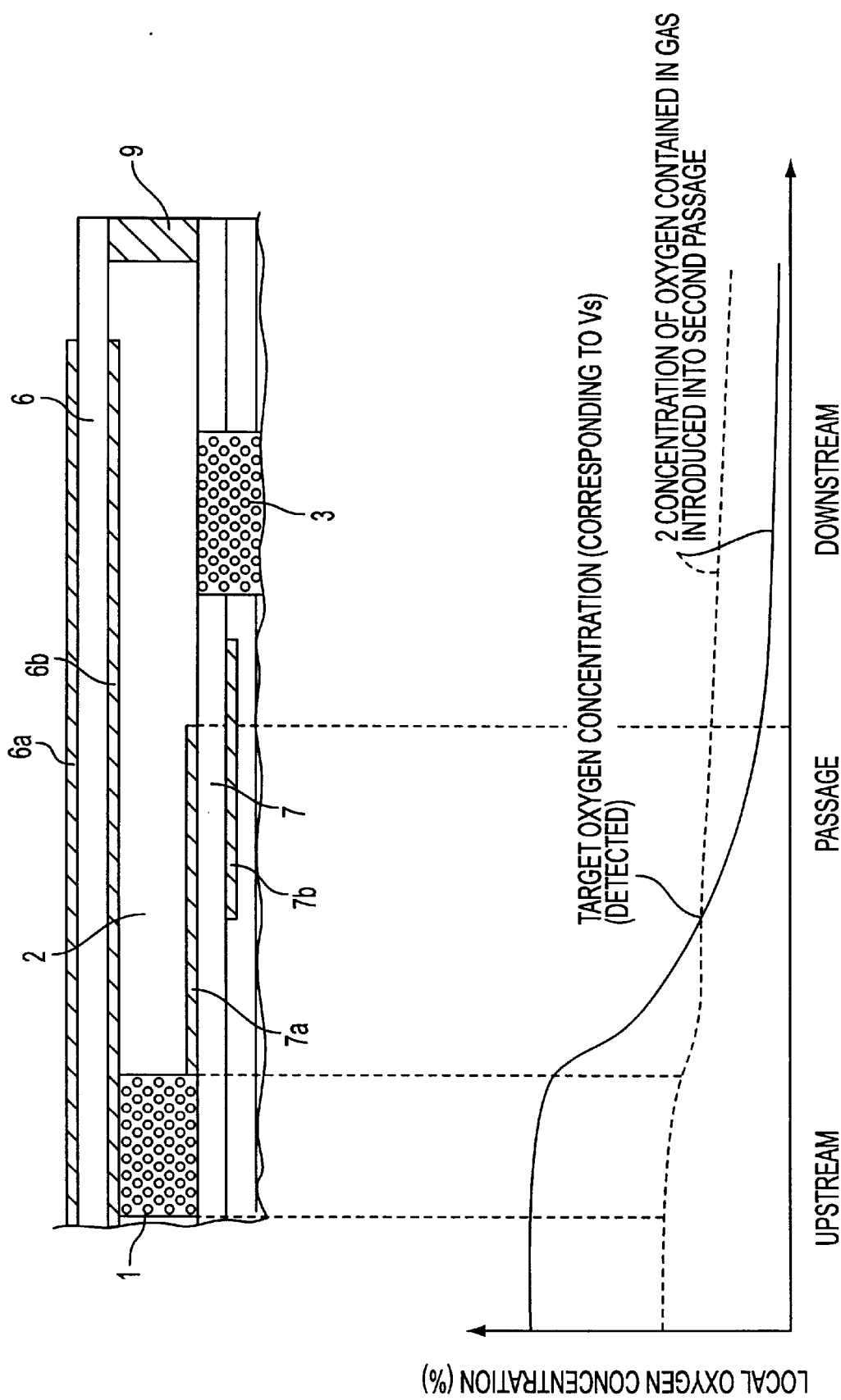
FIG. 21 is an explanatory view showing the relationship between the location of an oxygen concentration detection electrode and the distribution of oxygen concentration within the first internal space of a two-serial-space NOx sensor sample.

Preferred Embodiments of an Electrode of the First Pumping Cell Located on the First Passage Side and the Vs Electrode Referring to FIG. 18, the oxygen concentration of a space just above the oxygen concentration detection electrode 7$a$ positioned at a gas inlet (second diffusion hole 3) to the second passage 4 is preferably constant. To achieve this end, the inner electrode 6$b$ (of the first pumping cell 6) located inside on the first passage 2 is made shorter than the length of the first passage 2 (see FIG. 21), in a gas flow direction. The electrode 6$b$ is disposed at the upstream side of the first passage 2 (on the side of a measurement-gas inlet to the first passage 2 (namely the first diffusion hole 3). The Vs electrode 7$a$ is disposed at the downstream side of the first passage 2 (on the side of the inlet to the second passage 4, namely, on the side of the second diffusion hole 3 ). Also, as shown in FIG. 18, the Vs electrode 7$a$ is disposed so as to surround an opening of the second diffusion hole 3. In this case, the opening and the Vs electrode 7$a$ are preferably concentric with each other. The Vs electrode 7$a$ may be partially or entirely formed so as to face the second diffusion hole 3 or may be partially or entirely formed inside the second diffusion hole 3. Alternatively, the Vs electrode 7$a$ may be formed on the opening of the second diffusion hole 3 using a porous electrode.

Preferred Embodiment of a Pair of Electrodes of the Second Pumping Cell

As shown in FIG. 18, a pair of the electrodes 8$a$ and 8$b$ of the second pumping cell 8 are formed on the same surface of a solid electrolyte layer. Only the electrode 8$a$ is exposed to the second passage 4. Because the electrode 8$b$ is covered, the effective voltage applied between the electrodes 8$a$ and 8$b$ is stabilized. The electrodes 8$a$ and 8$b$ may be formed so as to sandwich the solid electrolyte layer therebetween.

Offset Value of the Second Pumping Current

When $\{K5\times(NO\ concentration)\times(\alpha 0+K2\times O_2[\%]+K3\times O_2[\%]^2/100)\}$ in equation (5) can be substantially taken as 0, oxygen concentration can be directly obtained from Ip1. Accordingly, $Ip2_0$ in equation (1) can be corrected for the concentration of oxygen in the measurement gas.

Preferable NO Dissociation Percentage in the First Passage

In order to improve measurement accuracy, the NO dissociation percentage in the first passage is preferably not greater than 50%, more preferably not greater than 20%, particularly preferably not greater than 15%. When the NO dissociation percentage is too small, the oxygen concentration dependence and temperature dependence of the NOx concentration measurement increase(s). Accordingly, the NO dissociation percentage is preferably not less than 0.5%, more preferably not less than 1%, particularly preferably not less than 3%. The NO dissociation percentage can be adjusted by appropriately setting the temperature of the detection element.

Vs:

Vs corresponding to a target oxygen concentration is set such that the concentration of oxygen in the gas diffusing into the second passage becomes sufficiently low.

Electrode:

An electrode of the first pumping cell located on the first passage side preferably has a catalytic activity for sufficient dissociation of oxygen and sufficient combustion of interfering gases (for example, combustible gases such as HC and CO) and a relatively suppressed catalytic activity for the dissociation of NO (in order to diffuse a sufficient quantity of NO into the second passage). The electrode is made of, for example, a Pt-Au alloy. The electrode material may contain, in place of or together with Au, a component (for example, Cu) for suppressing the catalytic activity of Pt for the dissociation of NO.

NOx Concentration Calculator

An NOx concentration calculator calculates NOx concentration by means of a microcomputer in which the relationship between oxygen concentration and gain K as well as coefficients such as K0 are stored, into which Ip1 and Ip2 are input, and in which a calculation equation for oxygen concentration and a calculation equation for NOx concentration are programmed. Also, the concentration of oxygen in the measurement gas may be measured by means of a separate oxygen sensor. Based on the thus-measured oxygen concentration and an output from the NOx concentration sensor, NOx concentration may be determined. For example, in an automobile exhaust system, based on an output from an oxygen sensor used for detecting an air-fuel ratio, a gain for NOx concentration can be selected according to oxygen concentration. An NOx concentration sensor based on the present invention can be favorably used in an atmosphere which involves a great variation in oxygen concentration, such as an exhaust system of an internal combustion engine (particularly, an automobile lean-burn engine).

Oxygen-Concentration-Measuring Cell

Figure 19:
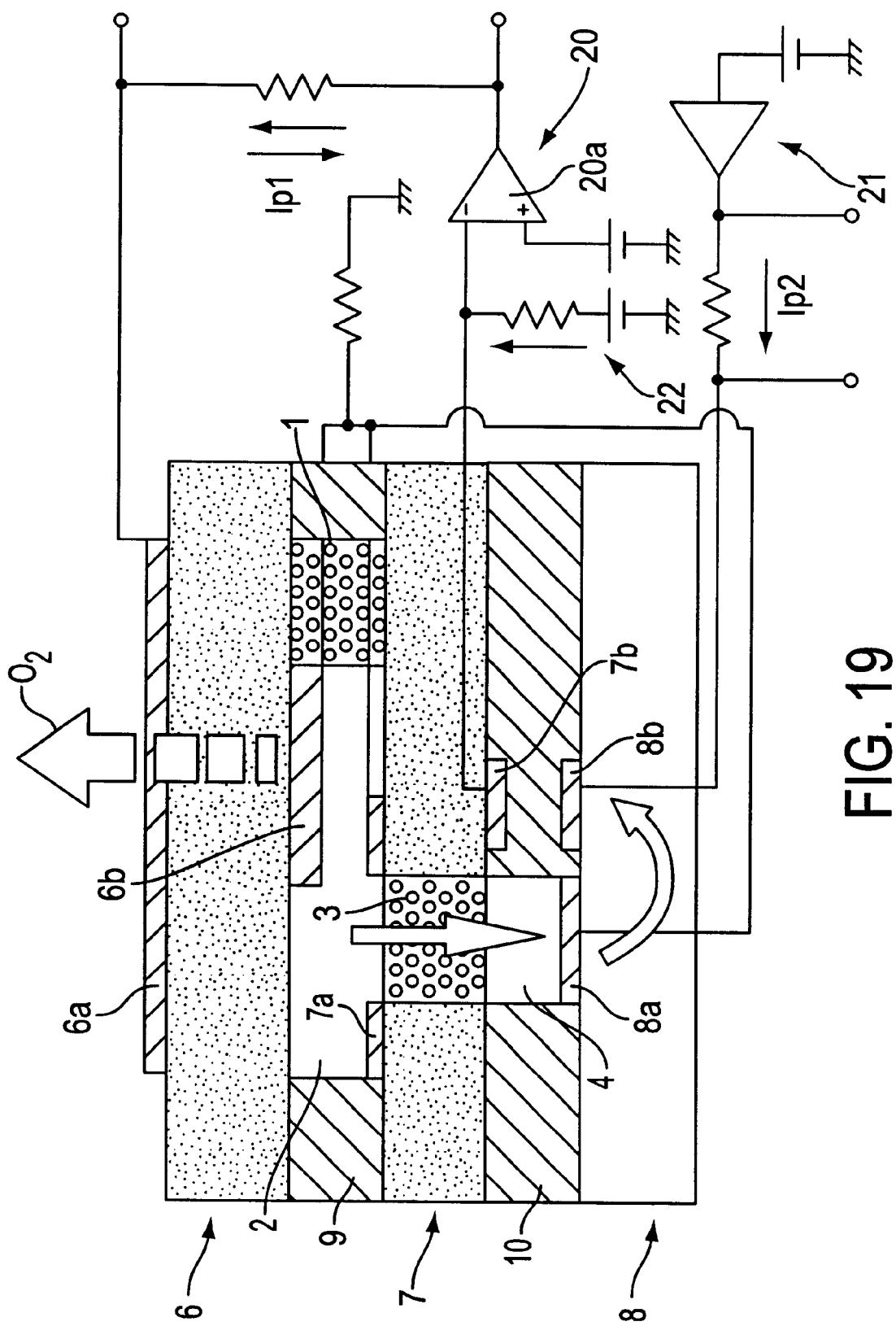
FIG. 19 is an explanatory view showing a controller for the NOx concentration sensor used in an embodiment of the present invention.
Figure 20:
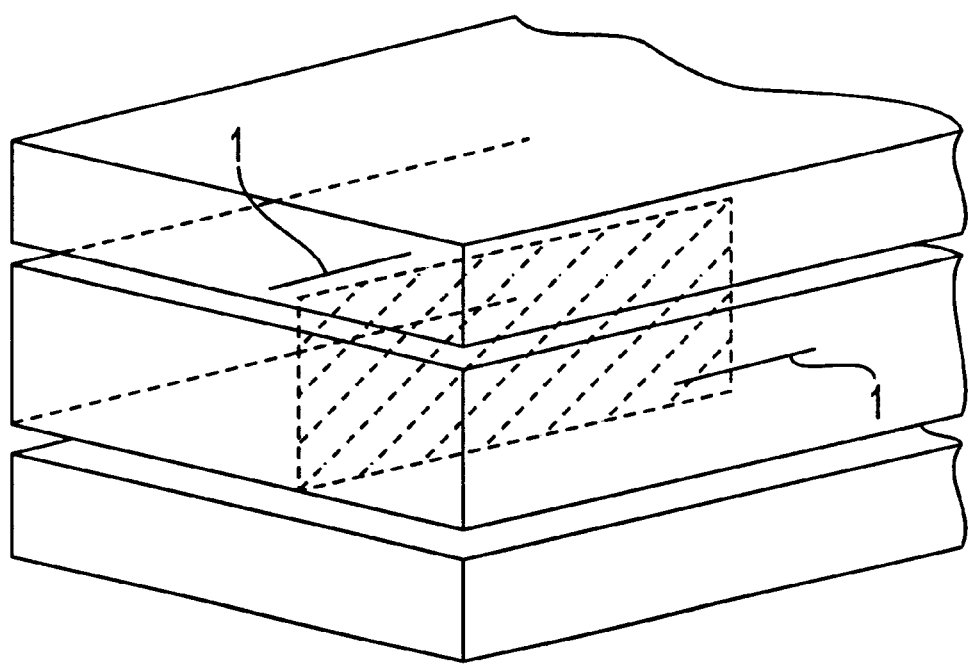
FIG. 20 is a view showing where the sectional plane of FIG. 18 is located within the NOx concentration sensor.

The oxygen-concentration-measuring cell will be described with reference to FIG. 19. A reference oxygen source may be so formed by directly or indirectly introducing the surrounding air having about oxygen concentration of 0.2 atm to the side of the oxygen concentration reference electrode 7b which is porous. In another way, oxygen may be pumped out to the side of the oxygen concentration reference electrode 7b by applying a constant small current between the electrodes 7a and 7b of the oxygen-concentration-measuring cell 7, thereby forming a reference oxygen space around or in the electrode 7b. Thus, the electrode 7b can be used as an oxygen self-generation-type reference electrode. This self-generation-type reference electrode may have an advantage in that the reference oxygen concentration is less susceptible to variations in the oxygen concentration of the surrounding air, providing a constant oxygen partial pressure reference of e.g. 2 atm.

Attachment of Element of NOx Concentration Sensor

Figure 22:
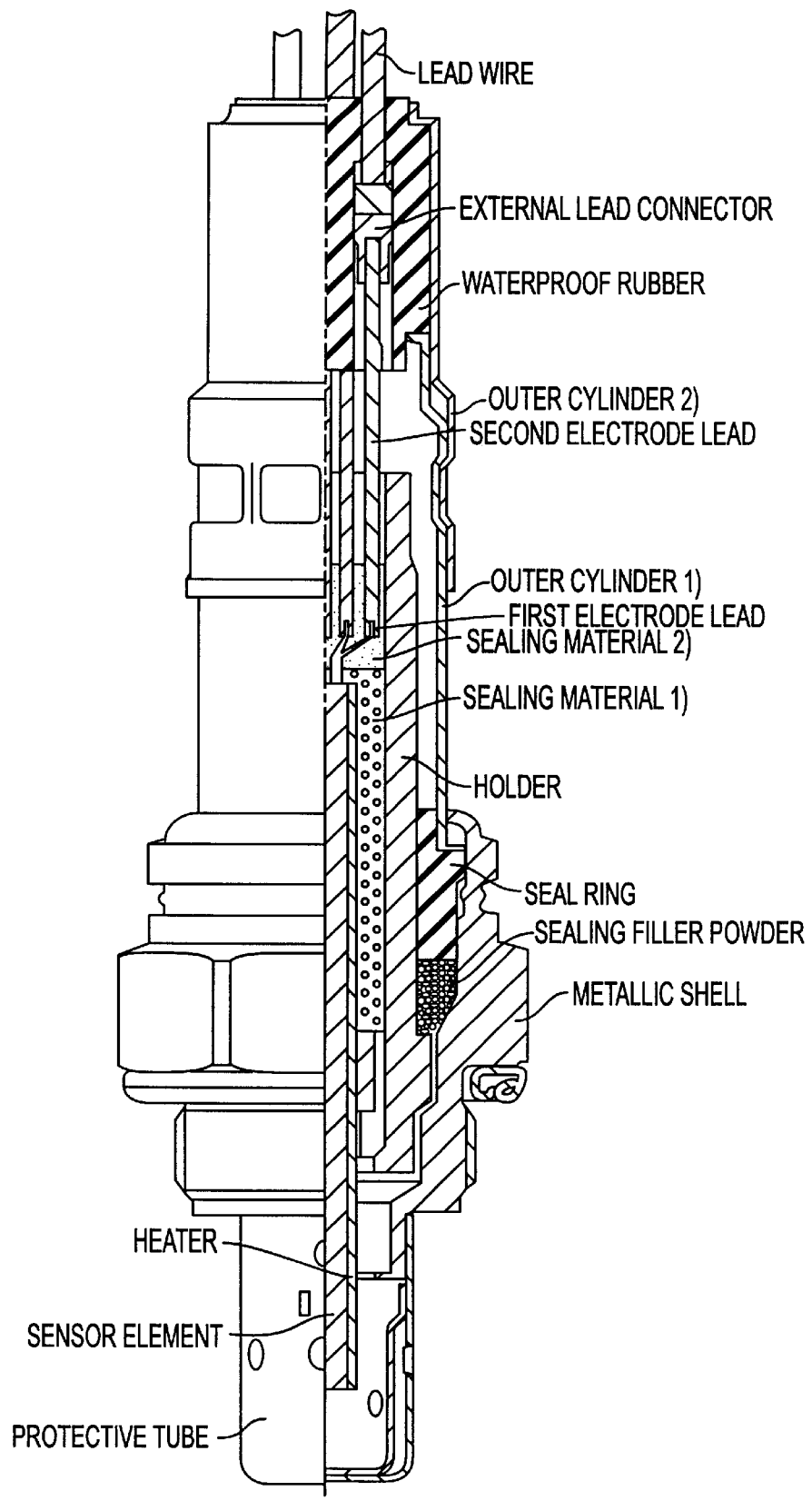
FIG. 22 is a view showing a fitting assembly including the NOx concentration sensor of the present invention.

As an illustration, FIG. 22 shows the attachment of an element (hereinafter referred to as a gas sensor element) of the NOx concentration sensor shown in FIGS. 18 and 19 into a fitting assembly. The gas sensor element is fixed within the fitting assembly such that its measurement gas inlet (first diffusion hole) is located within a protector (protective tube) having holes formed therein. A heater is attached onto the gas sensor element along the longitudinal direction of the element. Upper portions of the gas sensor element and the heater in FIG. 22 are covered with two kinds of sealing materials. A lower sealing material 1) is porous to permit gas to pass therethrough. An upper sealing material 2) is airtight. A holder is disposed around the sealing materials. A stainless steel seal ring is fitted between the holder and a metallic shell, while sealing filler powder made of talc is filled into a space defined by the holder, the metallic shell and the seal ring. The lower end of the layer of the sealing filler powder abuts a flange portion of the holder. Through the seal ring and the sealing filler powder, a tightening force acts in the radial direction of the metallic shell as well as in the axial direction of the metallic shell, thereby fixing the holder with respect to the metallic shell and holding the gas sensor element in a stable manner. At an upper portion of the fitting assembly in FIG. 22, a first outer cylinder 1) and a second outer cylinder 2) are coaxially engaged with each other. The first outer cylinder 1 ) extends into the metallic shell and is engaged with the metallic shell. Waterproof rubber is fitted into an upper portion of the second outer cylinder 2 in FIG. 22. Electrodes formed on the gas sensor element (see FIG. 18) are electrically connected to first electrode leads having a gas diffusion resistance. The first electrode leads are electrically connected to second electrode leads. The second electrode leads are electrically connected to covered lead wires via an external lead connection portion. The destination for oxygen pumped into a reference oxygen space formed around the reference oxygen concentration electrode is not particularly limited. For example, the oxygen may be returned to the atmosphere via the electrode leads, the measurement gas atmosphere, or a passage.

The number of leads required for controlling and outputting a signal from the NOx concentration sensor, including a heater lead, may be seven. By using a common lead which is electrically connected to the electrodes 6b, 7a and 8a (see FIGS. 18 and 19), the number of leads can be reduced to six. Furthermore, by electrically connecting the common lead to the negative side of the heater, the number of leads can be reduced to five.

Method for Manufacturing NOx Concentration Sensor $ZrO_2$ green sheets coated with paste for forming an electrode, paste for forming a passage, and the like paste are arranged in layers. The resulting laminated assembly is fired, yielding the NOx concentration sensor. The methods for manufacturing component parts of the NOx concentration sensor will next be described for illustration.

Formation of $ZrO_2$ Green Sheet $ZrO_2$ powder (which contains a stabilizer and is hereinafter referred to simply as $ZrO_2$ powder) preliminarily fired in an atmospheric furnace, a dispersant, an organic solvent and balls are mixed and dispersed using a trommel. To the resulting mixture, an organic binder dissolved in an organic solvent is added, followed by mixing, to thereby obtain a slurry. The thus-obtained slurry is sheeted according to a known doctor blading method, yielding a $ZrO_2$ green sheet.

Pastes for Printing

Paste for the first pumping electrode 6 a reference oxygen concentration electrode 7b, and second pumping electrodes 8a and 8b Platinum powder, $ZrO_2$ powder and an appropriate amount of organic solvent are mixed and dispersed using a ball mill (or a pot mill). To the resulting mixture, an organic binder dissolved in an organic solvent is added, and a viscosity conditioner is further added, followed by mixing, thereby yield a paste.

Paste for the first pumping electrode 6b and oxygen concentration (partial pressure) detection electrode 7a Platinum powder, $ZrO_2$ powder and an appropriate amount of organic solvent are mixed and dispersed using a ball mill (or a pot mill). To the resulting mixture, an organic binder dissolved in an organic solvent is added, and a viscosity conditioner is further added, followed by mixing, to thereby yield a paste.

Paste for insulation coat and protective coat

Alumina powder and an appropriate amount of organic solvent are mixed and dissolved using a ball mill (or a pot mill). To the resulting mixture, a viscosity conditioner is added, followed by mixing, to thereby yield a paste.

Paste for Pt-containing porous material (for lead wire)

Alumina powder, platinum powder, an organic binder and an organic solvent are mixed using a ball mill (or a pot mill). To the resulting mixture, a viscosity conditioner is added, followed by mixing, to thereby yield a paste.

Paste for first diffusion hole

Alumina powder, an organic binder and an organic solvent are mixed and dispersed using a ball mill (or a pot mill). To the resulting mixture, a viscosity conditioner is added, followed by mixing, to thereby yield paste.

Paste for carbon coat

Carbon powder, an organic binder and an organic solvent are mixed and dispersed using a ball mill (or a pot mill). To the resulting mixture, a viscosity conditioner is added, followed by mixing, to thereby yield a paste. A carbon coat layer can be formed by printing to prevent, for example, contact between the inner electrode of the first pumping cell and the oxygen concentration detection electrode. The carbon coat layer is also used for forming spaces serving as the first and second passages. Because carbon is burned during firing, the carbon coat layer is not present in a fired body.

Pellet Compact

Pellet compact for second diffusion hole

Alumina powder, an organic binder and an organic solvent are mixed and pelletized using a ball mill (or a pot mill). The resulting mixture is press-worked into a columnar pellet compact (in a green state).

Method for Laminating $ZrO_2$ Green Sheets $ZrO_2$ green sheets of the second and third layers are united under pressure. Then, the second diffusion hole is punched in the laminated $ZrO_2$ green sheets. Subsequently, the above-mentioned pellet compact in the green state is embedded into the hole. Then, another $ZrO_2$ green sheet is placed on the laminated $ZrO_2$ green sheets, followed by uniting under pressure.

Removal of Binder and Firing

The pressure-united body is heated for removing binder therefrom and is then fired.

The dimensions of an element of the NOx concentration sensor used in the Examples, which will be described later, are described below. The element had a length (a dimension in the longitudinal direction) of 50 mm, a width (a dimension in the lateral direction) of 4 mm, and a thickness (a dimension in the direction of lamination) of 1.3 mm. The first pumping cell had a thickness of 0.35 mm (resistance: 40 to 60 Ω at a pumping cell temperature of about 800° C.). The second pumping cell had a thickness of 0.35 mm (resistance: 40 to 60 Ω at a pumping cell temperature of about 800° C.). The electrodes 6a and 6b of the first pumping cell 6 had a longitudinal length of 7 mm and 4 mm, respectively, and a width of 2 mm. The electrodes 8a and 8b of the second pumping cell 8 had a longitudinal length of 7 mm and a width of 2 mm. The electrodes 7a and 7b of the oxygen-concentration-measuring cell 7 had a longitudinal length of 2 mm and a width of 2 mm. Al of the electrodes had a thickness of 10 to 20 μm. The first and second passages had a height of about several tens of μm (about 50 μm).

EXAMPLES

The method for measuring the concentration of NOx in a measurement gas and the NOx concentration sensor according to the present invention will next be described by way of example. However, the present invention should not be construed as being limited thereto.

Example 1 a) The NOx concentration sensor of the present example will be described with reference to FIG. 1 which schematically shows a longitudinal sectional view of the sensor.

Figure 1:
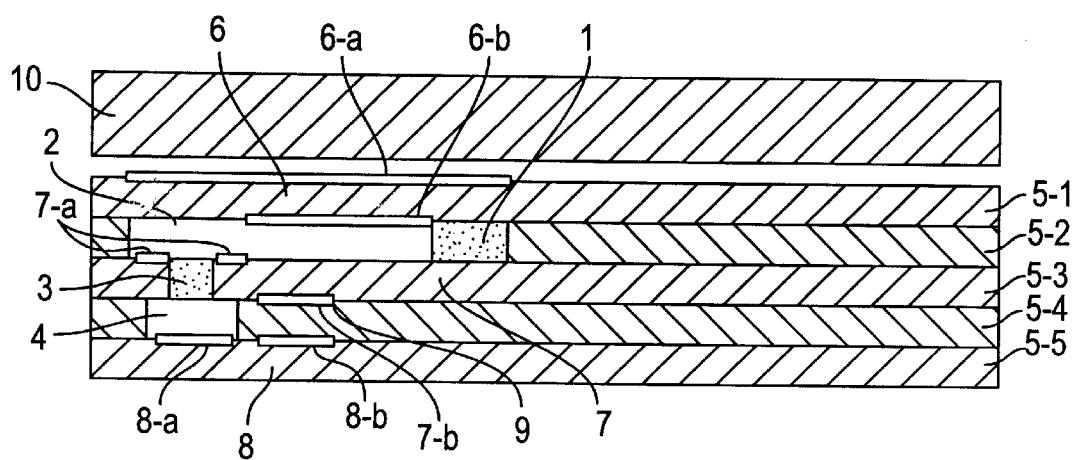
FIG. 1 is a longitudinal sectional view of an NOx concentration sensor used in one of the embodiments of the present invention.

In FIG. 1, numeral 1 denotes a first diffusion passage (first diffusion resistance element); numeral 2 denotes a first space; numeral 3 denotes a second diffusion passage (second diffusion resistance element); numeral 4 denotes a second space; numerals 5-1, 5-3, and 5-5 denote three oxygen-ion conductive solid electrolyte layers in lamination, each of which is made of zirconia ceramic sheet; numeral 6 denotes a first pumping cell (an oxygen ion pumping cell is referred to as a pumping cell); numerals 6-a and 6-b denote porous electrodes of the first pumping cell; numeral 7 denotes an oxygen-concentration measuring cell; numerals 7-*a* and 7-*b* denote porous electrodes of the oxygen-concentration-measuring cells 7; numeral 8 denotes a second pumping cell; numerals 8-*a* and 8-*b* denote porous electrodes of the second pumping cell; numeral 9 denotes a reference oxygen space communicating with outside air for oxygen reference although the reference electrode 9 is shown the same as the porous electrode 7-*b* that also communicates with outside air for the oxygen reference; and numeral 10 denotes a heater for heating the electrolytes layers 5-1, 5-3, 5-5. Insulating layers 5-2, 5-4 made of alumina ceramic are interposed between the solid electrolyte layers 5-1, 5-3, 5-5. The first diffusion passage 1 is provided so as to open onto the exterior of the sensor at a longitudinal side of the sensor. FIG. 1 shows the first diffusion passage 1 for convenience of indication of its location. The diffusion passage is a diffusion resistance element having a diffusion resistance, which limits gas diffusion from the measurement gas space. Furthermore, in the structure of FIG. 1, the insulating layers 5-2, 5,4 may possibly be replaced with solid electrolyte layers.

The porous electrode 7-*a* is provided on the oxygen-concentration-measuring cell 7 so as to be exposed to the first space 2 and positioned annularly around the opening of the second diffusion passage 3 (namely, a gas inlet of the second space 4). A constant small current is applied between the electrodes 7-*a* and 7-*b* of the oxygen-concentration-measuring cell 7 so as to pump out oxygen to the side of the electrode 7-*b*, thereby forming a reference oxygen space around the electrode 7-*b*. Thus, the electrode 7-*b* can be used as a self-generation-type reference electrode. The formation of such a self-generation-type reference electrode has an advantage that the reference oxygen concentration is less susceptible to changes in the oxygen concentration of the surrounding atmosphere, as previously maintained.

The second diffusion passage 3 is located away from the first diffusion passage 1. This arrangement also enables accurate control of oxygen concentration in the vicinity of the gas inlet of the second space 4, in combination with the annularly positioned electrode 7-*a*. Accordingly, the oxygen concentration dependence of an offset component of the second pumping current and the oxygen concentration dependence of the NO dissociation percentage can be decreased. The electrode 6-*b* of the first pumping cell 6 exposed to the first space 2 is shorter then the first space 2 in the longitudinal direction of the first space 2 and is located so as not to hang over the second diffusion passage 3. This arrangement minimizes the effect of operation of the first pumping cell 6 on the oxygen concentration in the vicinity of the gas inlet of the second space 4 to thereby stabilize the oxygen concentration.

A pair of the electrodes 8-*a* and 8-*b* of the second pumping cell 8 are formed on the same surface of the solid electrolyte layer 5-5. The electrode 8-*a* is exposed to the second passage 4, whereas the electrode 8-*b* is interposed between the layers 5-5 and 5-4. This arrangement has an advantage that an effective voltage applied between the electrodes 8-*a* and 8-*b* is stabilized.

Material for the above-mentioned electrodes may be made from at lease one of metals such as platinum, palladium, rhodium, gold, silver and copper and mixing with the same ceramic components as those of the solid electrolyte layer. A lead of each electrode extends between the solid electrolyte layers to the right of FIG. 1. A terminal may be provided at the other end portion of the lead for electrical connection with a measuring circuit.

b) The basic operation of the NOx concentration sensor will next be described with reference to FIG. 1.

In the present example, the concentration of oxygen in the measurement gas introduced into the second space 4 from the first space 2 is monitored by measuring electromotive force voltage Vms outputted from the oxygen-concentration-measuring cell 7. The pumping voltage Vp1 is applied to the first pumping cell 6 in order to pump out oxygen from (or pump oxygen into) the first space 2 so that the output voltage Vsm of the oxygen-concentration-measuring cell 7 approaches a target voltage (for example, Vs=450 mV). At the same time, nitrogen oxide (NO) and oxygen ($O_2$) in the first space 2 dissociate as represented by the following formulae (A2) and (A3).

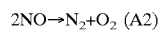

$2NO \rightarrow N_2 + O_2$ (A2)

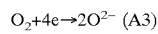

$O_2 + 4e \rightarrow 2O^{2-}$ (A3)

That is, operation of the first pumping cell 6 is controlled so as to control oxygen concentration in the vicinity of the gas inlet of the second space 4. This causes NO and $O_2$ to dissociate to an extent such that a portion of the NO dissociates in the first space 2, namely, the percentage $\alpha$ of dissociation of NO contained in the measurement gas assumes a value of not less than 0.5% (for example, within a range of 2% to 20%) in the first space 2.

At this time, the current (first pumping current) Ip1 flowing through the first pumping cell 6 is measured.

The resulting gas after the above dissociation of NO at a predetermined percentage $\alpha$ of dissociation is introduced into the second space 4 through the second diffusion passage 3. By the operation of the second pumping cell 8, residual $O_2$ and NO in the second space 4 are dissociated. Oxygen ions generated by the dissociation of $O_2$ and NO are pumped out by means of the second pumping cell 8. At this time, the current (second pumping current) Ip2 flowing through the second pumping cell 8 is measured.

The above pumped-out oxygen ions are generated as a result of the dissociation of $O_2$ and NO in the gas introduced into the second space 4 from the first space 2. Accordingly, the quantity of oxygen introduced into the second space 4 from the first space 2 appears in terms of an offset component (the second pumping current as measured when the quantity of NO is zero) of the second pumping current. The rest of the second pumping current corresponds to the quantity of NO which has not dissociated in the first space 2 and which has been introduced into the second space 4.

Using the thus-measured first pumping current and second pumping current, NO concentration is calculated by the method which will be described below in detail.

c) The following Equation (A1) for calculating the concentration of NO in the measurement gas will next be described.

$$\text{NOx concentration} = (Ip2 - Ip2\text{offset}) \times A/(1 - \alpha/100) \qquad (A1)$$

where
  $\alpha$: NO dissociation percentage in the first space (%),
  A: coefficient for converting a current signal corresponding to NOx concentration to an NOx concentration,
  Ip2: current flowing through the second pumping cell,
  Ip2offset: offset component of current flowing through the second pumping cell, and NOx concentration: concentration of NOx in the measurement gas.

In the present example, the first pumping cell 6 is controlled such that the output voltage Vsm of the oxygen-concentration-measuring cell 7 assumes a target voltage Vs (for example, 450 mV). At this time, the first pumping current is measured. That is, voltage is applied between the electrodes of the first pumping cell 6 so as to attain an oxygen concentration at which NO dissociates at a predetermined percentage α in the first space 2. At this time, the first pumping current corresponds to the percentage a of NO dissociating in the first space.

Residual NO and $O_2$ which have not dissociated in the first space and have been introduced into the second space 4 dissociate upon contacting the electrode 8-a of the second pumping cell 8. Accordingly, the second pumping current corresponds to the quantity of oxygen ions generated as a result of the dissociation of NO an $O_2$ in the second space 4. That is, the second pumping current includes not only a current corresponding to NO concentration but also an offset current corresponding to oxygen concentration. Accordingly, a current corresponding to the NO concentration of the second space 4 is represented by the difference between the second pumping current Ip2 and the offset current Ip2offset (Ip2−Ip2offset).

When the concentration of NO in the measurement gas is taken as 1, the NO concentration of the gas introduced into the second space 4 is represented by $(1-\alpha/100)$. Accordingly, a current corresponding to a total NO concentration is obtained by dividing the above-mentioned current differential (Ip2−Ip2offset) associated with the second pumping cell 8 by the NO concentration $(1-\alpha/100)$ of the gas introduced into the second space 4. Thus, the current is represented by $\{(Ip2-Ip2offset)/(1-\alpha/100)\}$.

Accordingly, the total NO concentration can be obtained by multiplying the above-obtained current by a predetermined conversion coefficient (a coefficient for converting current to NO concentration).

Thus, the concentration of NO in the measurement gas can be obtained using the above Expression (A1).

d) The procedure for determining the concentration of NO contained in the measurement gas using the NOx concentration sensor and Equation (A1) described above will next be sequentially described.

Figure 2:
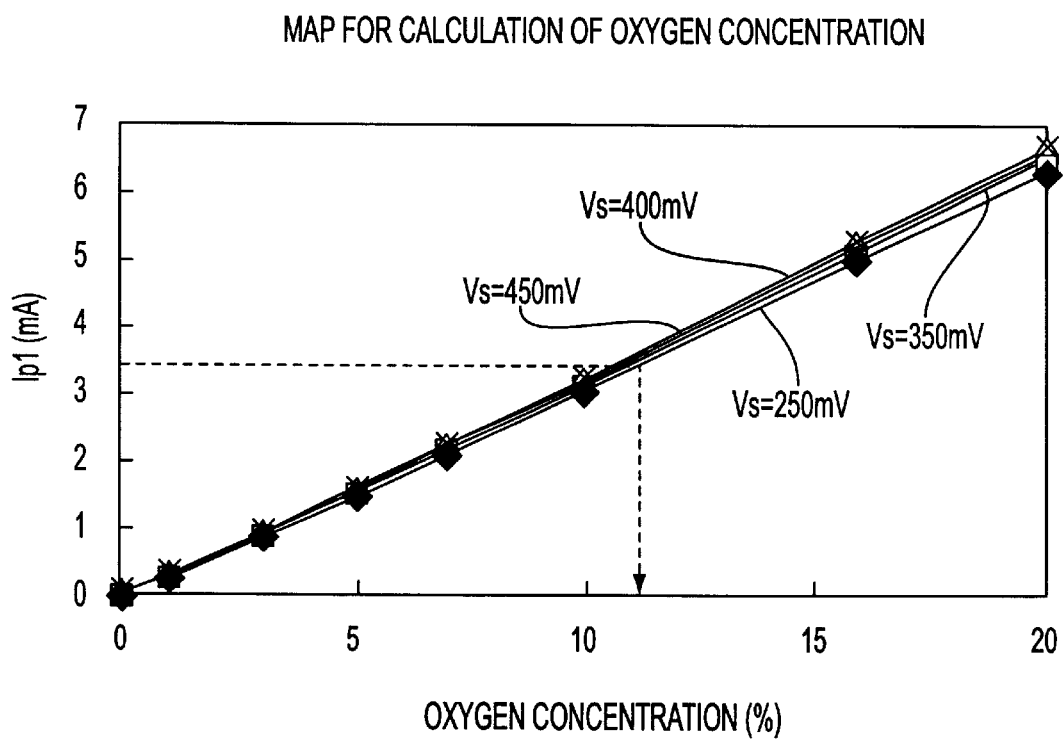
FIG. 2 is a graph showing the relationship among the target voltage set for the oxygen-concentration-measuring cell, the first pumping current, and oxygen concentration of the measurement gas.

While the target voltage Vs set for the oxygen-concentration-measuring cell 7 is specified as a parameter, the relationship between the first pumping current Ip1 and the concentration of oxygen in the measurement gas is experimentally obtained in advance. FIG. 2 shows an example map M1 representing such a relationship.

Specifically, in order to avoid the effect of NO, the above relationship is obtained using a gas which does not contain NO.

Figure 3:
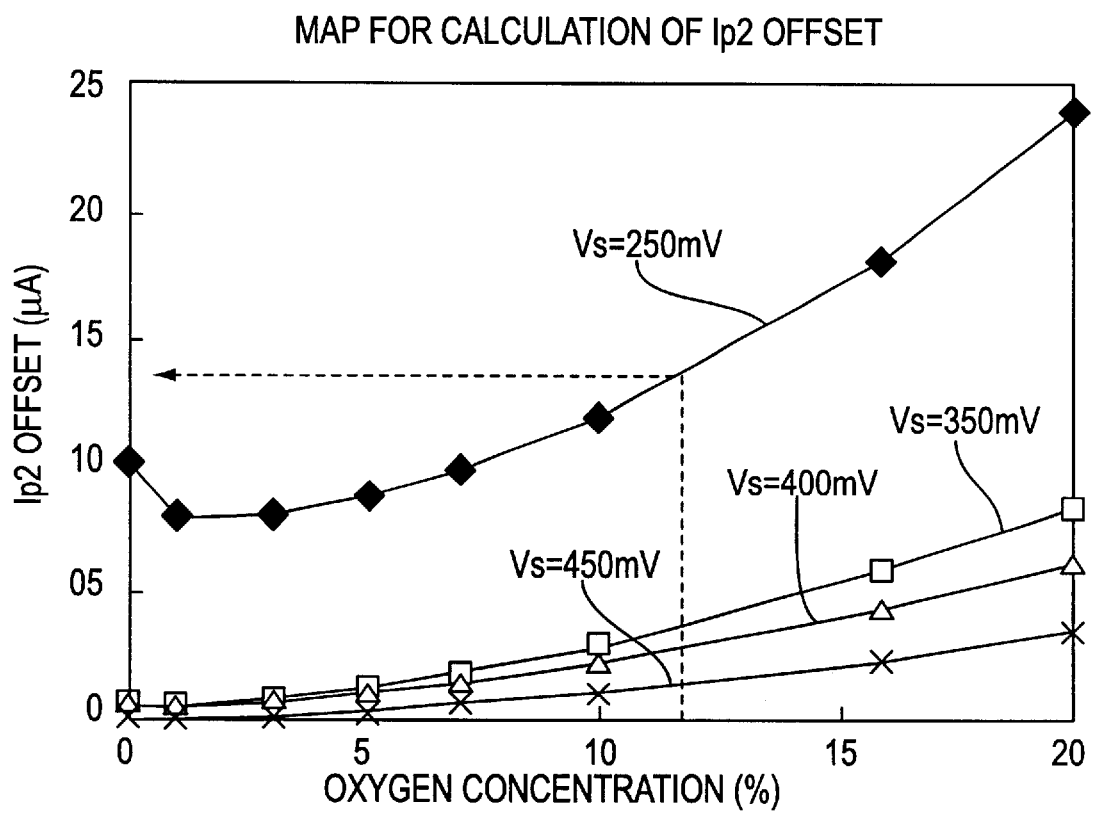
FIG. 3 is a graph showing the relationship among the target voltage set for the oxygen-concentration-measuring cell, offset current, and oxygen concentration of the measurement gas.

Similarly, while the target voltage Vs set for the oxygen-concentration-measuring cell 7 is specified as a parameter, the relationship between the offset current Ip2offset and the concentration of oxygen in the measurement gas is experimentally obtained in advance. FIG. 3 shows an example map M2 representing such a relationship.

Specifically, in order to avoid the effect of NO, the above relationship is obtained using a gas which does not contain NO. In this case, the measured second pumping current Ip2 becomes the offset current Ip2offset.

Figure 4:
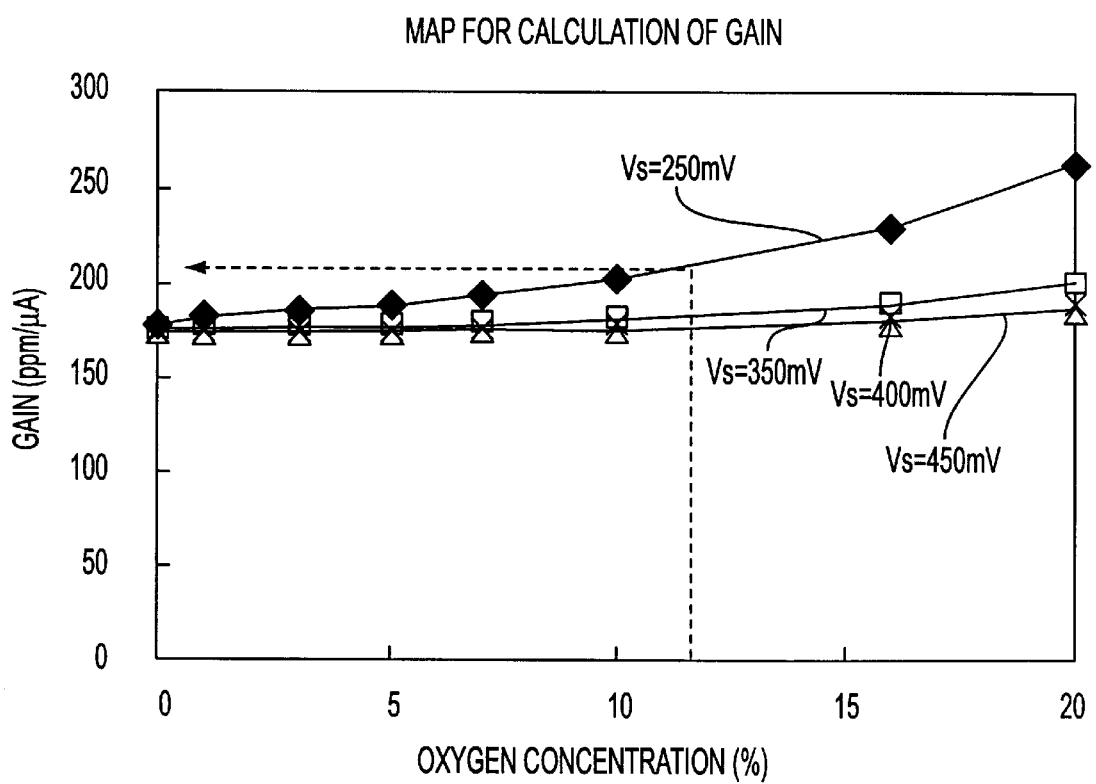
FIG. 4 is a graph showing the relationship among the target voltage set for the oxygen-concentration-measuring cell, gain, and oxygen concentration of the measurement gas.

Also, while the target voltage Vs set for the oxygen-concentration-measuring cell 7 is taken as a parameter, the relationship between gain expressed as $A/(1-\alpha/100)$ and the concentration of oxygen in the measurement gas is experimentally obtained in advance. FIG. 4 shows an example map M3 representing such a relationship.

This gain expressed as $A/(1-\alpha/100)$ is a multiplier used in calculation of NO concentration and is a function of the experimentally obtained target voltage Vs and oxygen concentration. Specifically, the gain is determined with the conversion coefficient A (:coefficient for conversion of current to NO concentration) given at an NO dissociation percentage of 0% while the percentage a of dissociation of NO is taken into account. The gain indicates variation in NO concentration corresponding to variation in second pump current Ip2.

The gain is the reciprocal of sensitivity, namely, the reciprocal of a value obtained by dividing second pump current (corresponding to NO dissociation in the second internal space) by NO concentration in the measurement gas. The value has the unit of for example, μA/ppm.

Specifically, the above relationship is obtained in the following manner.

Figure 6:
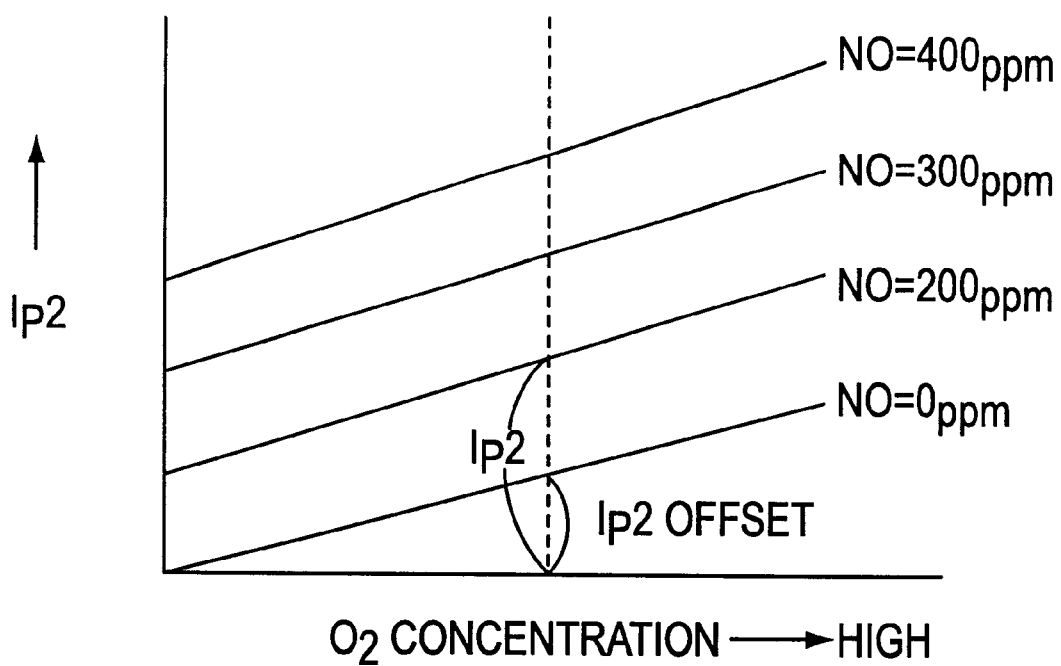
FIG. 6 is a graph showing the relationship among NO concentration, the second pumping current, and oxygen concentration of the measurement gas, in the two-serial space NOx concentration sensor.

By measuring a measurement gas having a known NO concentration and oxygen concentration, the relationship shown in FIG. 6 is obtained among the second pumping current Ip2, oxygen concentration and NO concentration. As seen from FIG. 6, at an NO concentration (e.g., 200 ppm), a current differential (Ip2−Ip2offset) corresponding to a certain oxygen concentration represents a true current value corresponding to the NO concentration. By dividing the current differential (Ip2−Ip2offset) μA by the NO concentration (e.g., 200 ppm), sensitivity is obtained. The reciprocal of the thus-obtained sensitivity is the gain.

By using the thus-obtained gain, the map M3 of FIG. 4 showing the relationship among gain, target voltage Vs, and oxygen concentration is prepared in advance.

An actual method for measuring NO concentration using the maps M1 to M3 will next be described.

First, the NOx concentration sensor is placed in a measurement space filled with a measurement gas of interest having an unknown NO concentration. The measurement gas is introduced into the first space 2 via the first diffusion passage 1.

In order to attain the target voltage Vs set for the oxygen-concentration-measuring cell 7, the operation of the first pumping cell 6 partially dissociates NO and $O_2$ contained in the measurement gas introduced into the first space 2 so as to attain a predetermined NO dissociation percentage a (at least 0.5%) forming a new gas at the inlet of the second space 4. A first pumping current Ip1 flows through corresponding to the extent of the dissociation. At this time, the first pumping current Ip1 is measured.

The new gas leaves the first space 2 to enter the second space 4 via the second diffusion passage 3. The new gas contains residual $O_2$ and NO which have not been dissociated in the first space 2.

Accordingly, by operation of the second pumping cell 8, residual NO and $O_2$ dissociate completely, and a corresponding second pumping current Ip2 flows. At this time, the second pumping current Ip2 is measured.

Using the thus-measured first pumping current Ip1 and the map M1 of FIG. 2, the concentration of oxygen in the measurement gas corresponding to the target voltage Vs is obtained.

Using the oxygen concentration obtained above from the map M1 and the map M2 of FIG. 3, the offset current Ip2offset corresponding to the target voltage Vs is obtained.

Similarly, using the oxygen concentration obtained above from the map M1 and the map M3 of FIG. 4, the gain represented as $A/(1-\alpha/100)$ corresponding to the target voltage Vs is obtained.

The thus-obtained second pumping current Ip2, offset current Ip2offset, and gain $A/(1-\alpha/100)$ are substituted into Expression (A1), to thereby obtain NO concentration.

e) The action and effects of the present example will next be described.

Figure 7:
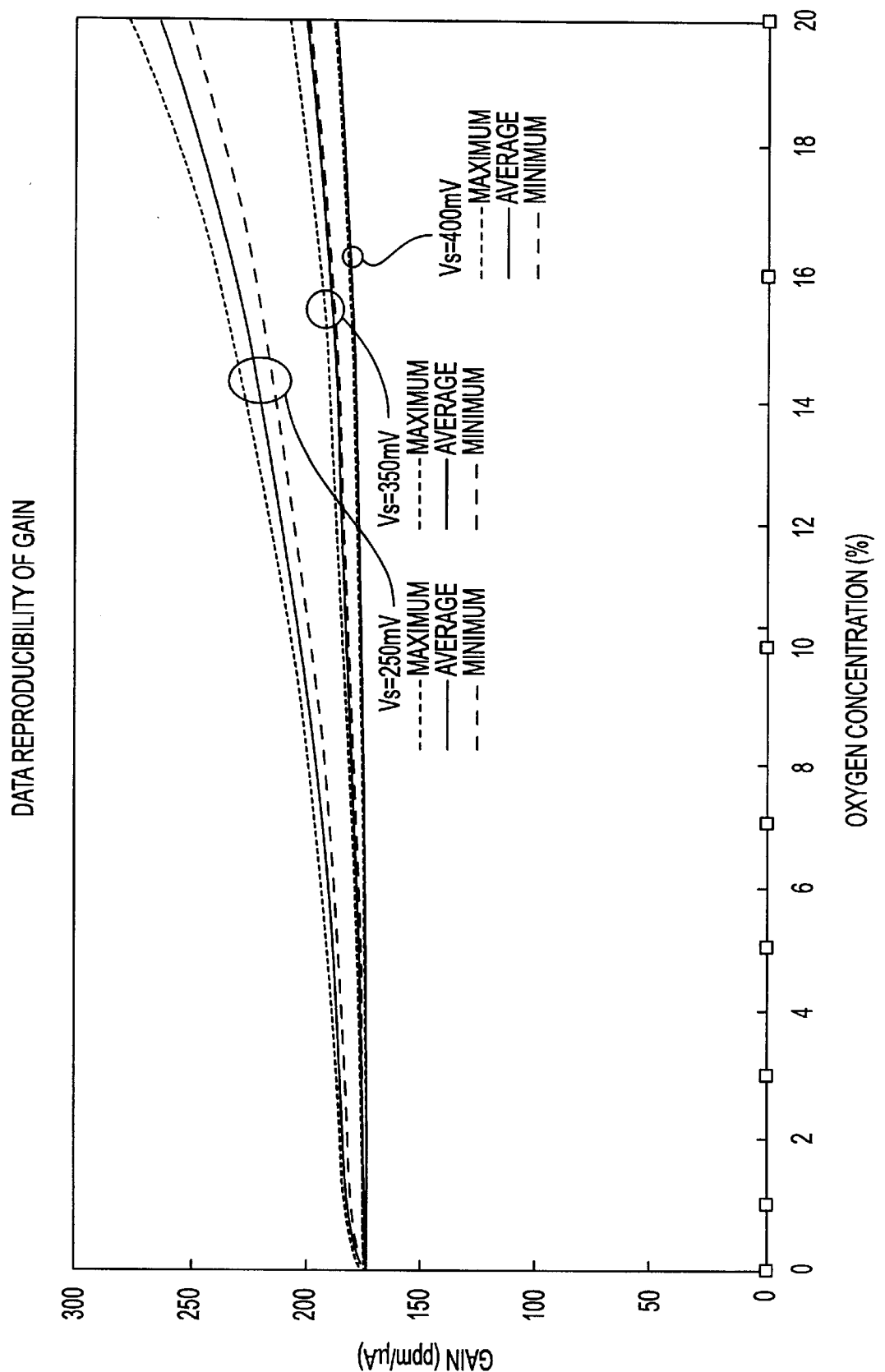
FIG. 7 is a graph showing the relationship among the target voltage Vs set for the oxygen-concentration-measuring cell, gain, and oxygen concentration of the measurement gas of interest, in the two-serial space NOx concentration sensor.

FIG. 7 shows the relationship between oxygen concentration and gain while the target voltage Vs set for the oxygen-concentration-measuring cell 7 is specified as a parameter. FIG. 7 is a detailed graph of FIG. 4 and shows the variation in gain for different values of the target voltage Vs. In FIG. 7, the solid line represents a mean gain, the dashed line represents a minimum gain, and the dotted line represents a maximum gain.

As seen from FIG. 7, when the target voltage Vs set for the oxygen-concentration-measuring cell 7 is low, the gain shows a large variation and is thus unstable. Variation in the gain increases with oxygen concentration of the measurement gas. Accordingly, the target voltage Vs is preferably set not lower than a certain value (e.g. 350 mV).

This variation in gain is considered to arise as follows. When the concentration of oxygen in the gas introduced into the second space 4 is high, the offset current Ip2offset becomes large. In this case, oxygen introduced into the second space 4 hinders sufficient dissociation of No in the second space 4. As a result, the gain varies. In such a case, accuracy in measuring NO concentration deteriorates. Therefore, the target voltage Vs is preferably set not lower than the certain value (350 mV), in order to minimize the gain variation.

Figure 5:
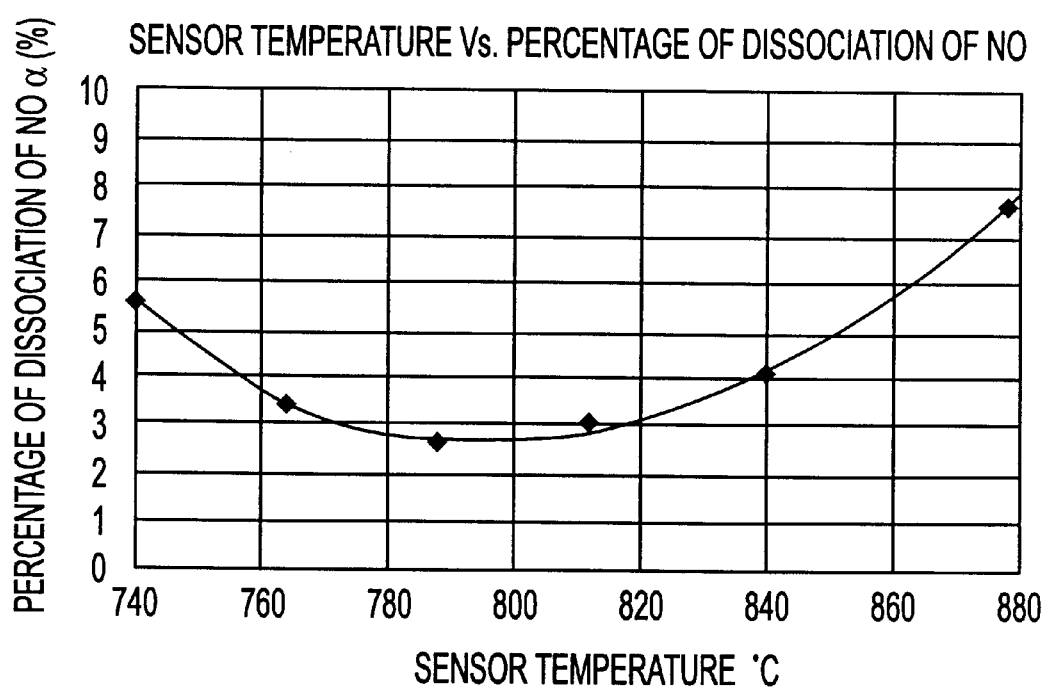
FIG. 5 is a graph showing the relationship between sensor temperature and NO dissociation percentage in a first space of a two-serial space NOx concentration sensor.

Setting the target voltage Vs not lower than a certain value means setting the percentage a of dissociation of NO in the first space 2 to not less than a certain value (0.5%). This indicates the importance of setting the percentage a of dissociation of NO in the first space 2 to a predetermined value of not less than a certain value. In other words, it is an important characteristic of the present invention that an amount of oxygen in the measurement gas is forced to decrease in the first internal space to such a low level of oxygen partial pressure of from $2\times10^{-7}$ to $2\times10^{-10}$ atm, based on the calculation with the Nernst Equation expressed by Vs=(RT/4F) ln (Pa/Pv), where T is the absolute temperature of the sensor cell, R and F are gas and Faraday constants respectively, and Pa and Pv are oxygen partial pressures at the oxygen reference electrode (7b) and the oxygen- concentration detection electrode (7a), respectively. The NO dissociation percentage α in the first internal space is preferably fixed by controlling the temperature drift of the first space 2 inside the sensor with a heater 10, because as indicated in FIG. 5 the temperature affects the dissociation percentage.

Figure 8:
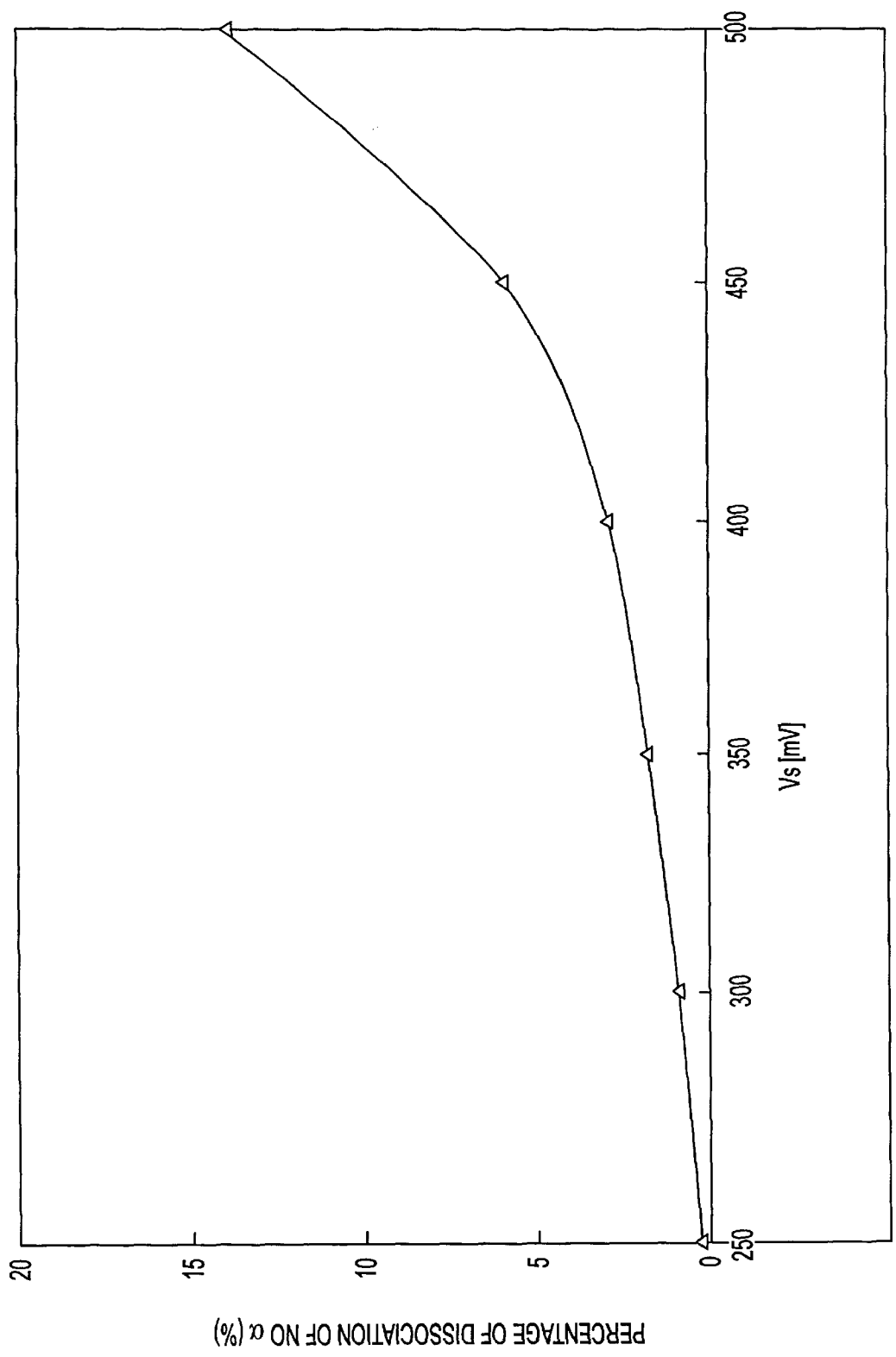
FIG. 8 is a graph showing the relationship between NO dissociation percentage and the target voltage Vs set for the oxygen-concentration-measuring cell, in the two-serial space NOx concentration sensor.
Figure 9A:
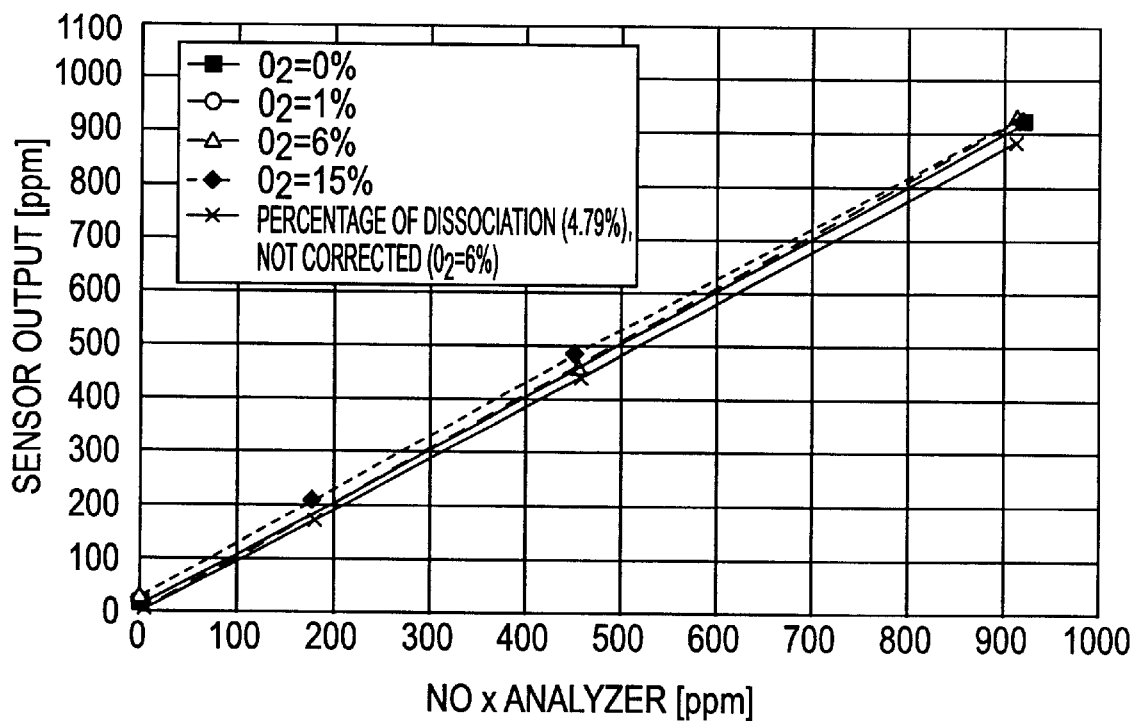
FIGS. 9a and 9b are graphs showing the output state of an NOx concentration sensor relative to a certain NO dissociation percentage, in the two-serial space NOx concentration sensor.
Figure 9B:
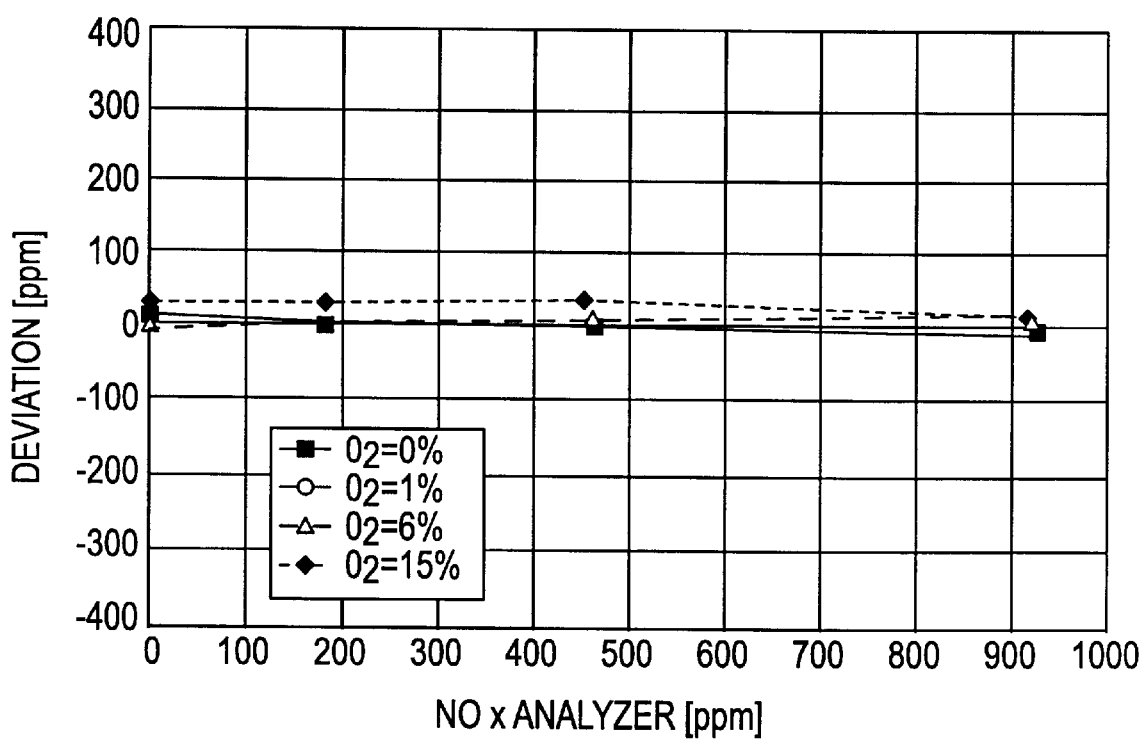
Figure 10A:
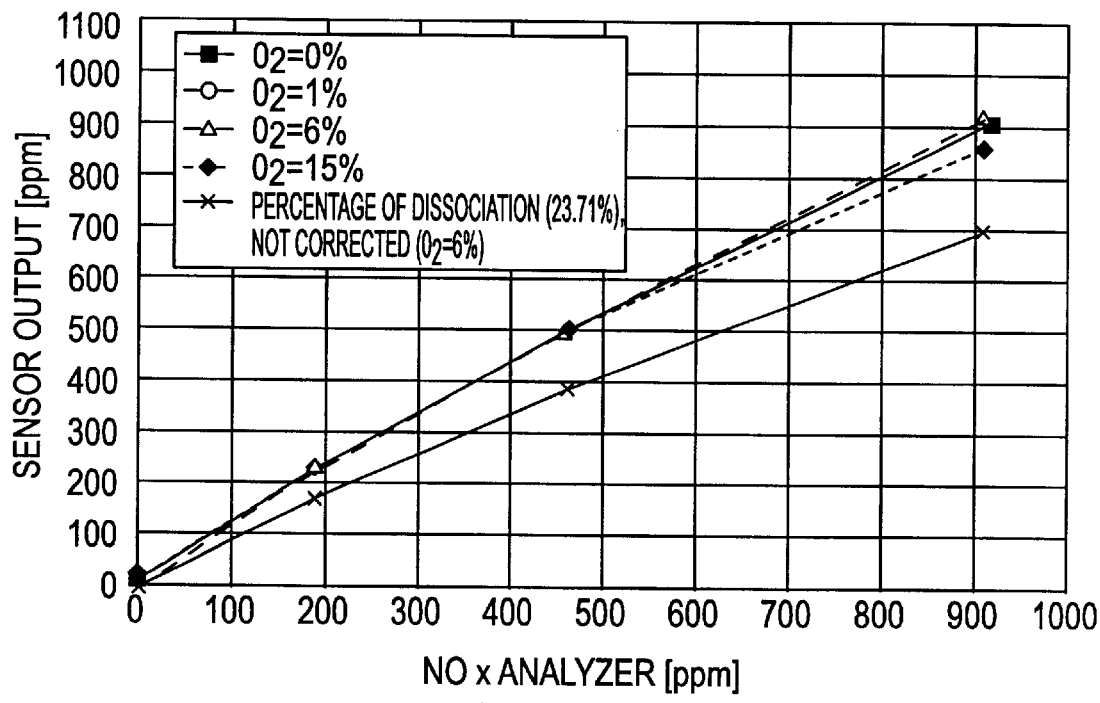
FIGS. 10A and 10B are graphs showing the output state of the NOx concentration sensor relative to a certain NO dissociation percentage, in the two-serial space NOx concentration sensor.
Figure 10B:
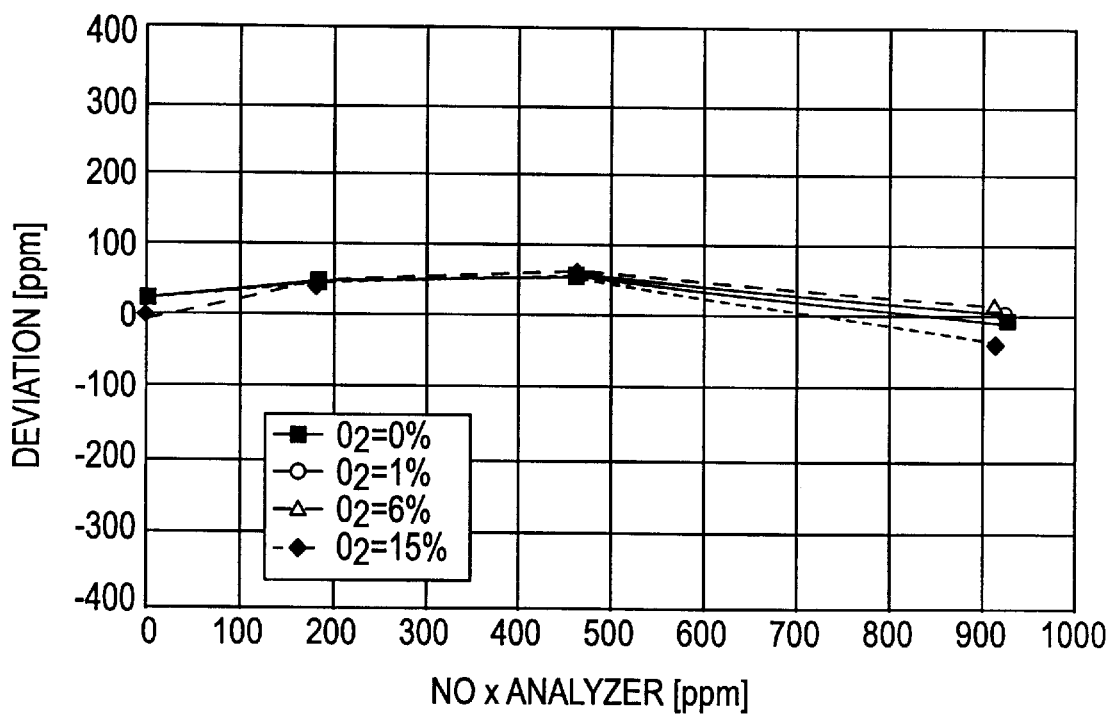
Figure 11A:
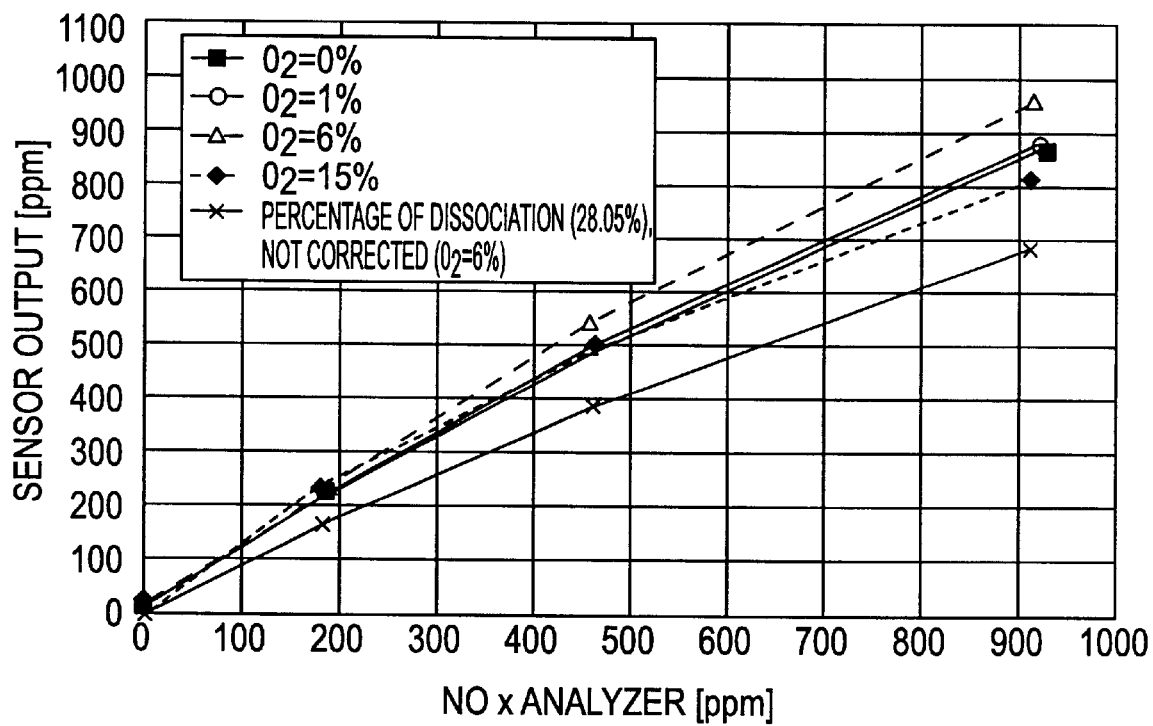
FIGS. 11A and 11B are graphs showing the output state of the NOx concentration sensor relative to a certain NO dissociation percentage.
Figure 11B:
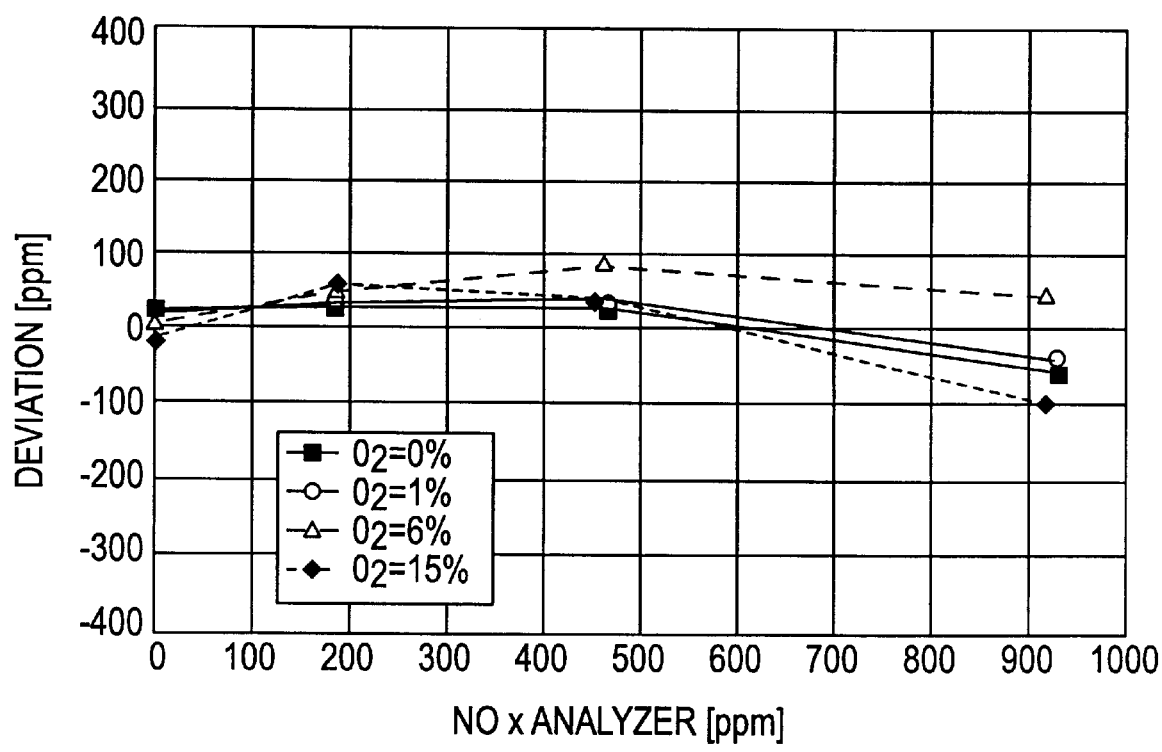
Figure 12A:
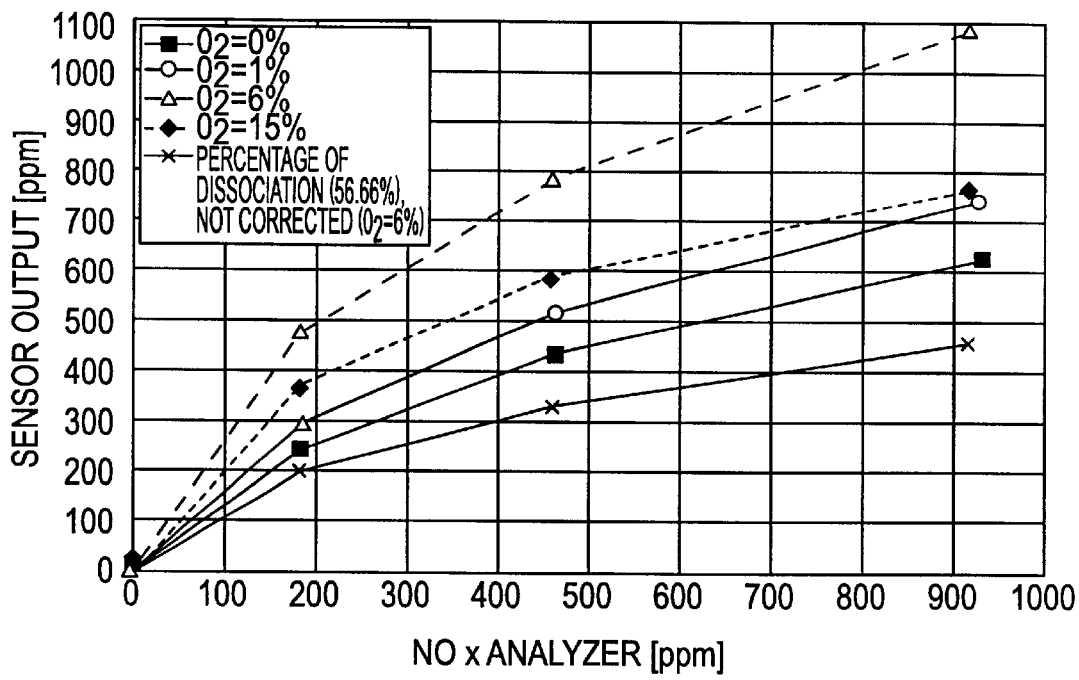
FIGS. 12A and 12B are graphs showing the output state of the NOx concentration sensor relative to a certain NO dissociation percentage.
Figure 12B:
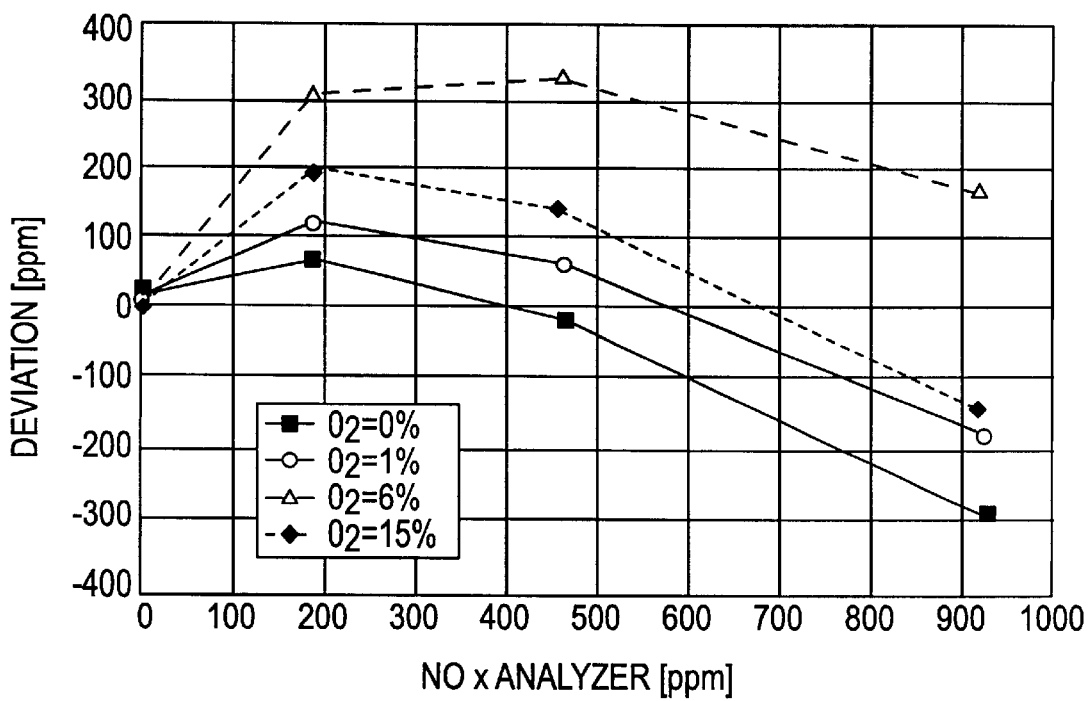

Specifically, the percentage α of dissociation of NO and the target voltage Vs set across the electrodes 7a, 7b of the oxygen-concentration-measuring cell 7 have the relationship shown in FIG. 8. Thus, setting the target voltage Vs not lower than a certain value (e.g., 350 mV) means setting the percentage α of dissociation of NO to not less than a certain value (0.5%).

Accordingly, by setting the percentage a of dissociation of NO to not less than a certain value (for example, at least 2%), variation in gain is decreased, thereby improving accuracy in measuring NO concentration.

The upper limit of the NO dissociation percentage will next be described.

Figure 13:
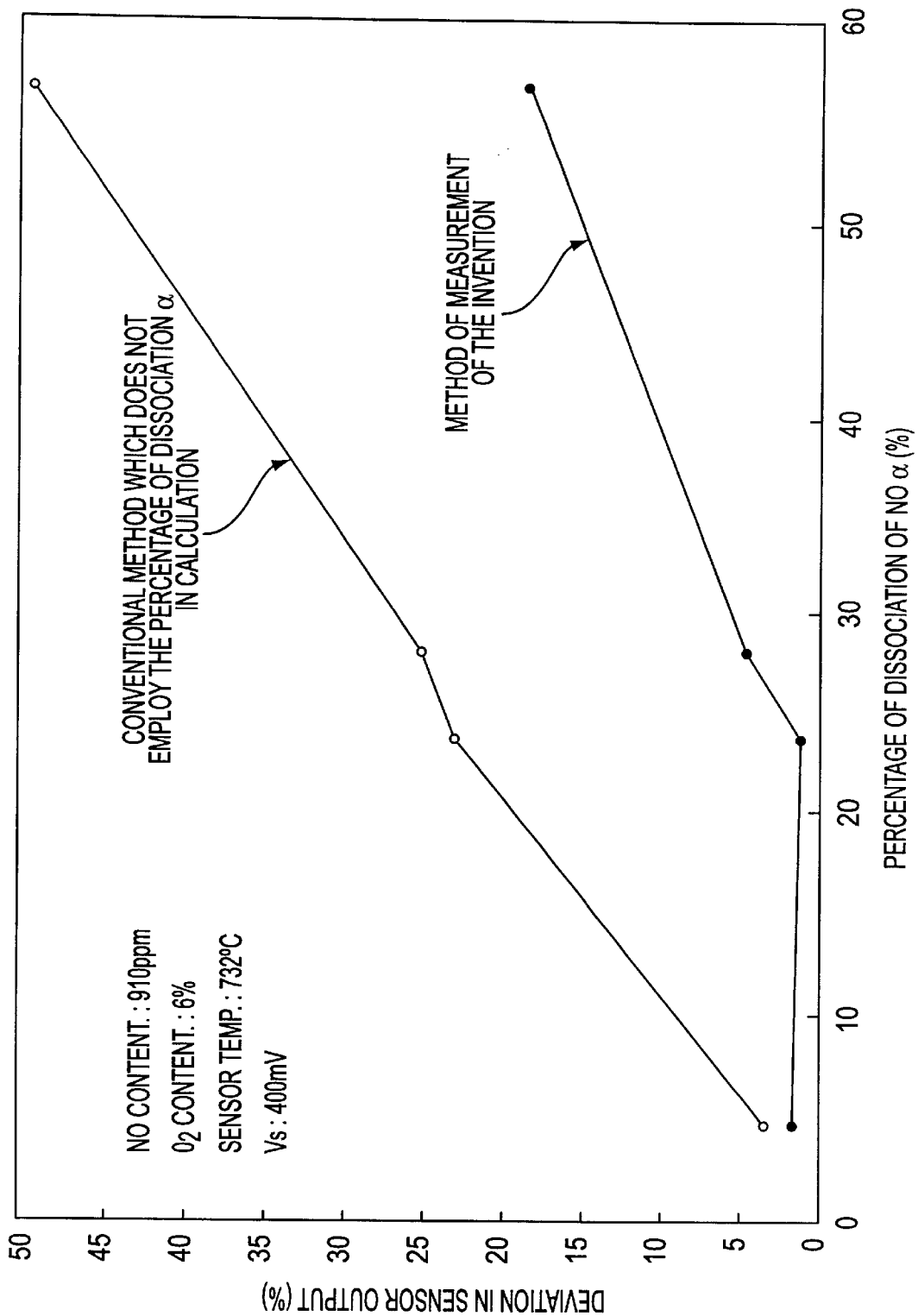
FIG. 13 is a graph showing the relationship between deviation in sensor output from the NOx concentration and NO dissociation percentage, proposing the NO dissociation percentage range used in the method and apparatus according to the present invention.
Figure 14:
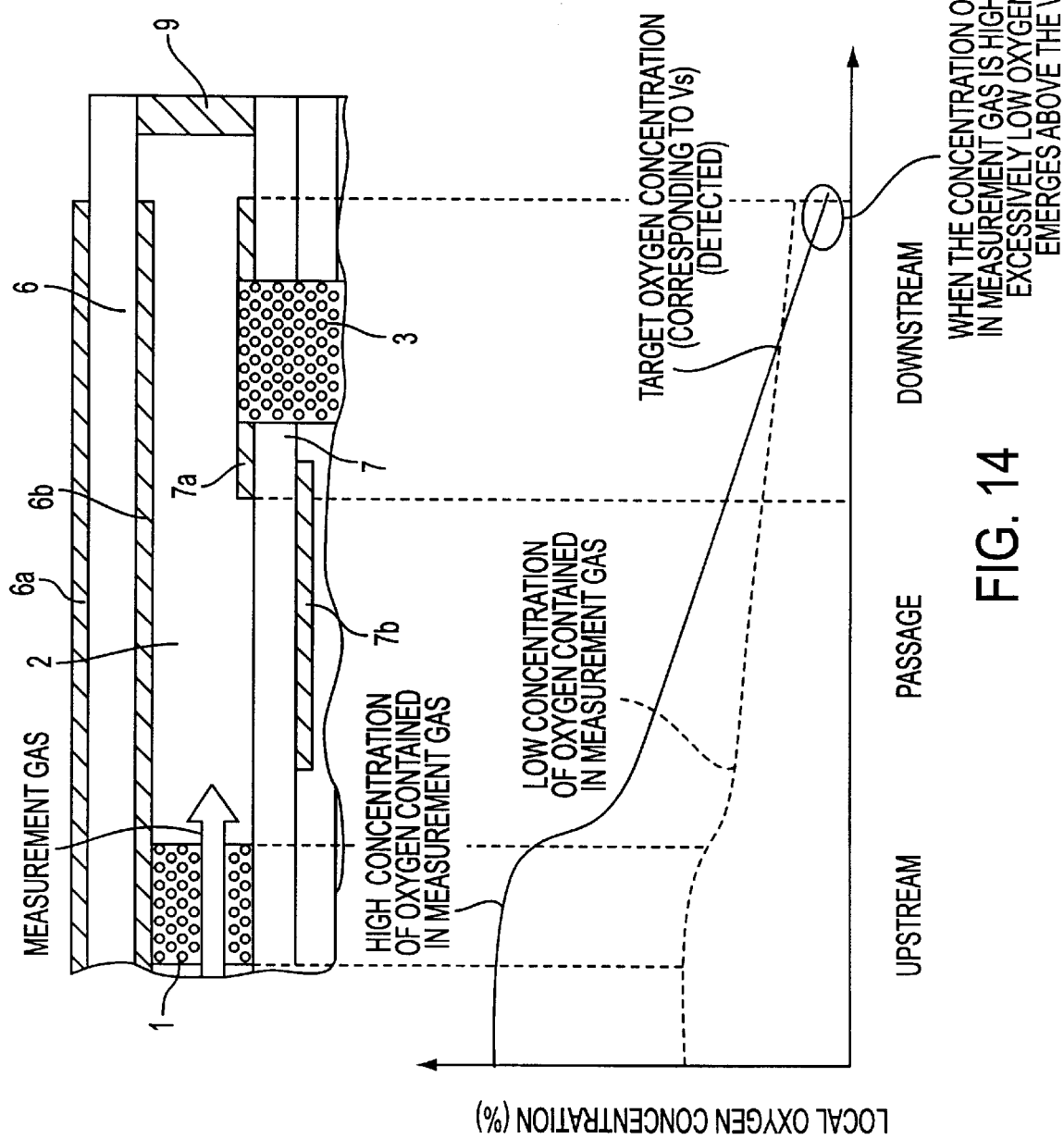
FIG. 14 is an explanatory view illustrating the principle of NO dissociation in a first internal space (first passage) of the two-serial space NOx concentration sensor, according to one of the aspects according to the present invention.
Figure 15:
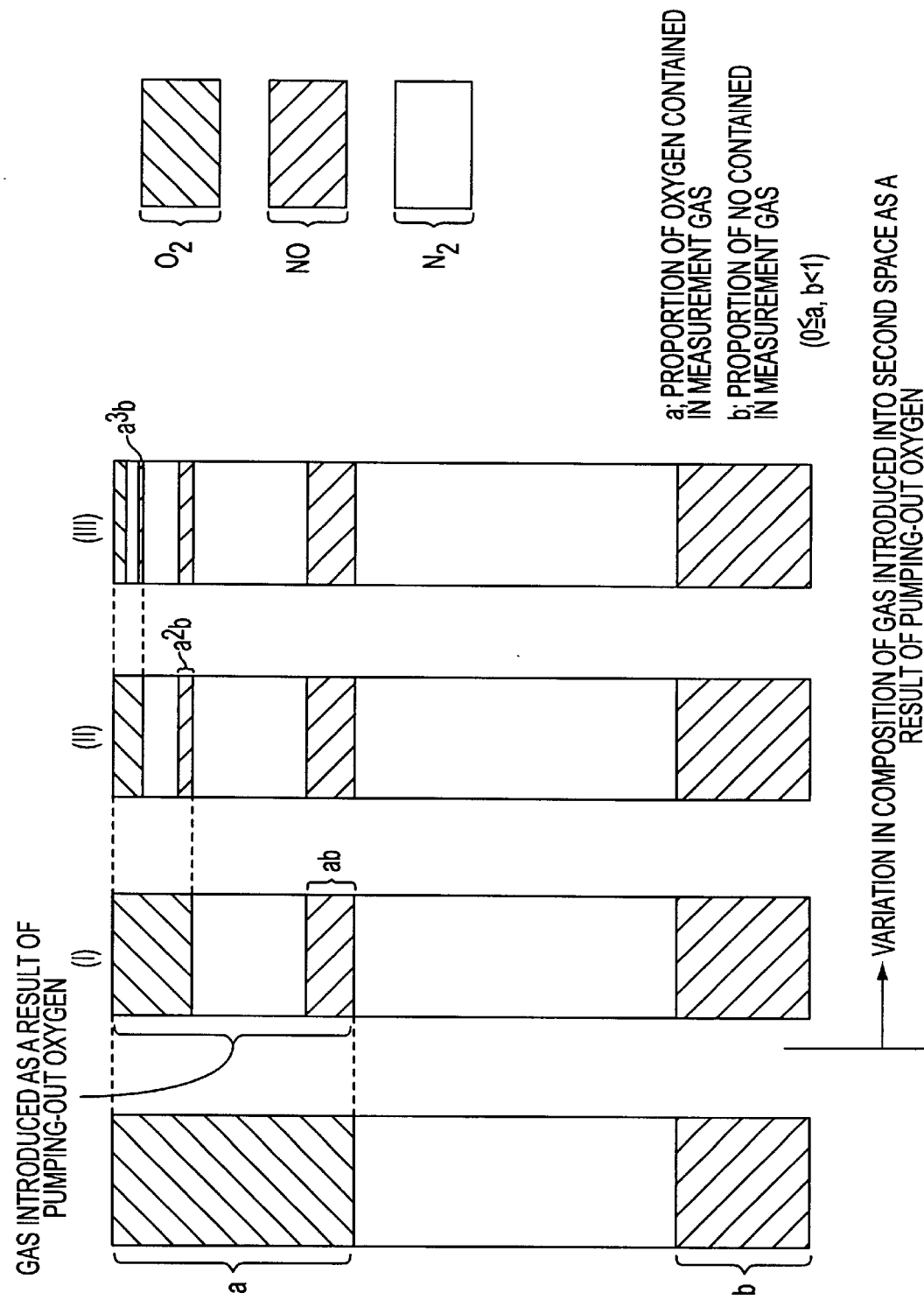
FIG. 15 is an explanatory view illustrating the state of variation in the composition of the gas at the entrance of a second internal space (second passage) before entering the second internal space of the two-serial space NOx concentration sensor.

The NO dissociation percentage is preferably, for example, not less than 0.5%. However, although the gain variation is decreased, too high a NO dissociation percentage raises a problem in obtaining the gain itself. Therefore, the NO dissociation percentage is most preferably not greater than a certain value, which would be about 20% as shown in FIG. 13.

FIGS. 9 to 12 show the results of experiments on sensor output. The experiments used NOx sensors having a porous electrode having different Au contents and Pt as a main component to thereby impart a percentage α of dissociation of NO of 4.4%, 23.7%, 28.1% and 56.7% to the respective sensors. In the experiments, sensor output was measured at an oxygen concentration of 0%, 1%, 6% and 15%. FIG. 9A, FIG. 10A, FIG. 11A and FIG. 12A show the relationship between the sensor output indicative of NO concentration and the actual NO concentration, for each of the oxygen concentrations. FIG. 9B, FIG. 10B, FIG. 11B and FIG. 12B show the relationship between deviation in sensor output and the actual NO concentration, for each of the oxygen concentrations.

The NOx analyzer used in the experiments employed a known Chemical Luminescence Detection or CLD method. In the experimental results, the NOx analyzer output is referred to as the actual NO concentration.

As seen from FIGS. 9 to 11, at a percentage α of dissociation of NO of 4.4%, 23.7% and 28.1%, there was a small deviation in sensor output from the actual NO concentration. By contrast, as shown in FIG. 12, at a percentage α of dissociation of NO of 56.7%, there was a large deviation in sensor output from the actual NO concentration.

The graph of FIG. 13 summarizes the experimental results of FIGS. 9 to 12. As seen from FIG. 13, when the NO dissociation percentage is too large, deviation in sensor output becomes large, and consequently accuracy in measuring NO concentration deteriorates. The case of FIG. 13 employed an NO concentration, $O_2$ concentration, sensor temperature and voltage (Vs) as specified therein.

Thus, the NO dissociation percentage is preferably not greater than 50%, more preferably not greater than 30%, particularly preferably not greater than 20%.

The above example must not be construed as limiting the invention. Variations and modifications are possible without deviating from the gist of the invention.

For example, the air having 0.2 atm oxygen partial pressure may be introduced to the NOx concentration cell reference electrode instead of using such an oxygen self-generation-type reference electrode for a reference oxygen space. A pair of electrodes of the second pumping cell may be formed on opposite surfaces of the solid electrolyte layer of the cell at opposite positions. Also, one or more heaters may be preferably disposed on a single side or both sides of the NOx concentration sensor so as to control the sensor temperature drift as small as possible in the predetermined temperature of 550° C to 900° C.

Because the NO dissociation percentage in the first space varies with sensor temperature as shown in FIG. 5, the NOx concentration sensor is preferably used within a temperature range in which the NO dissociation percentage does not vary greatly, for example, a range of 700° C. to 850 C, preferably a range of 770° C. to 820° C. The temperature of the sensor used in the present invention is kept constant during NOx concentration measurement.

For further clarification of an embodiment of the present invention, an apparatus for measuring NOx concentration according to an embodiment of the invention and a method for measuring NOx concentration employing the apparatus will next be described. Using the NOx concentration sensor as may be shown in FIGS. 18 and 19, the concentration of NOx contained in a measurement gas is measured while the sensor is controlled as described above. In the experiments described below, NO is selected as a nitrogen oxide to be measured; the sensor-element temperature of the NOx concentration sensor is 800° C.; and the temperature of the measurement gas introduced into the sensor is 300° C. Vp2 applied between the two electrodes of the second pumping cell is 450 mV.

EXPERIMENT 1

Figure 23:
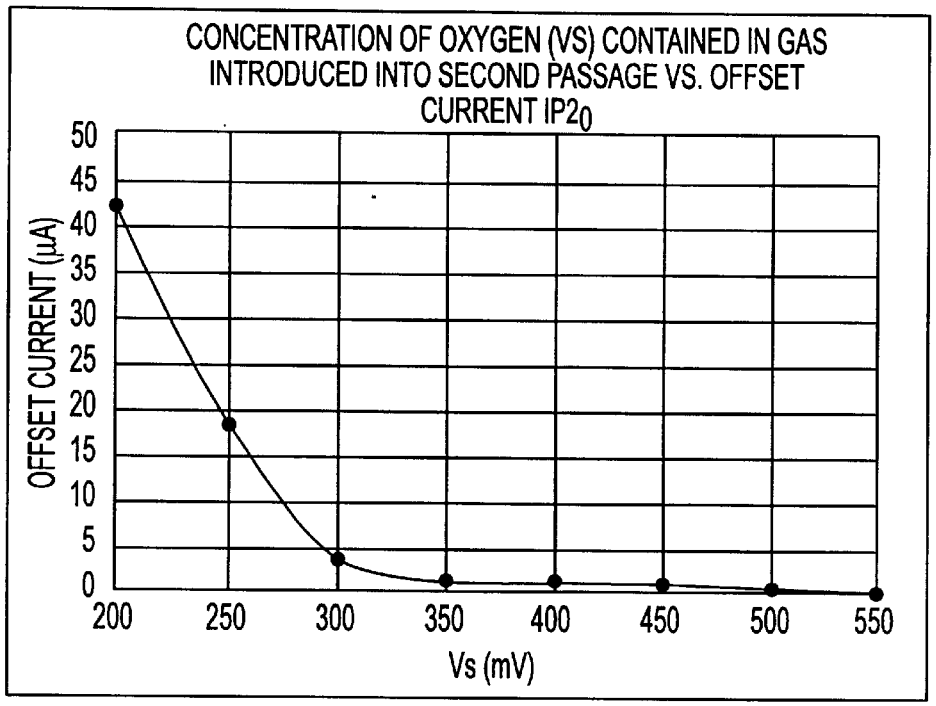
FIG. 23 is a graph showing measurement results of Experiment 1, showing the offset current for Ip2 as a function of the target voltage value Vs.
Figure 24:
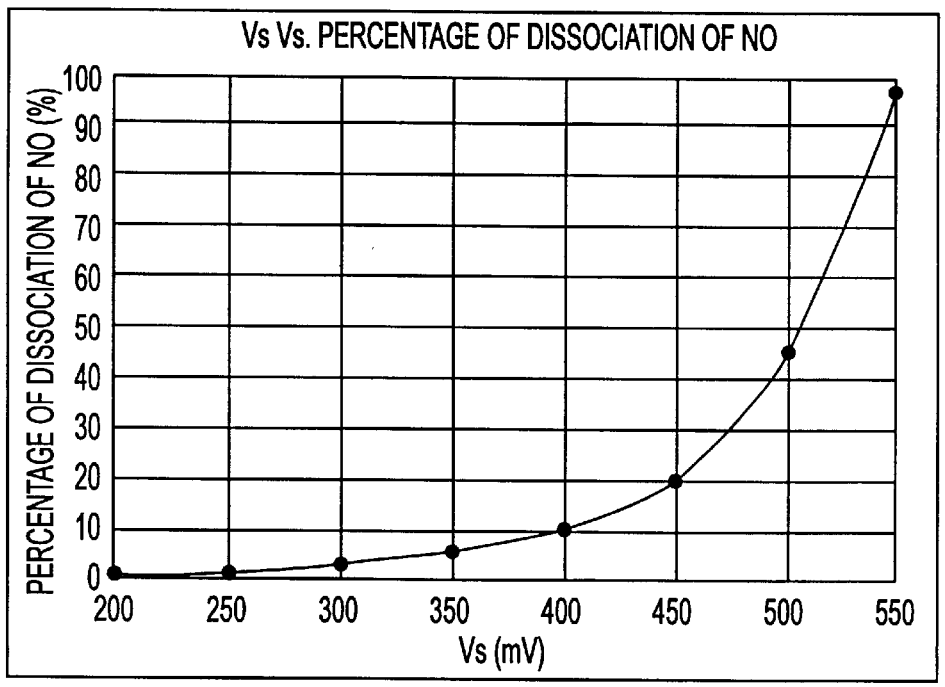
FIG. 24 is a graph showing measurement results of Experiment 1, showing the NO dissociation percentage in the first internal space as a function of Vs which corresponds to an oxygen partial pressure of the first internal space gas entering the second internal space.

The measurement gas has an oxygen concentration of 7%, a $CO_2$ concentration of 10%, and an $H_2O$ concentration of 10%. The relationship between the voltage Vs set for the oxygen-concentration-measuring cell and the offset current ($Ip2_2$) of the second pumping current Ip2 is examined. The results are shown in FIG. 23. When Vs is set high, the concentration of oxygen in the gas diffusing into the second passage decreases. By contrast, when Vs is set low, the concentration of oxygen in the gas diffusing into the second passage increases. FIG. 24 shows the relationship between Vs and the NO dissociation percentage in the first passage. As seen from FIG. 24, when Vs is high, namely, when oxygen concentration is low, the NO dissociation percentage is large. The method for calculating the percentage of NO will be described below.

As seen from FIG. 23, in order to decrease the offset current component of the second pumping current for decreasing the oxygen concentration dependence and temperature dependence of the NOx concentration measurement, Vs is preferably set to not less than 300 mV, more preferably not less than 320 mV. As seen from FIG. 24, in order to stabilize the NO dissociation percentage in the first passage, Vs is preferably set to not greater than 500 mV. Vs is more preferably set to not less than 350 mV and not greater than 450 mV. The most preferable Vs range is from about 400 mV to about 450 mV, because there starts to appear a substantial influence from moisture dissociation when Vs exceeds 450 mV particularly beyond 500 mV and that range renders the best NOx measurement accuracy.

EXPERIMENT 2A: MEASURED GAIN FOR NOx CONCENTRATION

Figure 25:
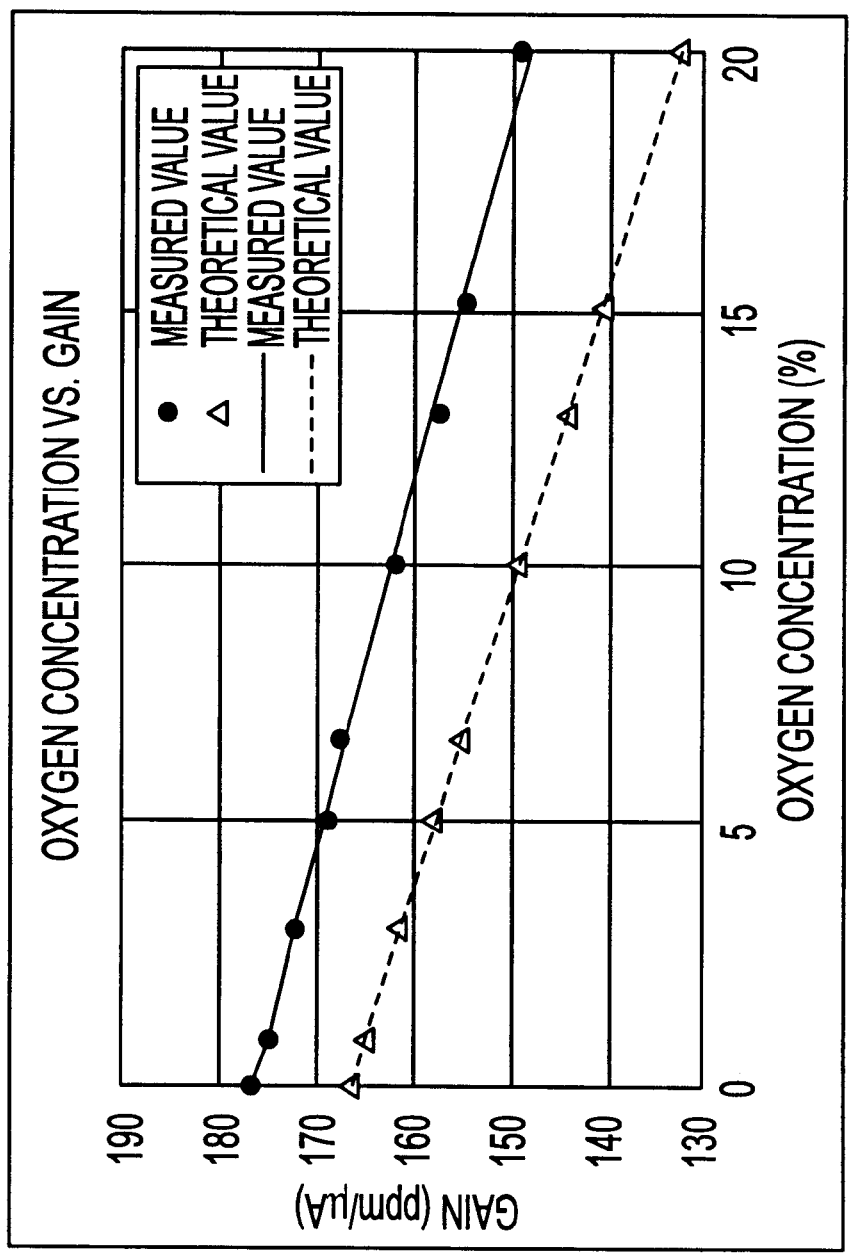
FIG. 25 is a graph showing measurement results of Experiment 2a, showing Gain of the two-serial NO sensor as a function of a oxygen concentration of the measurement gas of interest in a measurement space.

Ip2 is measured under the following conditions: Vs=350 mV; oxygen concentration =varied; NO concentration=0 ppm and 1,500 ppm. Gain K in NOx concentration is obtained from the difference between Ip2 measured at an NO concentration of 1,500 ppm and Ip2 measured at an NO concentration of 0 ppm. The solid line of FIG. 25 represents the relationship between the thus-obtained gain K (measured gain) and oxygen concentration. Based on the relationship thus obtained, coefficients K0 and K1 in equation (2) shown previously are obtained, thereby deducing equation (7) shown below. Notably, a Vs of 350 mV corresponds to an average partial pressure of oxygen of about $2\times10^{-7}$ as measured at the oxygen concentration detection electrode, if the detection electrode is paired with a counter electrode referencing to the atmosphere having an oxygen partial pressure of $2\times10^{-0}$, according to the Nernst Equation.

$$\text{Measured K }[\text{ppm}/\mu A]=176.05-1.3564\times O_2\,[\%] \tag{6}$$

Substituting this into equations (1) and (2) gives $$\text{NO concentration}=\{176.05-1.3564\times O_2\,[\%]\}\times\Delta Ip2 \tag{7}$$

EXPERIMENT 2B: THEORETICAL GAIN FOR NOx CONCENTRATION

Assuming that NO does not dissociate in the first passage, gain K in NOx concentration as obtained while taking into account oxygen pumped out from the first passage is represented by equation (8) shown below (see step 205 in FIG. 16). The dotted line of FIG. 25 represents the relationship between oxygen concentration and theoretical gain K that is obtained assuming that NO does not dissociate in the first passage. A theoretical gain at an oxygen concentration of 0% was obtained based on gain K0 (gain as measured when NO dissociates in the first passage) as measured at a measurement gas/oxygen concentration of 0% and a percentage α of dissociation of NO of 0% at an oxygen concentration of 0%. A method for calculating α0 will be described below.

$$\text{Theoretical K }[\text{ppm}/\mu A]=K0/(1-\alpha 0)\times(1-O_2[\%]/100) \tag{8}$$

As seen from a comparison between measured gain K (solid line) and theoretical K (dotted line) shown in FIG. 25, the measured gain decreases to a lesser degree (namely, sensitivity increases to a lesser degree) in relation to an increase in oxygen concentration as compared with the theoretical gain. That is, the actual increase in concentration (enrichment) of NO in the first passage, which increase occurs as a result of pumping out oxygen from the first passage, is smaller than the theoretical increase. This indicates that NO can dissociate partially and stably in the first passage of the sensor.

Equation (2) shown previously represents gain K in NOx concentration taking into account the enrichment of NO derived from pumping out oxygen from the first passage and the effect of the dissociation of NO in the first passage. Equation (3) shown previously represents NOx concentration, taking into account the enrichment of NO derived from pumping out oxygen from the first passage and the effect of the dissociation of NO in the first passage.

K0 and K1 appearing in equation (3) were obtained by Experiment 2A, and offset Ip2, was obtained by Experiment 1. Thus, the concentration of oxygen in the measurement gas is next obtained. In order to obtain the oxygen concentration based on the first pumping current Ip1, the NO dissociation percentage in the first passage is obtained.

EXPERIMENT 3A: NO DISSOCIATION PERCENTAGE AND DETERMINATION OF IB

Figure 26:
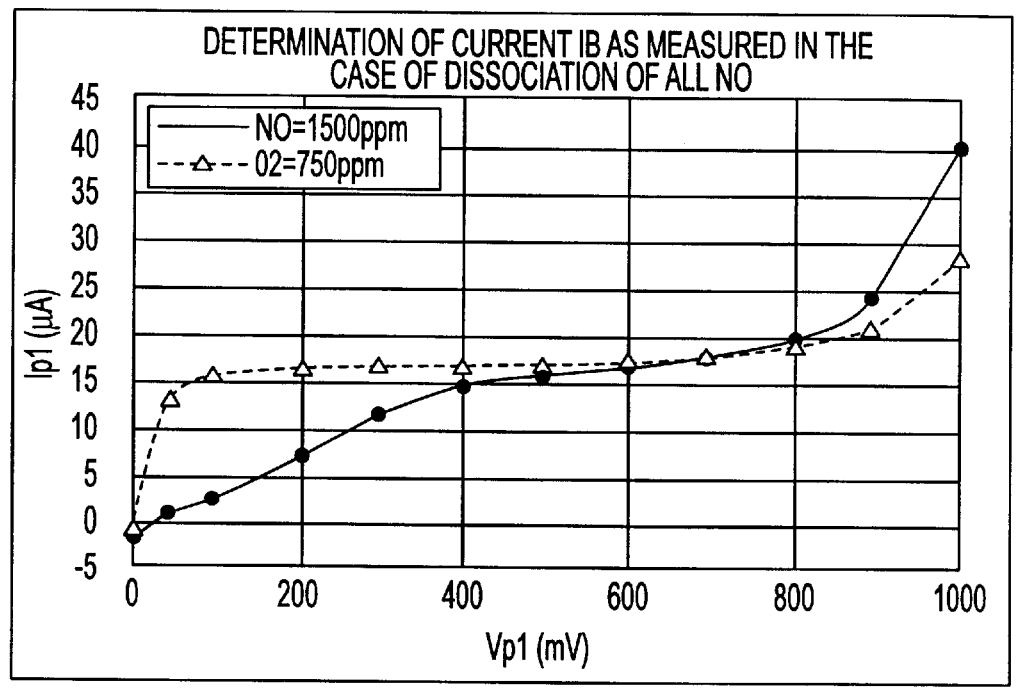
FIG. 26 is a graph showing measurement results of Experiment 3a, used in determination of the NO dissociation percentage in the first internal space.

The composition of a measurement gas is as follows: NO=1,500 ppm; and balance =nitrogen. While the voltage Vp1 applied to the first pumping cell is varied, Ip1 is measured. The results are shown in FIG. 26. Ip1 in a stable region where variation in Ip1 is small in relation to variation in Vp1 corresponds to IB (see the note on K of Equation (5) shown previously). As seen from FIG. 26, when all NO (1,500 ppm) dissociates at an oxygen concentration of the measurement gas of 0%, IB (Vp1=600 mV) is 18.32 $\mu A$. Accordingly, K5=18.32 $\mu A$/1,500 ppm.

EXPERIMENT 3B: NO DISSOCIATION PERCENTAGE AND DETERMINATION OF Ib

Figure 27:
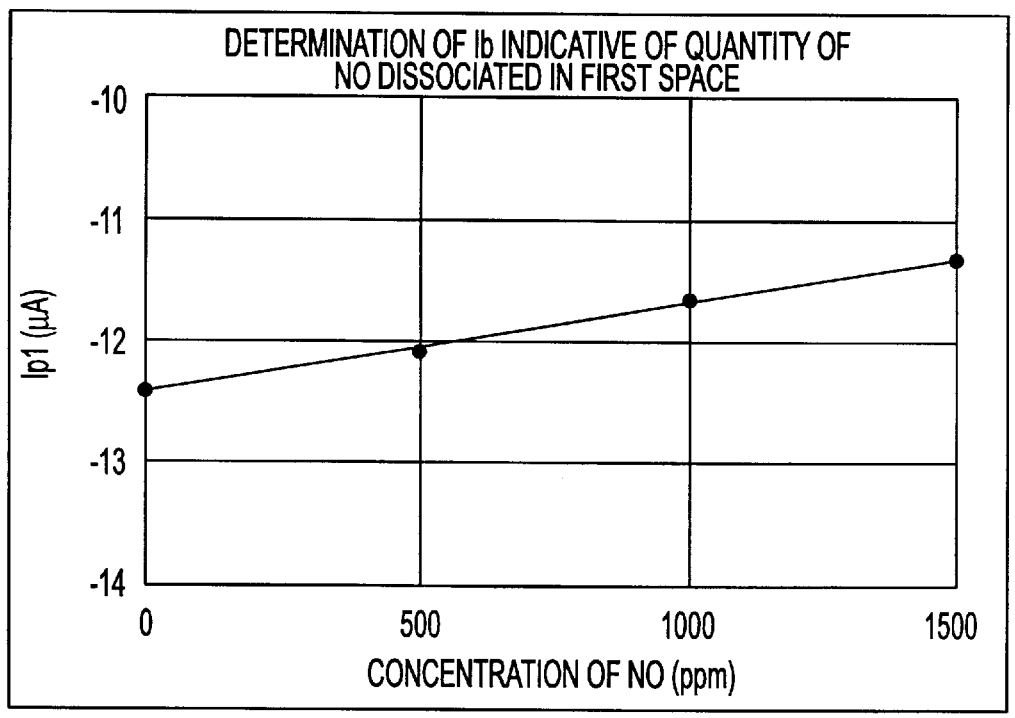
FIG. 27 is a graph showing measurement results of Experiment 3b, used in determination of the NO dissociation percentage in the first internal space.

The composition of a measurement gas was as follows: NO=0,500, 1,000, 1,500 ppm; and balance=nitrogen. While control was performed such that Vs assumes a value of 350 mV, Ip1 is measured for an NO concentration of 0,500, 1,000 and 1,500 ppm. The results are shown in FIG. 27. The difference between Ip1 as measured at a predetermined No concentration and Ip1 as measured at an NO concentration of 0 ppm is the current Ib generated by the dissociation of NO. For example, Ib at an NO concentration of 1,500 ppm is obtained as follows: Ip1[1500 ppm]−Ip1[0 ppm]=1.05 $\mu A$. Accordingly, at an oxygen concentration of the measurement gas of 0%, the NO dissociation percentage in the first passage is calculated as follows: Ib/IB=1.05/18.32×100= 5.73%.

The reason why the vertical axis of the graph of FIG. 27 is negative is described as follows. In Experiment 3B, the concentration of oxygen in the measurement gas is taken as 0%. Accordingly, in order to maintain Vs at 350 mV (corresponding to an average partial pressure of oxygen of about $2\times10^{-7}$ atm as measured on the oxygen concentration detection electrode), oxygen is introduced into the first passage by means of the first pumping cell. Accordingly, Ip1 flows in a direction opposite that of the normal state in which the measurement gas contains oxygen.

EXPERIMENT 3C: CALCULATION OF THE NO DISSOCIATION PERCENTAGE AT AN OXYGEN CONCENTRATION OF OTHER THAN 0%

The difference between the measured gain K in NOx concentration as measured at a certain oxygen concentration and the theoretical gain K as obtained theoretically corresponds to the quantity of NO dissociated in the first passage at the subject oxygen concentration. In other words, there is a relationship as expressed in the following equation (9), where the theoretical K is a gain value determined under the condition that NO does not dissociate at all in the first passage, the measured K is a gain value actually determined under the condition that NO dissociates substantially in part in the first passage.

NO dissociation percentage={(measured K)−(theoretical K)}/(measured K)  (9)

Thus, based on the difference between the measured gain K and the theoretical gain K as shown in FIG. 25, the NO dissociation percentage in the first passage is determined in relation to oxygen concentration in the measurement gas of interest. The results are shown in FIG. 28.

Figure 28:
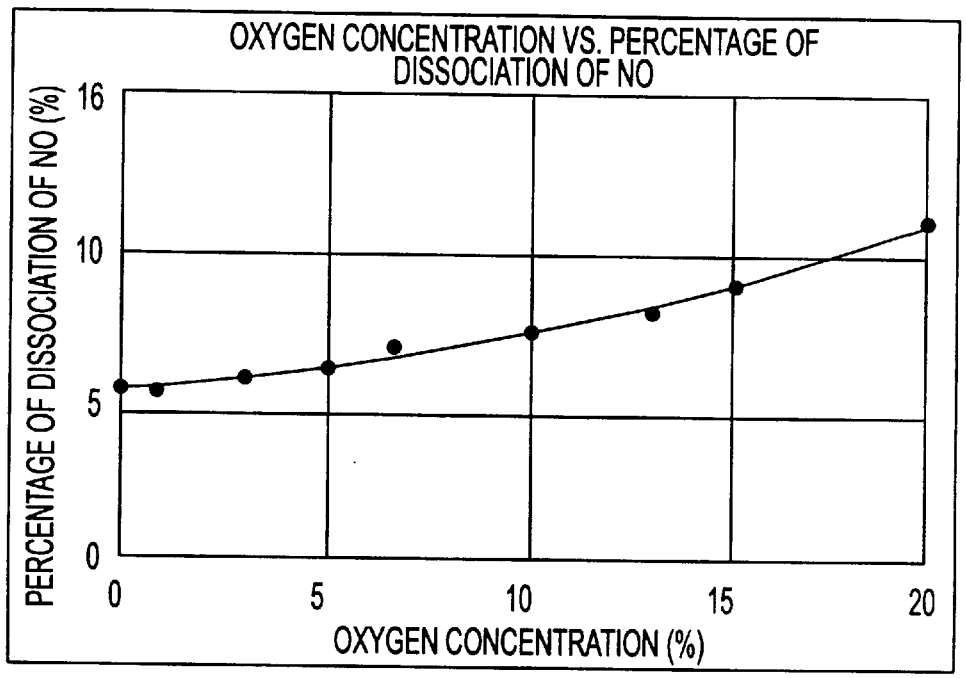
FIG. 28 is a graph showing measurement results of Experiment 3 c, showing NO dissociation percentage in the first internal space as a function of oxygen concentration of the measurement gas of interest entering the first internal space.

The relationship between oxygen concentration and the NO dissociation percentage shown in FIG. 28 can be represented by expression or rather equation (4) shown previously. By substituting experimentally obtained K2 and K3 into equation (4), equation (10) shown below is obtained.

NO dissociation percentage=(5.695+0.106×$O_2$[%]+0.008×$O_2$[%]$^2$)/100.  (10)

EXPERIMENT 4: K4 AND $IP1_0$

Figure 29:
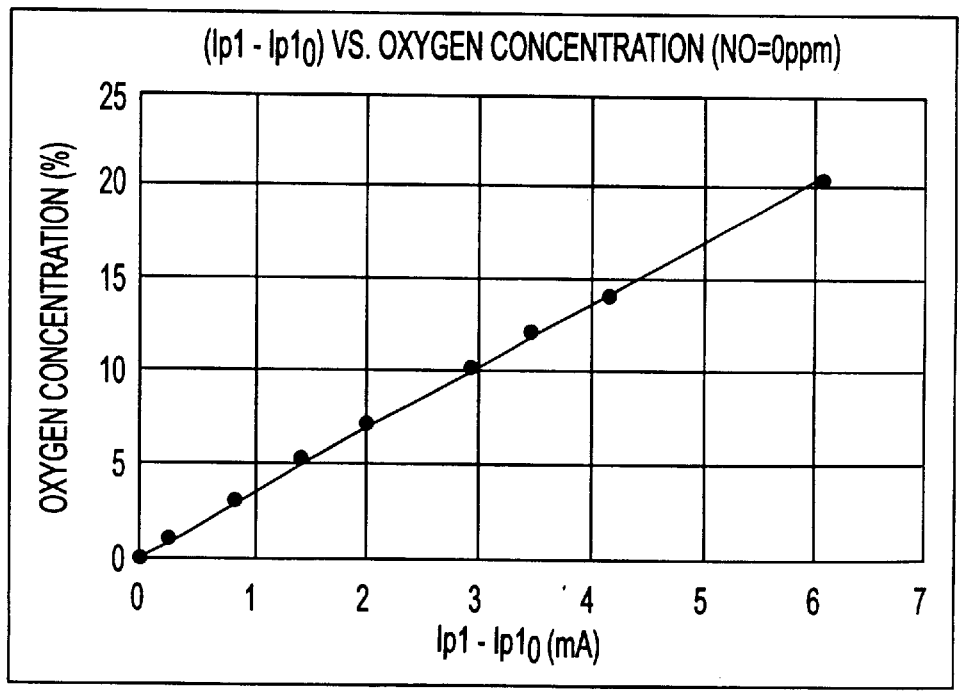
FIG. 29 is a graph showing measurement results of Experiment 4, showing that an oxygen concentration of the measurement gas is represented as a linear function of the first pump cell current Ip1 only when the measurement gas of interest does not contain NOx but only oxygen.

Using a measurement gas having an NO concentration of 0 ppm, Ip1 was measured while the oxygen concentration is varied. The results are shown in FIG. 29. Based on these results, K4 and $Ip1_0$ appearing in Equation (5) shown previously are obtained. By substituting the thus-obtained K4 and $Ip1_0$ as well as the previously obtained NO dissociation percentage and other factors into equation (5), equation (11) shown below is obtained.

$O_2$[%]=K4×{(Ip1−18.32×10$^{-3}$×[mA]/1500 ppm ×(NO concentration)×(5.695+0.106×$O_2$[%]+0.008

×$O_2$[%]$^2$)/100−0.037}=3.345×{(Ip1−1.221×10$^{-5}$×(NO concentration)×(5.695+0.106×$O_2$[%]+0.008 ×$O_2$[%]$^2$)/100−0.037}  (11)

Calculation Example According to the Example of the Invention

By substituting measured Ip1 and Ip2 into equations (7) and (11) and then solving their simultaneous system, NOx concentration and oxygen concentration are obtained based on Ip1 and Ip2.

Calculation Example According to the Comparative Example

For comparison, a gain (176.6 ppm/μA) at an oxygen concentration of 0% is used as gain K. This fixed gain and Ip2 are substituted into equation (1) so as to obtain NOx concentration. In this Comparative Example, NOx concentration is obtained based on Ip2.

Comparison in Accuracy

Using a measurement gas having an NO concentration of 1,500 ppm and different oxygen concentrations, a calculated No concentration and an actual NO concentration (charged NO concentration) are compared between the Example of the invention and the Comparative Example. The results are shown in Table 1. Notably, accuracy[%]={1500[charged NO concentration]−(calculated NO concentration)}/1500 [charged NO concentration]×100. As seen from Table 1, according to the calculation of the Example (corrected) based on Ip1 and Ip2, accuracy in measurement of NO concentration is within 1% even when the oxygen concentration is varied. By contrast, according to the calculation of Comparative Example based on Ip2 only (not corrected), the measurement accuracy deteriorates with an increase in oxygen concentration.

TABLE 1

| Oxygen conc. [%] | Charged NO conc. = 1500 ppm | | Calculated oxygen conc. [%] | Calculated NO conc. [ppm] | | Measured accuracy [%] | |
|---|---|---|---|---|---|---|---|
| | IP1 [mA] | ΔIP2 [μA] | | Corrected | Not corrected | Corrected | Not corrected |
| 0 | 0.038 | 8.49 | 0.0 | 1495 | 1500 | 0.3 | 0.0 |
| 10 | 2.957 | 9.26 | 9.8 | 1507 | 1635 | −0.5 | −9.0 |
| 20 | 6.146 | 10.02 | 20.4 | 1486 | 1769 | 0.9 | −17.9 |

EXPERIMENT 5: ELECTRODE MATERIAL AND NO DISSOCIATION PERCENTAGE

Figure 30:
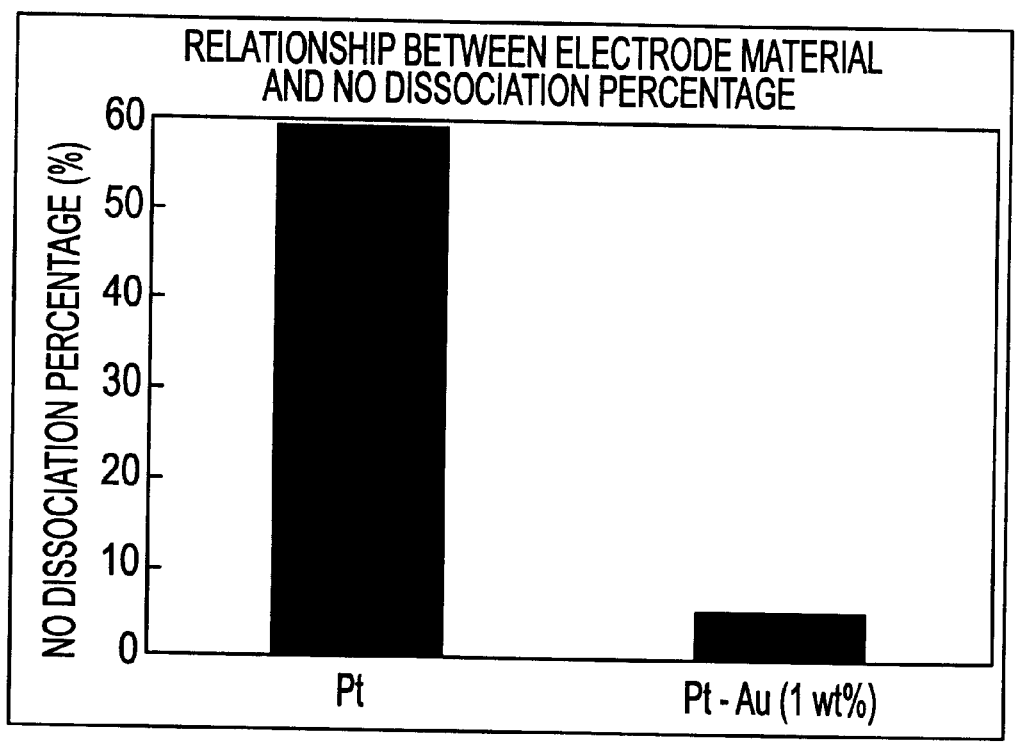
FIG. 30 is an explanatory view illustrating the relationship between the inner electrode material of the first pump cell and the NO dissociation percentage in the first internal space.

The composition of a measurement gas is as follows: NO=1,500 ppm; oxygen concentration=0%; and balance=nitrogen gas. Using the measurement gas, the relationship between the NO dissociation percentage and the composition of material for the first pumping cell electrode exposed to the first passage is examined. The results are shown in FIG. 30. As seen from FIG. 30, the NO dissociation percentage in the first passage differs according to the composition of the electrode material. Thus, by selecting an appropriate electrode material composition, the NO dissociation percentage in the first passage can be optimized.

Au and/or Cu is preferably added to Pt in an amount of 0.1% by weight to several % by weight or 0.5% by weight to 3% by weight, to thereby control or rather stabilize the NO dissociation percentage to a constant value of from 0.5% to 20% or of 2% to 15%, respectively, for maintaining oxygen concentration of the gas entering the second passage (second space) to a lowest value under Vs control.

Effects of the Invention

As described above, according to the method for measuring the concentration of NOx in a measurement gas of the present invention as well as the NOx concentration sensor of the invention, while oxygen concentration in the vicinity of the gas inlet of the second space is decreased such that a portion of NO dissociates in the first space, NOx concentration is measured based on a current signal issuing from the first pumping cell and a current signal issuing from the second pumping cell. Thus, the concentration of NOx in a measurement gas containing oxgen, for example, exhaust gas from internal combustion engines can be stably measured with high accuracy and stability.

Also, according to the present invention, the NOx concentration sensor is controlled such that NO dissociates in the first passage, thereby decreasing the oxygen concentration dependence and temperature dependence of the NOx concentration measurement. Furthermore, the calculation of NOx concentration takes into consideration the NO dissociation percentage in the first passage, so as to provide NOx concentration with high accuracy.

While the invention has been described in detail and with reference to specific embodiments thereof, it will be apparent to one skilled in the art that various changes and modifications can be made therein without departing from the spirit and scope thereof.

What is claimed is:

1. A method for measuring NOx concentration of a measurement gas containing NOx and oxygen using a two-serial-space NOx concentration sensor comprising a first internal space, a second internal space having a gas inlet, a first pumping cell comprising a solid electrolyte for effecting oxygen pumping with respect to said first space whereby a first pumping current flows through said first pumping cell, a second pumping cell comprising a solid electrolyte for effecting oxygen pumping with respect to said second space whereby a second pumping current flows through said second pumping cell, and a measurement gas space in series communication with said first space and said second space, said method comprising the steps of:

introducing said measurement gas into said first space from said measurement gas space; pumping out oxygen from said first space or pumping oxygen into said first space so that the oxygen concentration in the vicinity of the gas inlet to said second space becomes such that a portion of NO in said first space dissociates; dissociating residual NO and oxygen in gas introduced into said second space from said first space; pumping out oxygen ions from said second space which have been generated by the dissociation of said residual NO and oxygen; and determining the concentration of NOx in the measurement gas based on current signals issuing from said first and second pumping cells, wherein the NO dissociation percentage in said first space is not lower than 0.5%.

2. The method for measuring NOx concentration as claimed in claim 1, wherein said first space communicates with the measurement gas space via a first diffusion resistance element, and said second space communicates with said first space via a second diffusion resistance element.

3. The method for measuring NOx concentration as claimed in claim 1 or 2, wherein said sensor comprises an oxygen-concentration -measuring cell disposed in the vicinity of the gas inlet to said second space for detecting the concentration of oxygen in gas introduced into the second space of said NOx concentration sensor.

4. The method for measuring NOx concentration as claimed in claims 3, which comprises controlling said first pumping cell based on a signal issuing from said oxygen-concentration-measuring cell for detecting oxygen concentration in the vicinity of the gas inlet to the second space of said NOx concentration sensor.

5. The method for measuring NOx concentration as claimed in claim 3, which comprises setting an oxygen concentration target value in the vicinity of the gas inlet to said second space to a value not higher than $10^{-7}$ atm in terms of an oxygen partial pressure.

6. The method for measuring NOx concentration as claimed in claim 1, wherein the NO dissociation percentage in said first space is from 1 to 50%.

7. The method for measuring NOx concentration as claimed in claim 1, which comprises calculating the concentration of NOx in the measurement gas based on signals corresponding to the NO dissociation percentage in said first space and the quantity of NO dissociating in said second space.

8. The method for measuring NOx concentration as claimed in claim 7, wherein the current signal issuing from said second pumping cell includes an offset component corresponding to the quantity of oxygen dissociated in said second space, and which comprises calculating the concentration of NOx in the measurement gas according to the following expression:

$$\text{NOx concentration} = (Ip2 - Ip2\text{offset}) \times A / (1 - \alpha/100)$$

where $\alpha$: NO dissociation percentage in the first space (%),

A: coefficient for converting a current signal corresponding to NOx concentration to an NOx concentration, Ip2: current flowing through the second pumping cell, Ip2offset: offset component of current flowing through the second pumping cell, and NOx concentration: concentration of NOx in the measurement gas.

9. The method for measuring NOx concentration as claimed in claim 8, wherein said sensor comprises an oxygen-concentration-measuring cell disposed in the vicinity of the gas inlet to said second space for detecting the concentration of oxygen in gas introduced into the second space of said NOx concentration sensor, said method further comprises:

controlling said first pumping cell such that a signal issuing from said oxygen-concentration-measuring cell for detecting oxygen concentration in the vicinity of the gas inlet to said second space assumes a target value, calculating the concentration of oxygen in the measurement gas based on a map of a previously measured relationship between current flowing through said first pumping cell and the concentration of oxygen in the measurement gas while taking said target value as a parameter, and calculating said Ip2offset based on a map of a previously measured relationship between Ip2offset and the concentration of oxygen in the measurement gas while taking said target value as a parameter.

10. The method for measuring NOx concentration as claimed in claim 8, wherein said sensor comprises an oxygen-concentration-measuring cell disposed in the vicinity of the gas inlet to said second space for detecting the concentration of oxygen in gas introduced into the second space of said NOx concentration sensor, said method further comprises:

controlling said first pumping cell such that a signal issuing from said oxygen-concentration-measuring cell for detecting oxygen concentration in the vicinity of the gas inlet of said second space assumes a target value, calculating the concentration of oxygen in the measurement gas based on a map of a previously measured relationship between current flowing through said first pumping cell and the concentration of oxygen in the measurement gas while taking said target value as a parameter, and calculating gain represented by A/(1−α/100) using a map of a previously measured relationship between said gain and the concentration of oxygen in the measurement gas while taking said target value as a parameter.

11. The method for measuring NOx concentration as claimed in claim 1, which further comprises heating said first and second pumping cells in a temperature range of 700–900° C. and controlling the temperature drift thereof to within ±5° C.

12. An NOx concentration sensor for measuring the NOx concentration of a measurement gas containing NOx and oxygen, comprising a measurement gas space, a first internal space in communication with said measurement gas space via a first diffusion resistance element, a second internal space having a gas inlet in communication with said first space via a second diffusion resistance element, a first pumping means for pumping oxygen out from or into said first space to achieve an oxygen concentration in the vicinity of the gas inlet to said second space such that at least 0.5% of NO contained in said first space dissociates, a second pumping cell for effecting pumping action with respect to said second space, and an oxygen-concentration measuring cell disposed in the vicinity of said second diffusion resistance clement, each of said second pumping cell and said oxygen-concentration-measuring cell comprising a solid electrolyte layer and a pair of electrodes, said first space being partially defined by said first pumping means and said oxygen-concentration measuring cell, and said second space being partially defined by said second pumping cell, wherein said NOx concentration sensor further comprises:

a measuring circuit for measuring a first pumping current flowing through said first pumping means;

a measuring section for measuring a second pumping current flowing through said second pumping cell; and a calculation section for calculating the concentration of NOx in said measurement gas based on said first pumping current and said second pumping current.

13. The NOx concentration sensor as claimed in claim 12, wherein residual No and oxygen in gas introduced into said second space from said first space is dissociated in said second space, the current flowing through said second pumping cell includes an offset component corresponding to the quantity of oxygen dissociated in said second space, and said calculation section calculates the concentration of NOx in the measurement gas according to the following expression:

$$\text{NOx concentration} = (\text{Ip2} - \text{Ip2offset}) \times A/(1 - \alpha/100)$$

where

α: NO dissociation percentage in the first space (%),

A: coefficient for converting a current signal corresponding to NOx concentration to an NOx concentration, Ip2: current flowing through the second pumping cell, Ip2offset: offset component of current flowing through the second pumping cell, and NOx concentration: concentration of NOx in the measurement gas.

14. The NOx concentration sensor as claimed in claim 13, comprising a controlling section for controlling said first pumping means such that a signal issuing from said oxygen-concentration-measuring cell for detecting oxygen concentration in the vicinity of the gas inlet to said second space assumes a target value, said NOx concentration sensor further comprising:

an oxygen concentration calculation section for calculating the concentration of oxygen in the measurement gas based on a map of a previously measured relationship between current flowing through said first pumping means and the concentration of oxygen in the measurement gas while taking said target value as a parameter; and an Ip2offset calculation section for calculating said Ip2offset based on a map of a previously measured relationship between said Ip2offset and the concentration of oxygen in the measurement gas while taking said target value as a parameter.

15. The NOx concentration sensor as claimed in claim 13, comprising a controlling section for controlling said first pumping means such that a signal issuing from said oxygen-concentration-measuring cell for detecting oxygen concentration in the vicinity of the gas inlet of said second space assumes a target value, said NOx concentration sensor further comprising:

an oxygen concentration calculation section for calculating the concentration of oxygen contained in the measurement gas based on a map of a previously measured relationship between current flowing through said first pumping means and the concentration of oxygen in the measurement gas while taking said target value as a parameter; and a gain calculation section for calculating gain represented by A/(1−α/100) based on a map of a previously measured relationship between gain and the concentration of oxygen in the measurement gas while taking said target value as a parameter.

16. The NOx concentration sensor as claimed in claim 12, further comprising a heater for heating said first and second pumping cells in a temperature range of 700–900° C. and for controlling the temperature drift thereof to within ±5° C.

17. An NOx concentration sensor for measuring the NOx concentration of a measurement gas containing NOx and oxygen, comprising:

a first passage in communication with said measurement gas via a first diffusion resistance element and facing a first pumping cell, and a second passage in communication with said first passage via a second diffusion resistance element and facing a second pumping cell;

said first pumping cell causing a portion of oxygen and NO in gas diffusing within said first passage to dissociate, to thereby control the concentration of oxygen in gas contacting said second pumping cell to a level of from $2 \times 10^{-7}$ to $2 \times 10^{-10}$ atm;

said second pumping cell causing residual NO contained in gas diffusing within said second passage to dissociate;

a measuring section for measuring a first pumping current flowing through said first pumping cell;

a measuring section for measuring a second pumping current flowing through said second pumping cell;

a calculation section for calculating the concentration of NOx in said measurement gas based on said first pumping current and said second pumping current; and means for correcting NOx concentration measured by said sensor to take into account a variation in NO dissociation percentage in said first passage with a change in oxygen concentration of the measurement gas.

18. The NOx concentration sensor as claimed in claim 17, further comprising means for correcting NOx concentration measured by said sensor to take into account a variation in the ratio between the concentration of NOx in the measurement gas and the concentration of NOx in the gas diffusing into said second passage caused by control of oxygen concentration by said first pumping cell.

19. The NOx concentration sensor as claimed in claim 18, further comprising means for correcting NOx concentration measured by said sensor to take into account a variation in the ratio between the concentration of NOx in the measurement gas and the concentration of NOx in the gas diffusing into said second passage with a change in NO dissociation percentage in said first passage.

20. An NOx concentration sensor for measuring the NOx concentration of a measurement gas containing NOx and oxygen, comprising:
 a first passage in communication with said measurement gas via a first diffusion resistance element and in which oxygen and NO can dissociate;
 a second passage in communication with said first passage via a second diffusion resistance element facing a downstream end portion of said first passage and in which residual NO and oxygen in gas introduced from said first passage can dissociate;
 an oxygen-concentration-measuring cell having an electrode disposed downstream of said first passage and on an inlet side of or facing said second diffusion resistance clement, said oxygen-concentration-measuring cell outputting an electromotive force depending on the concentration of oxygen contained in gas contacting said oxygen-concentration-measuring cell;
 a first pumping cell having an electrode facing said first passage, said first pumping cell causing a portion of oxygen and NO in said first passage to dissociate by applying a voltage to the first pumping cell electrode based on the electromotive force outputting from said oxygen-concentration-measuring cell, whereby a first pumping current induced by oxygen ions generated by the dissociation of oxygen and NO flows through said first pumping cell;
 a second pumping cell having an electrode facing said second passage, said second pumping cell causing residual oxygen and NO contained in the gas diffusing within said second passage to dissociate by applying a voltage to the second pumping electrode, whereby a second pumping current induced by oxygen ions generated by the dissociation of residual oxygen and NO flows through said second pumping cell;
 a measuring section for measuring a first pumping current flowing through said first pumping cell;
 a measuring section for measuring a second pumping current flowing through said second pumping cell;
 a calculation section for calculating the concentration of NOx in said measurement gas based on said first pumping current and said second pumping current; and
 means for correcting NOx concentration measured by said sensor to take into account a variation in NO dissociation percentage in said first passage with a change in oxygen concentration of the measurement gas.

21. The NOx concentration sensor as claimed in claim 20, wherein the concentration of NOx in the measurement gas is obtained based on (i) the first pumping current flowing through said first pumping cell and including a current component induced by oxygen ions generated by partial dissociation of NO in said first passage, and (ii) the second pumping current flowing through said second pumping cell and including a current component induced by oxygen ions generated by dissociation of residual NO in said second passage.

22. The NOx concentration sensor as claimed in claim 20 or 21, wherein the electrode of said first pumping cell extends along a gas flow within said first passage and on a solid electrolyte layer constituting said first pumping cell.

23. The NOx concentration sensor as claimed in claim 20 or 21, wherein the electrode of said oxygen-concentration-measuring cell is formed on a solid electrolyte layer constituting said oxygen-concentration-measuring cell, and is located downstream of said first passage and in the vicinity of an inlet to or facing said second diffusion resistance element.

24. A method for measuring the NOx concentration of a measurement gas containing NOx and oxygen, comprising the steps of:
 diffusing the measurement gas into a first passage and subsequently into a second passage;
 causing a portion of oxygen and NO contained in the gas diffusing within said first passage to dissociate so as to control the concentration of oxygen in the gas diffusing into said second passage to a level of from $2\times10^{-7}$ to $2\times10^{-10}$ atm;
 causing residual NO and oxygen in gas diffusing within said second passage to dissociate; and
 obtaining the concentration of NOx in the measurement gas based on a first pumping current, which is induced by oxygen ions generated by dissociation of oxygen and NO within said first passage, and based on a second pumping current, which is induced by oxygen ions generated by dissociation of NO and oxygen within said second passage,
 wherein the NO dissociation percentage in said first passage is not lower than 0.5%.

25. The method for measuring NOx concentration as claimed in claim 24, which comprises obtaining the concentration of NOx in the measurement gas based on the NO dissociation percentage in said first passage.

26. The method for measuring NOx concentration as claimed in claim 25, which comprises compensating the NO dissociation percentage in said first passage based on variation in the concentration of oxygen in the measurement gas.

27. The method for measuring NOx concentration as claimed in claim 24, which comprises obtaining the concentration of NOx in the measurement gas based on the NO dissociation percentage in said first passage and the rate of variation in NO concentration associated with control of the concentration of oxygen in gas diffusing into said second passage causing a variation in the ratio between the concentration of NO in the measurement gas and the concentration of NO in the gas diffusing into said second passage.

28. An apparatus for measuring NOx concentration of a measurement gas containing NOx and oxygen, comprising:
 a first passage in communication with said measurement gas via a first diffusion resistance element and in which oxygen and NO can dissociate;
 a second passage in communication with said first passage via a second diffusion resistance element facing a downstream end portion of said first passage and in which residual NO and oxygen introduced from said first passage gas can dissociate;
 an oxygen-concentration-measuring cell having an electrode which is disposed downstream of said first passage and in the vicinity of an inlet to or facing said second diffusion resistance element, said oxygen-concentration-measuring cell outputting an electromotive force corresponding to the concentration of oxygen in gas contacting said oxygen-concentration-measuring cell;

a first pumping cell, causing a portion of oxygen and NO in said first passage to dissociate by applying a voltage to said first pumping cell based on the electromotive force outputting from said oxygen-concentration-measuring cell, whereby a first pumping current induced by oxygen ions generated by dissociation of oxygen and NO flows through said first pumping cell;

a second pumping cell causing residual oxygen and NO contained in gas diffusing within said second passage to dissociate by applying a voltage to said second pumping cell, whereby a second pumping current induced by oxygen ions generated by dissociation of residual oxygen and NO flows through said second pump cell;

first pumping cell control means for a applying voltage to said first pumping cell such that a portion of oxygen and NO in said first passage dissociates, to thereby control the concentration of oxygen in the gas diffusing into said second passage to a level of from $2 \times 10^{-7}$ to $2 \times 10^{-10}$ atm;

second pumping cell control means for applying a voltage to said second pumping cell such that residual NO and oxygen in the gas diffusing within said second passage dissociates;

a measuring section for measuring a first pumping current flowing through said first pumping cell;

a measuring section for measuring a second pumping current flowing through said second pumping cell;

a calculation section for calculating the concentration of NOx in said measurement gas based on said first pumping current and said second pumping current; and means for correcting NOx concentration measured by said sensor to take into account a variation in NO dissociation percentage in said first passage with a change in oxygen concentration of the measurement gas.

29. The apparatus for measuring NOx concentration as claimed in claim 28, further comprising:

means for storing a relationship between oxygen concentration and gain represented by $A/(1-\alpha/100)$ for NO concentration, where A is a coefficient for converting a current signal corresponding to NOx concentration to an NOx concentration and $\alpha$ is the NO dissociation percentage in the first space (%); and means for solving a relational expression between the first pumping current and oxygen concentration which includes a term whose value varies with NO concentration, and means for solving a relational expression between the second pumping current and NO concentration which includes a term whose value varies with oxygen concentration, based on said first pumping current, said second pumping current and said stored relationship between oxygen concentration and gain for NO concentration.

30. A method for measuring the concentration of a certain gas component in a measurement gas, comprising the steps of:

introducing said measurement gas into an internal passage of a gas concentration sensor including an oxygen ion pump for effecting oxygen pumping action with respect to said passage;

measuring a first pumping current flowing through said oxygen ion pump when said oxygen ion pump is operated so as to dissociate at least 0.5% of said certain gas component in the measurement gas, leaving a gas containing a residual amount of said certain gas component;

measuring a second pumping current flowing through said oxygen ion pump when said oxygen ion pump is operated so as to dissociate said residual certain gas component in the gas in which a portion of the certain gas component has been dissociated; and determining the concentration of said certain gas component in the measurement gas based on the measured first and second pumping currents.

31. An apparatus including a gas concentration sensor for measuring the concentration of a certain gas component in a measurement gas, comprising:

means for introducing said measurement gas into an internal passage of said gas concentration sensor;

an oxygen ion pump provided with electrodes and facing said passage for effecting oxygen pumping action with respect to said passage, wherein operation of said oxygen ion pump to pump out oxygen from said passage induces a pump current to flow between said electrodes;

means for measuring a first oxygen ion pump current which flows when said oxygen ion pump means is operated so as to dissociate at least 0.5% of the certain gas component contained in the measurement gas introduced into said passage and leaving a gas containing a residual amount of said certain gas component;

means for measuring a second oxygen ion pump current which flows when said oxygen ion pump means is operated so as to dissociate said residual certain gas component; and means for determining the concentration of the certain gas component contained in the measurement gas based on said first and second oxygen ion pump currents.

32. The apparatus for measuring the concentration of a certain gas component in a measurement gas as claimed in claim 31, wherein said gas component is NOx.

33. A method for measuring the concentration of NOx in a measurement gas containing NOx and oxygen, said method comprising the steps of:

introducing said measurement gas into a first internal space of a NOx concentration sensor and causing a portion of NO and oxygen in said first space to dissociate;

introducing the gas from said first space into a second internal space of said NOx concentration sensor and causing residual NO and oxygen in said second space to dissociate, wherein the NO dissociation percentage in said first space is not lower than 0.5%; and determining the concentration of NOx in the measurement gas based on the amount of NO and oxygen dissociated in said first and second spaces, wherein said NOx concentration sensor comprises a first pumping cell for effecting oxygen pumping with respect to said first space, a second pumping cell for effecting oxygen pumping with respect to said second space, a first diffusion passage for establishing communication between said first space and said measurement gas, and a second diffusion passage for establishing communication between said first space and said second space, said method comprising the steps of:

introducing said measurement gas into said first space via said first diffusion passage and applying a voltage to said first pumping cell so as to cause a portion of NO and oxygen in said first space to dissociate;

introducing the gas from said first space into said second space via said second diffusion passage, and applying voltage to said second pumping cell so as to cause residual NO and oxygen in said second space to dissociate;

measuring a first pumping current flowing through said first pumping cell;

measuring a second pumping current flowing through said second pumping cell; and obtaining the concentration of NOx in the measurement gas based on said first and second pumping currents.

34. The method for measuring the concentration of NOx in a measurement gas as claimed in claim 33, wherein said second pumping current includes an offset component corresponding to the quantity of oxygen dissociated in said second space, and which method comprises obtaining the concentration of NOx in the measurement gas based on said first and second pumping currents according to the following equations:

$$\alpha = f(Ip1);$$

$$\beta = g(Ip1);$$

and $$(1-\alpha/100) \times (NOx\ concentration) + \beta = Ip2$$

where $\alpha$: NO dissociation percentage in the first space (%), $\beta$: offset component of the second pumping current, NOx concentration: concentration of NOx in the measurement gas, Ip1: first pumping current flowing through the first pumping cell, Ip2: second pumping current flowing through the second pumping cell, f: symbol expressing a functional relationship between $\alpha$ and Ip1, and g: symbol expressing a functional relationship between $\beta$ and Ip1.

35. The method for measuring the concentration of NOx in a measurement gas as claimed in claim 33, which comprises obtaining the concentration of NOx in the measurement gas based on a previously prepared three-dimensional map of a relationship among said first pumping current, said second pumping current and the concentration of NOx in the measurement gas.

* * * * *